US008802083B2

(12) United States Patent
Vournakis et al.

(10) Patent No.: US 8,802,083 B2
(45) Date of Patent: *Aug. 12, 2014

(54) METHOD OF MAKING PLATELET AND POLY-BETA-1,4-N-ACETYLGLUCOSAMINE FIBER COMPOSITIONS

(75) Inventors: John N. Vournakis, Charleston, SC (US); Sergio Finkielsztein, Newton, MA (US)

(73) Assignee: Marine Polymer Technologies, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/475,508

(22) Filed: May 18, 2012

(65) Prior Publication Data
US 2013/0028980 A1  Jan. 31, 2013

Related U.S. Application Data

(60) Division of application No. 11/903,935, filed on Sep. 24, 2007, now abandoned, which is a continuation of application No. 10/787,035, filed on Feb. 24, 2004, now Pat. No. 7,285,266.

(60) Provisional application No. 60/449,478, filed on Feb. 24, 2003, provisional application No. 60/450,195, filed on Feb. 25, 2003.

(51) Int. Cl.
*A01N 63/00* (2006.01)
*A61K 35/16* (2006.01)
*A01N 1/02* (2006.01)
*A61L 26/00* (2006.01)

(52) U.S. Cl.
CPC .............. *A61L 26/0057* (2013.01); *A61K 35/16* (2013.01); *A01N 1/0205* (2013.01); *A01N 1/02* (2013.01); *A01L 26/0023* (2013.01)
USPC ..................................................... 424/93.72

(58) Field of Classification Search
CPC ...................................................... A61K 35/19
See application file for complete search history.

(56) References Cited

U.S. PATENT DOCUMENTS

| 4,663,289 | A | 5/1987 | Veech |
|---|---|---|---|
| 5,292,524 | A | 3/1994 | Male et al. |
| 5,446,132 | A | 8/1995 | Reed et al. |
| 5,614,204 | A | 3/1997 | Cochrum |
| 5,622,834 | A | 4/1997 | Vournakis et al. |
| 5,624,679 | A | 4/1997 | Vournakis et al. |
| 5,635,493 | A | 6/1997 | Vournakis et al. |
| 5,686,115 | A | 11/1997 | Vournakis et al. |
| 5,846,952 | A | 12/1998 | Vournakis et al. |
| 5,858,350 | A | 1/1999 | Vournakis et al. |
| 6,063,911 | A | 5/2000 | Vournakis et al. |
| 6,221,669 | B1 | 4/2001 | Livesey et al. |
| 6,413,713 | B1 | 7/2002 | Serebrennikov |
| 6,599,720 | B2 | 7/2003 | Vournakis et al. |
| 6,610,668 | B2 | 8/2003 | Vournakis et al. |
| 6,630,459 | B2 | 10/2003 | Vournakis et al. |
| 6,649,599 | B2 | 11/2003 | Vournakis et al. |
| 6,743,783 | B1 | 6/2004 | Vournakis et al. |
| 6,864,245 | B2 | 3/2005 | Vournakis et al. |
| 7,115,588 | B2 | 10/2006 | Vournakis et al. |
| 7,285,266 | B2 | 10/2007 | Vournakis et al. |
| 7,931,637 | B2 | 4/2011 | Vournakis et al. |
| 2008/0026064 | A1 | 1/2008 | Vournakis et al. |

FOREIGN PATENT DOCUMENTS

| WO | WO 95/15343 | 6/1995 |
|---|---|---|
| WO | WO 00/36918 | 6/2000 |
| WO | WO 02/063961 | 8/2002 |
| WO | WO 2004/060172 | 7/2004 |
| WO | WO 2004/076637 | 9/2004 |

OTHER PUBLICATIONS

Fischer et al., "Hemostatic properties of glucosamine-based materials", J. Biomed Mater. Res. 80 (1) : 167-174 (2007).*
Bradfield J, Bode A., 2003, "Aprotinin restores the adhesive capacity of dysfunctional platelets." *Thromb Res.* 109:181-188.
Cole et al., 1999, "A pilot study evaluating the efficacy of a fully acetylated poly-N-acetyl glucosamine membrane formulation as a topical hemostatic agent," *Surgery* 126(3):510-517.
Coller et al., 1983, "A murine monoclonal antibody that completely blocks the binding of fibrinogen to platelets produces a thrombasthenic-like state in normal platelets and binds to glycoproteins IIb and/or IIIa.," *J. Clin. Invest.* 72(1):325-338.
Feuerstein et al., 1993, "States in adherent platelet morphology and the processing of adsorbed protein on biomaterials," *Biomaterials* 14(2):137-147.
Fischer et al., 2004, "Comparison of structural and hemostatic properties of the poly-N-acetyl glucosamine Syvek Patch with products containing chitosan," *Microscopy Research and Technique* 63:168-174.
Fischer et al., 2005, "Synergistic platelet integrin signaling and factor XII activation in poly-N-acetyl glucosamine fiber-mediated hemostasis," *Biomaterials* 26: 5433-5443.
Fischer et al., 2007, "Hemostatic properties of glucosamine-based materials," *J. Biomedical. Mat. Res.* 80:167-174.
Ginsberg et al., 1983, "Reduced surface expression and binding of fibronectin by thrombin-stimulated thrombasthenic platelets," *J. Clin. Invest.* 71(3):619-624.
Hussain et al., 1999, "Reversible and irreversible intracellular Ca2+ spiking in single isolated human platelets," *J. Physiol.* 514 ( Pt 3):713-718.
Iatridis P. et al., 1964, "Surface Factor Mechanisms in Relation to Blood Platelets: Evidence That Activated Hageman Factor is Present on the Surface of Platelets." *Thrombosis et Diathesis Haemorrhagica.* 11:355-71.

(Continued)

Primary Examiner — Sandra Saucier
(74) Attorney, Agent, or Firm — Jones Day

(57) ABSTRACT

The present invention relates to compositions comprising complexes of human cells and polymer fibers and methods of their use for therapeutic purposes. Methods of making such compositions are also provided. The present invention encompasses compositions comprising poly-β-1→4-N-acetylglucosamine polymers and stored platelets and their use for promoting wound healing and achieving hemostasis.

44 Claims, 12 Drawing Sheets

(56) References Cited

OTHER PUBLICATIONS

Ikeda et al., 1996, "Simultaneous digital imaging analysis of cytosolic calcium and morphological change in platelets activated by surface contact," *J. Cell. Biochem.* 61(2):292-300.

International Search Report from International Application No. PCT/US2004/005648, dated Oct. 3, 2005.

Kuwahara et al., 1999, "Cytosolic calcium changes in a process of platelet adhesion and cohesion on a von Willebrand factor-coated surface under flow conditions," *Blood* 94(4):1149-1155.

Lewandowska et al., 1992, "Cell-type-specific adhesion mechanisms mediated by fibronectin adsorbed to chemically derivatized substrata," *J. Biomed. Mater. Res.* 26(10):1343-1363.

Mason, R, et al. 1971, "The adhesion of platelets to glass: effect of fibrinogen concentration." *Proc Soc Exp Biol Med.* 137(2):680-2.

Mattson et al., 1984, "The Bernard-Soulier platelet: II. A comparative study of changes in platelet morphology and cytoskeletal architecture following contact activation," *Scan. Electron Microsc.* (Pt 4):1941-50.

Okamoto et al., 2002, "Effect of Chitin and Chitosan on Platelet", *Advances in Chitin Science* 5, 643-649.

Peter et al., 1998, "Induction of fibrinogen binding and platelet aggregation as a potential intrinsic property of various glycoprotein IIb/IIIa (alphaIIb beta3) inhibitors." *Blood.* 92(9):3240-9.

Rozenberg et al., 1967, "Comparison of glass adhesiveness and rate of aggregation of blood platelets," *Scand. J. Clin. Lab. Invest.* 19(1):82-85.

Sathirakul et al., 1996, "Application of chitin and chitosan bandages for wound healing", *Advances in Chitin Science* 1 : 490-492.

Saucier, Sandra E., Final Office Action dated Apr. 17, 2006, U.S. Appl. No. 10/787,035 (now U.S. Patent No. 7,285,266), the U.S. Patent and Trademark Office.

Saucier, Sandra E., Non-final Office Action dated Aug. 12, 2005, U.S. Appl. No. 10/787,035 (now U.S. Patent No. 7,285,266), the U.S. Patent and Trademark Office.

Saucier, Sandra E., Non-final Office Action dated Nov. 22, 2006, U.S. Appl. No. 10/787,035 (now U.S. Patent No. 7,285,266), the U.S. Patent and Trademark Office.

Saucier, Sandra E., Non-final Office Action dated Sep. 23, 2010, U.S. Appl. No. 11/903,935, the U.S. Patent and Trademark Office.

Saucier, Sandra E., Final Office Action dated Jun. 1, 2011, U.S. Appl. No. 11/903,935, the U.S. Patent and Trademark Office.

Silberberg A. 1962, "The absorption of flexible macromolecules: part I—the isolated macromolecule at a plane interface." *J Phys Chem.* 66:1872-1883.

Supplementary European Search Report from European Application No. 04714215.3-2405 (National Stage of PCT/US2004/005648), dated May 20, 2008.

Wade et al. "Motility activation and second messenger signalling in spermatozoa from rat cauda epididymidis," 2003, *Reproduction* 125:175-83.

Wang et al. 2001, "Inhibition of hypoxia/reoxygenation-induced apoptosis in metallothionein-overexpressing cardiomyocytes," *Am J Physiol Heart Circ Physiol.* 280:H2292-9.

Written Opinion of International Application PCT/US2004/005648(WO04/076637) dated Oct. 3, 2005, International Search Authority.

Zucker H and Vroman L. 1969, "Platelet adhesion induced by fibrinogen absorbed onto glass." *Proc Soc Exp Biol Med.* 131:318-320.

\* cited by examiner

―― 10 um
Fluorescence for anti-P-selectin-PE    Phase with pGlcNAC strand outlined

METHOD OF MAKING PLATELET AND POLY-BETA-1,4-N-ACETYLGLUCOSAMINE FIBER COMPOSITIONS This application is a divisional of U.S. patent application Ser. No. 11/903,935, filed Sep. 24, 2007, which is a continuation of U.S. patent application Ser. No. 10/787,035, filed Feb. 24, 2004, now U.S. Pat. No. 7,285,266, which claims priority of U.S. provisional patent application No. 60/449,478, filed Feb. 24, 2003, and U.S. provisional patent application No. 60/450,195, filed Feb. 25, 2003, each of which is incorporated herein by reference in its entirety.

1. INTRODUCTION

The present invention relates to compositions comprising complexes of human cells and polymer fibers. The present invention further relates to methods of using such compositions in therapeutic applications. The invention also relates to methods for production of compositions comprising complexes of human cells and polymers. The present invention further relates to compositions comprising poly-N-acetylglucosamine polymers (pGlcNAc) in an alpha or beta conformation and stored platelet cells. The invention also relates to methods for wound healing and achieving hemostasis using the compositions of the invention.

2. BACKGROUND 2.1 Poly-β-1→4-N-acetylglucosamine Polymers (pGlcNAc) and Other Polysaccharides Poly-β-1→4-N-acetylglucosamine polysaccharide species are typically polymers of high molecular weight whose constituent monosaccharide sugars are attached in a 1→4 conformation. There is a body of literature on the properties, activities, and uses of polysaccharides that consist, in part, of pGlcNAc. A class of such materials has been generically referred to as "chitin", while deacetylated chitin derivatives have been referred to as "chitosan". When these terms were first used, around 1823, it was believed that chitin and chitosan always occurred in nature as distinct, well-defined, unique, and invariant chemical species, with chitin being fully acetylated and chitosan being fully deacetylated compositions. It was approximately a century later, however, before it was discovered that the terms "chitin" and "chitosan" are, in fact, very ambiguous. Rather than referring to well-defined compounds, these terms actually refer to a family of compounds that exhibit widely differing physical and chemical properties. These differences are due to the products' varying molecular weights, varying degrees of acetylation, and the presence of contaminants such as covalently bound, species-specific proteins, single amino acid and inorganic contaminants. Even today, the terms "chitin" and "chitosan" are used ambiguously, and actually refer to poorly defined mixtures of many different compounds.

For example, the properties of "chitins" isolated from conventional sources such as crustacean outer shells and fungal mycelial mats are unpredictably variable. Such variations are due not only to species differences but are also due to varying environmental and seasonal effects that determine some of the biochemical characteristics of the "chitin"-producing species. In fact, the unpredictable variability of raw material is largely responsible for the slow growth of chitin-based industries.

Production of pGlcNAc, that is either fully acetylated or uncontaminated by organic or inorganic impurities is challenging. While McLachlan et al. (McLachlan, A. G. et al., 1965, Can. J. Botany 43:707-713) reported the isolation of chitin, subsequent studies have shown that the "pure" substance obtained, in fact contained proteins and other contaminants.

Deacetylated and partially deacetylated chitin preparations exhibit potentially beneficial chemical properties, such as high reactivity, dense cationic charges, powerful metal chelating capacity, the ability to covalently attach proteins, and solubility in many aqueous solvents. The unpredictable variability of these preparations, as described above, however, severely limits the utility of these heterogenous compounds. For example, the currently available "chitins" and "chitosans" give rise to irreproducible data and to unacceptably wide variations in experimental results. Additionally, the available preparations are not sufficiently homogenous or pure, and the preparation constituents are not sufficiently reproducible for these preparations to be acceptable for use in applications, especially in medical ones.

Certain studies have met with success in producing a pure and consistent poly-β-1-4→N-acetylglucosamine product useful in therapeutic applications (Kulling et al., 1998, Endoscopy 30(3):S41-2; Cole et al., 1997, Clin. Cancer Res. 3(6): 867-73; Maitre et al., 1999, Clin. Cancer Res. 1999, 5(5): 1173-82). Uses of poly-β-1-4→N-acetylglucosamine derivatives as hemostatic agents or wound healing agents have been shown to be particularly effective (Cole et al. 1999. Surgery. 126(3):510-7; Chan et al., 2000, J. Trauma 48(3): 454-7). In addition, several patents relating to uses and derivatives of poly-β-1-4→N-acetylglucosamine products exist. U.S. Pat. No. 5,622,834 describes chemical and mechanical force methods for isolating poly-β-1-4→N-acetylglucosamine of about 4,000 to 150,000 subunits that is free of protein, substantially free of other organic contaminants, and substantially free of inorganic contaminants. U.S. Pat. No. 5,623,064 describes poly-β-1-4→N-acetylglucosamine and derivatives thereof having varying degrees of purity, acetylation, and molecular weight. U.S. Pat. No. 5,846,952 describes drug/poly-β-1-4→N-acetylglucosamine compositions. U.S. Pat. No. 5,624,679 describes biodegradable barrier-forming material comprising poly-β-1-4→acetylglucosamine or a derivative thereof. U.S. Pat. No. 5,858,350 describes a biological cell encapsulated by poly-β-1-4→N-acetylglucosamine or a derivative thereof. U.S. Pat. No. 5,635,493 describes anti-tumor drug/poly-β-1-4→N-acetylglucosamine, including a drug encapsulated by poly-β-1-4→N-acetylglucosamine and methods for anti-tumor delivery of such drugs. U.S. Pat. No. 5,686,115 describes hybrid compositions comprising poly-β-1-4→N-acetylglucosamine derivative crosslinked to another compound. U.S. Pat. No. 6,063,911 describes anti-tumor compositions comprising endothelin antagonists and poly-β-1-4→N-acetylglucosamine or poly-β-1-4→N-acetylglucosamine derivatives. U.S. Pat. No. 5,510,102 discloses compositions that act as coagulants and may be used to promote clotting of a wound by placing the compositions in contact with the wound where the composition comprises platelet rich plasma plus a biocompatable polymer that is a hemostatic agent such as alginate.

2.2 Platelet Interactions

The compositions of the invention can be used in a variety of ways to preserve platelets for longer periods of time because platelets that can be activated or remain activated after storage can produce many beneficial compounds and interactions Viability of stored platelets also has important implications in autologous therapies or procedures where a subject is administered compositions of the invention comprising self-derived platelets that have been stored.

Investigation of the interaction of platelets with "foreign" materials that has been ongoing since the original discovery of the platelet (Donne, 1842, Bizzozero et al., 1882a and 1882b). Existing evidence indicates that the interaction of platelets with foreign materials involves two steps. First, serum proteins (Silberberg, 1962, J. Physical Chem. 66:1872-1883), including adhesion proteins such as fibrinogen (Mason et al., 1971, Proc. Soc. Exp. Biol. Med. 320:123-128; Zucker and Vromen, 1969, Proc. Nat. Acad. Sci. U.S.A. 87:758-762; Feuerstein and Sheppard, 1993, Biomaterials 14:137-147), fibronectin (Lewandowska et al., 1992, J. Biomedical Materials Res. 26:1343-1363) and von Willebrand factor (vWF) (Kuwahara et al., 1999, Blood 94:1149-1155) change conformation when absorbed onto surfaces. These interactions involve multiple points of attachment of the macromolecules to the foreign materials that are "random" in nature, but the result is an alteration in solution-phase protein conformation. Secondly, the altered conformations of the absorbed proteins expose structural domains that "activate" platelet cell surface proteins. For example, fibrinogen might assume a "fibrin-like" conformation, and thus initiate outside-in signaling through the alpha$_{2b}$beta$_3$ complex. Similarly, absorbed vWF might assume a "sheared" conformation and bind to GPIb-IX complexes. A substantial body of evidence indeed indicates that alpha$_{2b}$beta$_3$ (e.g., Rozenberg and Stormorken, 1967, Scand. J. Clin. Lab. Invest. 19:82-85; Coller et al., 1983, J. Clin. Invest. 72:325-338; Ginsberg et al., 1983, J. Clin. Invest. 71:619-624) and GPIb-IX (e.g., Mattson et al., 1984, Scanning Electron Microscopy 4:1941-1950) are important for the interaction of platelets with absorbed plasma proteins. While the processes through which alpha$_{2b}$beta$_3$, GPIb-IX and other surface proteins are activated by absorbed ligands are largely undefined, it is likely that high local levels of the absorbed plasma proteins cluster glycoprotein cell surface proteins on the platelet membrane to organize cytoskeletal signaling machinery for active outside-in signaling complexes.

The plasma protein FXII (Hageman factor) has been shown to be linked with the plasma defense systems of coagulation, fibrinolysis, kallikrein-kinin and complement. FXII can be activated by complex phemonenon involving negatively charged surfaces. FXII, also binds and proteolytically activates upon contact with many anionic surfaces, and is peripherally associated (Iatridis et al., 1953, Thromb. Et Diath. 11:355-371) with the platelet surface for activation of the intrinsic coagulation pathway in the microenvironment of the cell. While the series of proteolytic steps that occurs on the platelet surface are poorly understood, the protective effect of aprotinin on platelets during cardiopulmonary bypass has been hypothesized to in part originate from an inhibition of "kallikrein-like" proteolytic events as the cells contact foreign surfaces in the extracorpealizaton device (Bradfield and Bode, 2002, Blood, in press).

Intracellular calcium signaling plays a central role in orchestrating the platelet activation response, and has been shown to occur when platelets contact glass (Ikeda et al., 1996, J. Cellular Biocem. 61:292-3000; Hussain and Mahaut-Smith, 1999, J. Physiol. 524:713-718) and polylysine (Ikeda et al., 1996, J. Cellular Biocem. 61:292-3000). The known mechanisms by which platelets interact with substances remain elusive.

2.3 Problems with Blood Storage

Concern has been steadily growing over both the national, and worldwide blood supplies. Both the integrity and reliability of existing supplies, and the ability to build larger stocks over time, have been brought into question. One reason for this is the relatively short period of storage stability of blood products. Currently, packed RBCs (red blood cell concentrates, or RCC), the dominant form of blood product for transfusions and the like, are limited to a 42-day storage period. After that time, ATP levels fall substantially, coupled with a significant loss of pH, strongly indicating a lack of viability, or, if viable, an extremely short circulation life upon infusion, in vivo. Whole blood is not stored for substantial periods. For platelets, the current storage period is even shorter, with the standard being 5 days at 22° C.

Typically, platelets are stored at 20-24° C. (approximately room temperature) with continuous gentle agitation. They are typically stored for up to 5 days, after which time they have to be discarded. Red blood cells are generally stored for 42 days. There exists a need in the art to preserve platelets and red blood cells for longer periods of time. For example, according to the congressional report entitled America's Blood Supply in the Aftermath of Sep. 11, 2001, following the Sep. 11, 2001 attacks in New York, about half a million more units of blood were collected that normally were for that time of year (H.R. Comm. Energy and Commerce, *America's Blood Supply in the Aftermath of Sep. 11, 2001*, 107th Cong., 107-137 (Sep. 10, 2002)). The report also indicates that large portions of the blood collected during this period was disposed of because the blood supply system could not process the blood fast enough or store the blood for extended periods of time. Donors were discouraged to learn the fate of their blood and those in the blood supply community were also discouraged by their inability to handle the large volume of blood, once it became evident that the low number of survivors meant a limited need for emergency blood transfusions. The need for donated blood, and thus improved storage of donated blood, is still critical. Every 3 seconds a patient in the U.S. requires blood, yet blood is a human tissue that cannot be manufactured, it must be donated.

The compositions of the invention comprising platelets can be used in a variety of therapeutic applications, and are particularly advantageous over present applications in that they make use of stored platelets which are currently disposed of after expiration for transfusion purposes.

The present invention is based on new knowledge discovered by the Inventors relating to molecular interactions between platelets and polymer fibers that be exploited for making beneficial compositions for treatment of wounds, achieving hemostasis, and implanting cells.

Citation or identification of any reference in Section 2 or in any other section of this application shall not be construed as an admission that such reference is available as prior art to the present invention.

3. SUMMARY

The present invention relates to compositions and methods for the use of complexes of human cells and polymer fibers for therapeutic uses. The invention is based in part, on the Inventor's discovery that cells form a gel when combined with polymerized N-acetylglucosamine. Furthermore, Inventors discovered that polymerized N-acetylglucosamine forms a complex by binding to cell surface proteins on human cells. In particular, Inventors have unexpectedly shown that platelets are activated in complexes of platelets and poly-N-acetylglucosamine.

The invention provides for a pharmaceutical composition comprising a complex of an isolated population of mammalian cells and substantially purified polymer fibers which interact with the mammalian cells.

The invention provides for a pharmaceutical composition comprising a complex of an isolated population of mammalian cells and substantially purified polymer fibers which interact with the mammalian cells, wherein the fibers interact with the mammalian cells by way of binding to one or more proteins present on the mammalian cells. The one or more cell surface proteins can be GPIIIa, GPIb, or $\alpha_{2b}\beta_3$ integrin.

The invention also provides for a pharmaceutical composition comprising a complex of an isolated population of mammalian cells and substantially purified polymer fibers which interact with the mammalian cells, wherein the population of mammalian cells is a population of primary mammalian cells.

The invention further provides for a pharmaceutical composition comprising a complex of an isolated population of mammalian cells and substantially purified polymer fibers which interact with the mammalian cells, wherein the composition is frozen at or below 0° C. or is stored at or below 22° C.

The invention relates to a pharmaceutical composition comprising a complex of an isolated population of mammalian cells and substantially purified polymer fibers which interact with the mammalian cells, wherein the interaction results in activation of the cells. The activation of the cells can be exhibited as a morphological change in the cells. The morphological change in the cells can comprise extension of podia.

The invention provides for a pharmaceutical composition comprising a complex of an isolated population of mammalian cells and substantially purified polymer fibers which interact with the mammalian cells, wherein the population of cells comprises lymphocytes, granulocytes, basophils, neutrophils, lymphatic cells, macrophages, endothelial cells, fibroblasts, chondrocytes, mesenchymal cells, hematopoietic cells, granulocytes, erythrocytes, eosinophils, epithelials, hepatocytes, myloid cells, stem cells or fetal cells. The population of cells can be a substantially purified population. The population of cells can also comprise cells derived from different tissues or bodily fluids. In preferred embodiments, the population of cells comprises platelets. The platelets can also be substantially purified. In other preferred embodiments, the population of cells can comprise red blood cells. The red blood cells can also be substantially purified.

The invention provides for a pharmaceutical composition comprising a complex of an isolated population of mammalian cells and substantially purified polymer fibers which interact with the mammalian cells, wherein the fibers are approximately 5 μm to 1 cm in length as detected by scanning electron microscopy. The fibers can be approximately 50 μm to 750 μm in length as detected by scanning electron microscopy. The fibers can be approximately 100 μm to 500 μm in length as detected by scanning electron microscopy. The fibers can have a width of 10-500 nm as detected by scanning electron microscopy. The fibers can have a width of 25-250 nm as detected by scanning electron microscopy. The fibers can have a width of 50-100 nm as detected by scanning electron microscopy.

The invention provides for a pharmaceutical composition comprising a complex of an isolated population of mammalian cells and substantially purified polymer fibers which interact with the mammalian cells, wherein the polymer fiber is poly-β-1→4-N-acetylglucosamine. The poly-β-1→4-N-acetylglucosamine can be microalgal poly-β-1→4-N-acetylglucosamine. The microalgal poly-β-1→4-N-acetylglucosamine can be from the *Coscinodiscus* genus, the *Cyclotella* genus, or the *Thalassiosira* genus of microalgae. The microalgal poly-β-1→4-N-acetylglucosamine can be from the *Thalassiosira* genus of microalgae and wherein the species of *Thalassiosira* is *fluviatilis* or *weissflogii*.

The invention also relates to a pharmaceutical composition comprising a complex of an isolated population of mammalian cells and substantially purified polymer fibers which interact with the mammalian cells, wherein the fibers are formulated as a gel, solid, liquid, sponge, foam, spray, emulsion, suspension, or solution, mat, string, gauze, suture, bead, microsphere, or microfibril.

The invention also provides for a pharmaceutical composition comprising a complex of an isolated population of mammalian cells and substantially purified polymer fibers which interact with the mammalian cells, wherein the composition comprises poly-β-1→4-N-acetylglucosamine fibers and platelets formulated as a suture.

The invention also provides for a pharmaceutical composition comprising a complex of an isolated population of mammalian cells and substantially purified polymer fibers which interact with the mammalian cells, wherein the ratio of the volume of cells isolated to the volume of polymer fiber suspension is 1:1.

The invention also provides for a pharmaceutical composition comprising a complex of an isolated population of mammalian cells and substantially purified polymer fibers which interact with the mammalian cells, wherein the invention further comprises a divalent cation. The divalent cation can be magnesium. The divalent cation can be calcium. The calcium can be 10% $CaCl_2$ solution.

The invention also provides for a pharmaceutical composition comprising a complex of an isolated population of mammalian cells and substantially purified polymer fibers which interact with the mammalian cells, wherein the population of cells have been isolated mammal for at least 1, 2, 3 or 4 days.

The invention also provides for a pharmaceutical composition comprising a complex of an isolated population of mammalian cells and substantially purified polymer fibers which interact with the mammalian cells, wherein the composition further comprises one or more growth factors or cytokines. The growth factor can be nerve growth factor, platelet derived growth factor (PDGF-AB), transforming growth factor-beta (TGF-($\beta_1$)), vascular endothelial growth factor (VEGF), epidermal growth factor (EGF), RBPJκ binding domain of Notch, retinoic acid, mast cell growth factor, or thrombopoietin. The growth factor can be an interferon or a tumor necrosis factor. The growth factor can be an interferon such as IFN-α, IFN-γ, IL-2, IL-4, or IL-6.

The invention also provides for a pharmaceutical composition comprising a complex of an isolated population of mammalian cells and substantially purified polymer fibers which interact with the mammalian cells, wherein the isolated cells are stored for at least 5 minutes.

The invention also provides for a pharmaceutical composition comprising a complex of an isolated population of mammalian cells and substantially purified polymer fibers which interact with the mammalian cells, wherein the polymer fiber is poly-β-1→4-N-acetylglucosamine. The poly-β-1→4-N-acetylglucosamine polymer fibers can be purified. The poly-β-1→4-N-acetylglucosamine polymers can be acetylated. The poly-β-1→4-N-acetylglucosamine polymers can be deacetylated. The poly-β-1→4-N-acetylglucosamine polymers can be free of protein, substantially free of other organic contaminants, and substantially free of inorganic contaminants. The poly-β-1→4-N-acetylglucosamine polymers can be semi-crystalline. The poly-β-1→4-N-acetylglucosamine polymers can be biodegradable and biocompatible. The poly-β-1→4-N-acetylglucosamine polymer can have a molecular weight of about 800,000 daltons to about 30 million daltons. The poly-β-1→4-N-acetylglucosamine can comprise semi-crystalline having a molecular weight of about 800,000 daltons to about 30 million daltons. The poly-β-1→4-N-acetylglucosamine polymer can have a molecular weight of about 10,000 daltons to about 800,000 daltons. The poly-β-1→4-N-acetylglucosamine can comprise semi-crystalline having a molecular weight of about 10,000 daltons to about 800,000 daltons.

The invention also provides for a composition made by mixing an isolated population of primary mammalian cells and substantially purified polymer fibers which interact with the mammalian cells under conditions that the cells and the fibers interact.

The invention also provides for a method for identifying a polymer fiber that forms complexes with cells that express GPIIIa and GPIb surface proteins comprising, contacting cells with labeled GPIIIa and GPIb surface proteins, eluting the proteins from the cells, and measuring the intensity or presence of the label, such that fibers that bind the cells are identified.

The invention also provides for a method for identifying polymers that form complexes with cells comprising, labeling poly-N-acetylglucosamine polymer fiber, mixing the labeled poly-N-acetylglucosamine polymer fiber with a test polymer fiber, adding a population of cells to the mixed fiber sample and to a pure poly-N-acetylglucosamine sample, placing the mixtures under conditions in which the binding between poly-N-acetylglucosamine and cells would normally occur, eluting the mixture to remove unbound cells and fibers, and comparing the amount of labeled poly-N-acetylglucosamine, such that a polymer fiber that competitively inhibits binding of poly-N-acetylglucosamine to cells is identified.

The invention also provides for a method for preserving a population of cells isolated from a mammal for later therapeutic use, the method comprising contacting said cells with a polymer fiber, such that a gel is formed, and freezing the gel for later applications.

The invention also provides for a method of activating a population of cells isolated from a mammal, the method comprising contacting poly-β-1→4-N-acetylglucosamine polymer fibers to the cells, thereby activating the cells.

The invention also provides for a method for accelerating wound healing a patient in need thereof comprising administering to a wound a composition comprising a population of cells isolated from a mammal and a polymer fiber, wherein the cells are derived from stored cells, and bind the polymer, such that wound healing is accelerated in the patient. The cells can be derived from the patient. The cells and polymer fibers can be combined immediately prior to or in conjunction with administering the composition to the patient.

The invention also provides for a method for reducing hemostasis time in a patient in need thereof comprising administering to a wound a composition comprising a population of cells isolated from a mammal and a polymer fiber that cells interact with, wherein the cells are derived from stored cells, such that hemostasis time is reduced in the patient. The cells can be derived from the patient. The cells and polymer fibers can be combined immediately prior to or in conjunction with administering the composition to the patient.

The invention provides for a composition comprising platelet rich plasma and purified poly-β-1→4-N-acetylglucosamine polymer, wherein the platelet rich plasma is derived from preserved platelets. The poly-β-1→4-N-acetylglucosamine polymer can be comprised of poly β-1-4-N-acetylglucosamine polymer fiber slurry. The composition can be 50% platelet rich plasma and 50% poly β-1-4-N-acetylglucosamine fiber slurry. The poly β-1-4-N-acetylglucosamine fiber slurry comprises 1 mg of poly β-1-4-N-acetylglucosamine fiber per 5 ml of distilled water.

The invention provides for a composition comprising platelet rich plasma and purified poly-β-1→4-N-acetylglucosamine polymer, wherein the composition is equal parts platelet rich plasma and poly β-1-4-N-acetylglucosamine fiber slurry and at least 0.125% $CaCl_2$ solution. The $CaCl_2$ solution is preferably a solution of approximately 10% $CaCl_2$. The composition can further comprise at least 0.125% magnesium.

The invention provides for a composition comprising platelet rich plasma and approximately 1 mg of poly β-1-4-N-acetylglucosamine fiber per approximately 1.0 ml of a 0.9% NaCl solution, wherein the platelet rich plasma is derived from preserved platelets. The platelet rich plasma can be derived from preserved platelets.

In embodiments of the invention, the composition can be a pharmaceutical composition. In other embodiments of the invention the composition can be a gel.

The invention provides for a method for preserving platelets isolated from a mammal for later therapeutic use, the method comprising contacting said platelets with poly-β-1→4-N-acetylglucosamine polymers, such that a gel is formed, and freezing the gel for later applications.

The invention provides for a method of aggregating platelets isolated from a mammal, the method comprising contacting poly-β-1→4-N-acetylglucosamine polymers to the cells, aggregating the platelets.

The invention provides for a method of activating platelets isolated from a mammal, the method comprising contacting poly-β-1→4-N-acetylglucosamine polymers to the cells, thereby activating the platelets.

The invention provides for a method for accelerating wound healing a patient in need thereof comprising administering to a wound a composition comprising platelet rich plasma and poly-β-1→4-N-acetylglucosamine polymer fiber, wherein the platelet rich plasma is derived from stored platelets, such that wound healing is accelerated in the patient. The stored platelets can be derived from the patient.

The invention provides for a method for reducing hemostasis time in a patient in need thereof comprising administering to a wound a composition comprising platelet rich plasma and poly-β-1→4-N-acetylglucosamine polymer fiber, wherein the platelet rich plasma is derived from stored platelets, such that hemostasis time is reduced in the patient. The stored platelets can be derived from the patient.

The invention provides for a method for producing a platelet-poly-β-1→4-N-acetylglucosamine polymer fiber gel comprising, mixing a populations of isolated platelets with poly-β-1→4-N-acetylglucosamine polymer fiber solution in the presence of a 10% calcium chloride solution, such that the platelets bind poly-β-1→4-N-acetylglucosamine polymer fibers in greater numbers in comparison to a mixture comprising equivalent amounts of chitosan fibers and platelets.

The invention provides for a method of identifying a candidate therapeutic agent or cell preservative, comprising contacting pGlcNAc with a cell surface protein selected from the group consisting of band III, glycophorin A, GPIb, GPIIb, and $alpha_{2b}beta_3$, which cell surface proteins protein is expressed on a cell surface and a test compound, under conditions that, in the absence of the test compound, allow pGlcNAc to bind to the cell surface protein and thereby form a pGlcNAc-cell surface protein complex; and determining whether pGlcNAc-cell surface protein complex formation is inhibited by the test compound, wherein inhibition of pGlcNAc-cell surface protein complex formation by the test compound identifies the test compound as a candidate therapeutic agent or cell preservative. In such a method, determining whether pGlcNAc-cell surface protein complex formation is inhibited by the test compound can comprise measuring the amount of binding between pGlcNAc and cell surface protein. In such a method, determining whether pGlcNAc-cell surface protein complex formation is inhibited by the test compound can comprise measuring the amount of binding between the test compound and cell surface protein. The method can be performed in vitro. The method can be performed in vivo. The cell surface can be a platelet cell surface. The cell surface can be a red blood cell surface.

The test compound can be a fiber. The fiber can be a polymer fiber. The fiber can be a protein fiber. The protein can be a human protein.

The invention provides for a method of identifying a candidate therapeutic agent or cell preservative, comprising contacting pGlcNAc with a cell surface protein selected from the group consisting of band III, glycophorin A, GPIb, GPIIb, and $alpha_{2b}beta_3$, which cell surface protein is expressed on a cell surface and a test compound, under conditions that, in the absence of the test compound, allow pGlcNAc to bind to the cell surface protein and thereby form a pGlcNAc-cell surface protein complex; and determining whether pGlcNAc-cell surface protein complex formation is inhibited by the test compound, wherein inhibition of pGlcNAc-cell surface protein complex formation by the test compound identifies the test compound as a candidate therapeutic agent or cell preservative. The method can further comprise, determining whether the test compound is capable of promoting hemostasis or accelerating the rate of wound healing, such that a test compound that is capable of promoting hemostasis or accelerating the rate of wound healing is a candidate therapeutic agent. In other embodiments, the method can further comprise, further comprising: determining whether the test compound is capable of forming a gel when mixed with platelets and, optionally, a 10% calcium chloride solution, such that a test compound that is capable of forming a gel is a candidate cell preservative.

In other embodiments, the method further comprises, prior to contacting pGlcNAc with a cell surface protein selected from the group consisting of band III, glycophorin A, GPIb, GPIIb, and $alpha_{2b}beta_3$, which cell surface protein is expressed on a cell surface and a test compound, under conditions that, in the absence of the test compound, identifying a suitable test compound by a method comprising, contacting pGlcNAc with the cell surface protein and a molecule, under conditions that, in the absence of the molecule, allow the pGlcNAc to bind to the cell surface protein and thereby form an pGlcNAc-cell surface protein complex; and determining whether pGlcNAc-cell surface protein complex formation is inhibited by the molecule wherein inhibition of pGlcNAc-cell surface protein complex formation by the molecule identifies the molecule as a suitable test compound. The pGlcNAc can be contacted with the cell surface protein prior to contacting the pGlcNAc with the molecule. The pGlcNAc can be contacted with the molecule prior to contacting the pGlcNAc with the cell surface protein. The cell surface protein can be contacted with the molecule prior to contacting the pGlcNAc with the cell surface protein and the test compound. The cell surface protein can be immobilized on a solid surface. The cell surface protein can be present in a cell membrane, which cell membrane is immobilized on the solid surface.

The invention provides for a method of identifying a candidate therapeutic agent or cell preservative, comprising, contacting pGlcNAc with a test compound and a cell surface protein selected from the group consisting of band III, glycophorin A, GPIb, GPIIb, and $alpha_{2b}beta_3$, under conditions that, in the absence of the test compound, allow the pGlcNAc to bind to the cell surface protein and thereby form an pGlcNAc-cell surface protein complex; and determining whether pGlcNAc-cell surface protein complex formation is inhibited by the test compound, wherein inhibition of pGlcNAc-cell surface protein complex formation by the test compound identifies the test compound as a candidate therapeutic agent or cell preservative. The pGlcNAc is contacted with the cell surface protein prior to contacting the pGlcNAc with the test compound. The pGlcNAc is contacted with the test compound prior to contacting the pGlcNAc with the cell surface protein. The cell surface protein is contacted with the test compound prior to contacting the pGlcNAc and the test compound. The pGlcNAc is a pGlcNAc fiber. The test compound is a fiber. The fiber is a polymer fiber. The fiber is a protein fiber. The protein is a human protein.

The invention provides for a method of identifying a candidate therapeutic agent or cell preservative, that comprises, contacting pGlcNAc with a test compound and a cell surface protein selected from the group consisting of band III, glycophorin A, GPIb, GPIIb, and $alpha_{2b}beta_3$, under conditions that, in the absence of the test compound, allow the pGlcNAc to bind to the cell surface protein and thereby form an pGlcNAc-cell surface protein complex; and determining whether pGlcNAc-cell surface protein complex formation is inhibited by the test compound, wherein inhibition of pGlcNAc-cell surface protein complex formation by the test compound identifies the test compound as a candidate therapeutic agent or cell preservative, wherein determining whether pGlcNAc-cell surface protein complex formation is inhibited by the test compound can comprise measuring the amount of binding between pGlcNAc and cell surface protein.

The invention provides for a method of identifying a candidate therapeutic agent or cell preservative, that comprises, contacting pGlcNAc with a test compound and a cell surface protein selected from the group consisting of band III, glycophorin A, GPIb, GPIIb, and $alpha_{2b}beta_3$, under conditions that, in the absence of the test compound, allow the pGlcNAc to bind to the cell surface protein and thereby form an pGlcNAc-cell surface protein complex; and determining whether pGlcNAc-cell surface protein complex formation is inhibited by the test compound, wherein inhibition of pGlcNAc-cell surface protein complex formation by the test compound identifies the test compound as a candidate therapeutic agent or cell preservative, wherein determining whether pGlcNAc-cell surface protein complex formation is inhibited by the test compound comprises measuring the amount of binding between the test compound and cell surface protein.

The invention provides for a method of identifying a candidate therapeutic agent or cell preservative, that comprises, contacting pGlcNAc with a test compound and a cell surface protein selected from the group consisting of band III, glycophorin A, GPIb, GPIIb, and $alpha_{2b}beta_3$, under conditions that, in the absence of the test compound, allow the pGlcNAc to bind to the cell surface protein and thereby form an pGlcNAc-cell surface protein complex; and determining whether pGlcNAc-cell surface protein complex formation is inhibited by the test compound, wherein inhibition of pGlcNAc-cell surface protein complex formation by the test compound identifies the test compound as a candidate therapeutic agent or cell preservative, further comprising: determining whether the test compound is capable of promoting hemostasis or accelerating the rate of wound healing, such that a test compound that is capable of promoting hemostasis or accelerating the rate of wound healing is a candidate therapeutic agent.

The invention provides for a method of identifying a candidate therapeutic agent or cell preservative, that comprises, contacting pGlcNAc with a test compound and a cell surface protein selected from the group consisting of band III, glycophorin A, GPIb, GPIIb, and alpha$_{2b}$beta$_3$, under conditions that, in the absence of the test compound, allow the pGlcNAc to bind to the cell surface protein and thereby form an pGlcNAc-cell surface protein complex; and determining whether pGlcNAc-cell surface protein complex formation is inhibited by the test compound, wherein inhibition of pGlcNAc-cell surface protein complex formation by the test compound identifies the test compound as a candidate therapeutic agent or cell preservative, further comprising: determining whether the test compound is capable of forming a gel when mixed with platelets and, optionally, a 10% calcium chloride solution, such that a test compound that is capable of forming a gel is a candidate cell preservative.

As used herein the terms "isolated cells", "isolated platelets", or "isolated platelets" mean cells or platelets that have been changed or removed from its original environment, or both. With respect to mammalian platelets, cells become isolated when they have been removed from a mammal's body. This can be true even if the cells are still in a mixed cell population.

As used herein the term "matrix" means any solid or semisolid, e.g. gel, structure. In particular, "matrix" refers to compositions of polymer fibers and cells.

4. BRIEF DESCRIPTION OF THE FIGURES

FIG. 1 The number of platelets per mg of pGlcNAc matrix increases proportional to the number of platelets per mg of pGlcNAc originally mixed together. No saturation point was observed. The greatest ratio observed was 5×10$^8$ platelets per mg of pGlcNAc, though this was not established as an upper limit. The ratios labeled by 1 and 2 on the graph represent reactions of fresh platelets and deacetylated pGlcNAc sponge. The ratio labeled by 3 on the graph represents stored platelets and fully acetylated pGlcNAc slurry.

FIG. 2 2A. The number of platelets per mg of pGlcNAc is shown for four formulations of pGlcNAc: deacetylated sponge, deacetylated membrane, acetylated sponge, and acetylated membrane. The deacetylated formulations and the sponge formulations held greater numbers of platelets in comparison to the acetylated and membrane formulations respectively. 2B. A macroscopic view of four formulations with fluorescence labeled platelets associated, indicating relative degrees of fluorescence.

FIG. 3 Panel A. Scanning Electron Microgram of activated platelet cell with extended pseudopodia contacting a pGlcNAc polymer fiber. Panel B. Fluorescence microgram of labeled platelets associated with pGlcNAc fiber and phase mircrogram of platelets associated with pGlcNAc fiber.

FIG. 4 4A. The number of platelets absorbed per mg pGlcNAc polymer fiber matrix decreased in the presence of inhibitors of alpha$_{2b}$beta$_3$, i.e. echistatin and lloprost, in comparison to a control (carrier). 4B. Lanes 1-3 show SDS-PAG electrophoresis of total platelet protein stained with colloidal Coomassie stain (CCB). Lane 1 shows proteins derived from whole platelets, lane 2 shows proteins derived from pGlcNAc absorbed proteins and plasma, and lane 3 shows proteins derived from plasma derived from pGlcNAc absorbed proteins alone. Lanes 4 and 5 show SDS-PAG electrophoresis of a more stringent denaturing and staining of platelet cell surface proteins with streptaviden-alkaline phosphatase (alk phos). Several surface proteins were identified including P-selectin, GPIIIa, GPIb, and GPIIb.

FIG. 5 Scanning electron micrographs of lyophilized platelets on pGlcNAc matrix indicate cells exhibit an activated morphology.

FIG. 6 Lanes 1-3 show SDS-PAG electrophoresis of Glycoprotein IIb, IIa and Ib/V/IX complexes derived from whole platelets. Lanes 4-6 show SDS-PAG electrophoresis of Glycoprotein IIb, IIa and Ib/V/IX complexes derived from pGlcNAc absorbed proteins.

FIG. 7 Western blot analysis using anti-GPIIb/IIb and anti-GPIb/V/IX antibodies to confirm the presence of platelet GPIIb/IIb and GPIb/V/IX complexes absorbed by a pGlcNAc polymer fiber matrix.

FIG. 8 Lanes 1-3 show total protein derived from red blood cells stained with colloidal Coomassie stain (CCB). Lane 1 shows protein from whole red blood cells, lane 2 shows red blood cells and plasma derived from samples absorbed by pGlcNAc, and lane 3 shows plasma alone derived from a sample absorbed by pGlcNAc polymer fibers. Lanes 4 and 5 show red blood cell surface proteins stained with streptaviden-alkaline phosphatase (alk phos). Lane 4 shows surface proteins from whole red blood cells, and lane 5 shows surface proteins derived from a sample absorbed by pGlcNAc polymer fibers. Lanes 6 and 7 show Western blots using anti-glycophorin A (lane 6) and anti-band III antibodies (lane 7) to confirm the presence of red blood cell surface proteins associated with pGlcNAc.

FIG. 9 Western blot analysis using anti-glycophorin A and anti-band III antibodies to confirm red blood cell surface proteins were absorbed by pGlcNAc polymer fiber.

5. DETAILED DESCRIPTION OF THE INVENTION

The present invention relates to the use of compositions comprising complexes of human cells and polymers for therapeutic uses. The invention also encompasses methods for production of compositions comprising complexes of cells and polymers. Numerous types of cells can be used in the compositions of the invention. Likewise various fibers can also be used in the compositions of the invention. Methods for screening potential fibers and identifying fibers that cells interact with to form the complexes of the invention are described herein. The invention also relates to methods for wound healing and achieving hemostasis using the compositions of the invention. In particular, compositions comprising poly-β-1→4-N-acetylglucosamine polymers (pGlcNAc) and stored platelets are disclosed herein.

The present invention is based in part on the inventors' determination of a basic mechanistic understanding of how platelets interact with poly-N-acetylglucosamine polymer (pGlcNAc) fibers. Inventors have identified the proteins on the platelet surface that mediate the interaction of platelets with the glucosamine polymer. Employing confocal microscopy with fluorescent antibody probes, the inventors identified platelet cell surface protein/adhesion molecule complexes (e.g., alpha$_{2b}$beta$_3$-fibrinogen) that localize to the contact points of the pGlcNAc polymer fiber with platelets, as well as chemical cross-linking studies to determine the lipids and proteins on platelets that directly contact (within about 20 angstrom) the pGlcNAc polymer fiber.

5.1 Cells that can be Used in the Compositions and Methods of the Invention

Cells that can be used in the methods and compositions of the invention include but are not limited to fibroblasts, smooth muscle cells, platelets, and red blood cells. Any cell type that can be isolated and interacts with the polymers of the invention to form a gel can be used in the compositions and methods of the invention. In a preferred embodiment the cells used are mammalian cells, most preferably human cells. However, the cells may be derived from other organisms, or the cells can be single celled life forms. For example, beneficial single-celled microrganisms can be used to produce compositions for administration to patients in need of such organisms. In other embodiments the cells are recombinant cells, engineered to produce or overexpress genes encoding polypeptides that are biologically useful compounds such as, but not limited to, platelet-derived growth factor PDGF, insulin, peptides, or hormones. A list of such compounds can be found in Section 5.4.3.

The compositions of the invention contain a population of cells in which substantially the cells are living cells, however in less preferred embodiments at least 90%, 80%, 70%, 60%, 50%, 40%, 30%, 20%, 20%, 10% or 5% of the cells of the compositions and methods of the invention are living cells.

Preferably, when human cells are utilized, the cells are all derived from a single individual, for each product made from the compositions of the invention. Such products are advantageous for autologous therapeutic applications. In other embodiments, the cells used in producing the compositions of the invention are derived from separate origins, either a different individual of the same species (allogeneic), or from a different species (xenogeneic). An example, although not a limiting example, would be the combination of platelets that had been isolated from different human individuals.

The cells can be freshly isolated from a mammal, or the cells can be isolated and stored for about 10 minutes, 20 minutes, 30 minutes, 40 minutes, 50 minutes, 1 hour, 1.5 hours, 2 hours, 2.5 hours, 3 hours, 4 hours 7 hours, 10 hours, 15 hours, 1 day, 2 days, 3 days, 4 days, 5 days, 6 days, 7 days, 8 days, 9 days, 10 days, 11 days, 12 days, 13 days, 14 days, or 15 days. In certain embodiments, the isolated cells can be stored in at room temperature or low temperatures (e.g., 22° C. or 4° C. respectively) and/or with additives for preservation and other purposes such as those described in Section 5.4.3.

In certain embodiments, about 5%, 10%, 20%, 30%, 40%, 50%, 60%, 70%, 80%, 90%, or 100% of the cells that contact the polymers of the compositions of the invention aggregate. In other embodiments, about 5-15%, 10-20%, 15-25%, 30-40%, 25-35%, 40-50%, 45-55%, 50-60%, 55-65%, 60-70%, 65-75%, 70-80%, 75-85%, 80-90%, 85-95%, 90-100%, or 95-100% of the cells that contact the polymers of the compositions of the invention aggregate.

In certain embodiments, the compositions of the invention contain a population of cells that is purified with respect to the cell type(s) of interest (e.g., platelets). In certain specific embodiments, the purified population of cells contains a total of no more 40%, 30%, 20%, 10%, 5%, 4%, 3%, 2% or 1% of cells of a type other than the cell type(s) of interest. Thus, in such embodiments, the cell type(s) of interest in the compositions of the invention represent at least 60%, at least 70%, at least 80%, at least 90%, at least 95%, at least 96%, at least 97%, at least 98% or at least 99% of all the cells in the composition.

In the compositions of the invention, each cell can have one or a few points of contact with the polymer fiber. In certain embodiments, the individual cells are not encapsulated by the polymer fibers. The polymer fibers of the invention form a matrix that allows for absorption of cells and a more open interaction of cells and polymer fibers. This differs distinctly from a cell encapsulated with a polymer fiber for the purpose of delivery of the cell. In such instances the polymer fiber acts as a coating not as an open matrix that allows for interaction of cells with polymer fibers and/or interactions between the cells that are interacting with the fibers, e.g., platelets associated with poly-$\beta$-1$\rightarrow$4-N-acetylglucosamine polymers, wherein said platelets interact with and aggregate with each other. Within the context of a composition of the invention, a polymer fiber is deemed to aggregate if it is in contact with at least one other polymer fiber and/or one cell, and a cell is deemed to aggregate is it is in contact with at least one polymer fiber and/or one other cell. Aggregation can be readily determined using standard microscopic techniques. In preferred embodiments, polymer fibers and cells in the compositions of the invention aggregate by contacting a plurality of other polymer fibers and/or cells.

Mixtures of cell populations or types, such as, but not limited to, platelets and cells of the immune system can be combined with polymers in producing the compositions of the invention. In such mixtures, only one cell type need be identified as capable of interacting with the polymer. Such mixtures of cell types can be naturally occurring and mixed with proteins and other non-cellular components, as is the case in blood, or the mixtures of cell types can be made by isolating and purifying cell types and then mixing the populations of cells in desired ratios which may or may not occur naturally. Such mixtures may also include naturally occurring or synthetic additives such as those described in Section 5.4.3.

There are many reasons why one would want to control number of cells in a composition of he invention. For example, in certain embodiments, one might combine a certain number of platelets with a pGlcNAc formulation without saturating the pGlcNAc polymer fiber matrix. The resulting composition could be frozen for later use, or used immediately. Additional cells could be added immediately before applying the composition. In other embodiments the composition can be applied so that cells or fluid from the body of the patient interact with the pGlcNAc fibers not already bound by platelets or are absorbed by the polymer fiber matrix.

Any type of cell can be used in the compositions and methods of the invention provided the cell interacts with a polymer fiber to form a complex. In some embodiments, cells that interact with polymer fibers express certain surface proteins. Some non-limiting examples of these include band III and glycophorin A found on cells such as, but not limited to, red blood cells and GPIb, GPIIb, and alpha$_{2b}$beta$_3$ found on cells such as, but not limited to, platelets.

Cells for use in the present compositions and methods can be primary cells (fresh or stored, as discussed above) or cell lines, or from any species, including but not limited to human, animal, plant, mammal, vertebrate, primate, mouse, rat, dog, cat, horse, pig, or cow.

In a preferred embodiment, the cell populations for use in the present compositions and methods are purified or at least highly enriched. However, it is not necessary to use cells that are a pure population in the methods and compositions of the present invention.

The isolation of cells for use in the present invention can be carried out by any of numerous methods commonly known to those skilled in the art. For example, one common method for isolating cells is to collect a population of cells from a patient and using differential antibody binding, wherein cells of one or more certain differentiation stages are bound by antibodies to differentiation antigens, fluorescence activated cell sorting is used to separate the desired cells expressing selected differentiation antigens from the population of isolated cells. The following section describes exemplary methods for the isolation and culturing of various types of cells for use in the methods and compositions of the present invention. In addition, any method known in the art can be employed.

In a specific embodiment, the cell is a stem cell.

5.1.1 Platelets

In certain embodiments, platelets can be used in the compositions and methods of the invention. Platelets are colorless cells that are present in blood. The sticky cell surface functions in the formation of clots to stop bleeding. When bleeding from a wound suddenly occurs, the platelets gather at the wound and attempt to block the blood flow. The mineral calcium, vitamin K, and fibrinogen help the platelets form a clot. The platelets react with the fibrinogen to begin forming fibrin. The fibrin then forms a web-like mesh that traps the blood cells within it. Calcium and vitamin K must be present in blood to support the formation of clots. Thus, including platelets in the compositions of the invention results in products that contain platelets that can function immediately upon administration to a wound site and accelerate the wound healing process.

The platelets cells used in the compositions and methods of the invention can be isolated by any means known in the art, such as those described in Section 6. In a preferred embodiment, the cells are isolated as platelet rich plasma.

In preferred embodiments, the platelets are stored or derived from stored blood that has expired for use in transfusion purposes. Most stored platelets, platelets plus plasma, and stored blood are normally destroyed after about 3 to 5 days at 22° C. Thus, the present compositions and methods, provide a means for further storage and use of platelets which would otherwise be destroyed. Platelet storage techniques such as those disclosed in U.S. Pat. No. 6,221,669 and U.S. Pat. No. 6,413,713 are based on inactivation of platelets. Temperatures also inhibit platelets from biologically activating during storage. Low temperatures (4 or 22° C.) inhibit activation and preserve cell shape. Cells that have been preserved and/or stored as described above can be used in the methods and compositions of the invention.

In one embodiment, the platelets are harvested by apheresis, wherein platelets or cells are removed from a donor and the remaining portions of blood serum (e.g., red cells, leukocytes and plasma) are returned to the donor.

The compositions of the invention that comprise frozen cell-polymer fiber compositions can be stored for days, months or years. Preferably, the compositions are stored until the patient is in need thereof. In other embodiments, for example prior to a planned surgery, the compositions are stored for a period of time that allows the patient to recover from blood or cell extraction and naturally replace the blood or cells removed from the patient.

In certain embodiments, about 5%, 10%, 20%, 30%, 40%, 50%, 60%, 70%, 80%, 90%, or 100% of the platelets that contact the polymers of the compositions of the invention aggregate.

Platelets also produce platelet derived growth factor (PDGF) (Ross 1978, Cell 14:203; Antoniades et al., 1975, Proc. Natl. Acad. Sci. USA 72:2635). PDGF is now known to be produced by a number of cell types besides platelets and it has been found to be a mitogen for almost all mesenchymally-derived cells, i.e., blood, muscle, bone/cartilage, and connective tissue cells (Raines, 1993, in Biology of Platelet-Derived Growth Factor, Westermark, B. and C. Sorg, eds., Basel, Karger, p. 74). PDGF produced by platelets and is responsible for proliferation of vascular smooth muscle cells (VSMC) and fibroblasts in wound sites. In certain embodiments, it is beneficial to have a platelet-polymer fiber matrix that comprises other cell types that are affected by PDGF or other biologically active agents, e.g., hormones, peptides, see Section 5.4.3, produced by the platelets. In such embodiments, the second type of cell does not necessarily have to interact with the polymer fiber. The invention as described herein provides for at least one cell type that interacts with the polymer fiber. A non-limiting example is a polymer fiber-platelet matrix with fibroblasts, that is formulated as a membrane and can be implanted or applied to a wound site topically or internally. Such a matrix composition would benefit from the production of PDGF by platelets, which would affect the fibroblasts cells during the formation of a clot. In such embodiments, fibroblasts could be added to the compositions immediately prior to administration of the composition. If a composition simply comprised platelets and polymer fiber, upon application the platelets of the composition can have the same effect on endogenous fibroblast cells that come into contact with the composition.

In other embodiments, platelet-polymer fiber compositions are added to in vitro cultures of other cell types as a means for production and release of biologically active agents produced by the platelets. In other embodiments, such matrixes can be implanted for in vivo production and release of agents. In other embodiments, the platelet-polymer fiber matrices of the invention can be maintained in culture for production and subsequent collection/purification of biologically active agents for therapeutic uses. In yet other embodiments, cell types that are much rarer that platelets, such a beta cells, that produce valuable biologically active compounds, are incorporated into the compositions of the invention comprising platelets and polymer fibers. In such embodiments, the platelets produce agents, such as PDGF, that assist in maintaining the rare cells, thus increasing the production of compounds produced by the rare cells or proliferation and establishment of the rare cells themselves. One of skill in the art can clearly envision both in vivo and in vitro applications of such compositions. In preferred embodiments, the platelets are activated and/or exhibit activated morphology as described in the Examples Section 9.

In one embodiments, where the cell-polymer fiber compositions and related methods of the invention comprise platelet rich plasma, the platelet rich plasma is made with an automated platelet enrichment system. Automated platelet enrichment systems contemplated for use in preparing the platelet rich plasma of the compositions and methods of the invention may produce an average percent recovery of platelets from whole blood that is about 30%, 35%, 40%, 45%, 50%, 55%, 60%, 65%, 70%, 75%, or 80%. Such automated systems my also generate about 30%, 35%, 40%, 45%, 50%, 55%, or 60% less platelet activation that traditional centrifuge techniques. Such automated systems my also be used to generate growth factors and other compounds produced by platelets for use in the compositions and methods of the invention, including, but not limited to, platelet derived growth factor (PDGF-AB), transforming growth factor-beta (TGF-$\beta_1$), vascular endothelial growth factor (VEGF), platelet-derived angiogenisis factor (PDAF), platelet-derived endothelial cell growth factor (PD-ECGF), serotonin, catecholamines, ADP, fibrinogen, fibronectin, ATP, factor V, Von Willebrand factor 8, thromboxane A2, calcium, or epidermal growth factor (EGF). In certain related embodiments the automated platelet enrichment system is SmartPReP™ or Symphony™. Such automated systems are particularly useful in conjunction with the compositions and methods of the invention, wherein the platelets or factors of the composition of the invention are autologous to the subject to which they are administered and/or where platelets are preserved using the methods of the invention. Alternately the platelets may be derived from a family or community donor who has been specifically matched to the patient on the basis of HLA (Human Lymphocyte Antigen) typing.

5.1.2 Red Blood Cells (RBC)

Red blood cells are responsible for the transport of oxygen and carbon dioxide. RBC's are terminally differentiated and can never divide. They live about 120 days and then are ingested by phagocytic cells in the liver and spleen. Most of the iron in their hemoglobin is reclaimed for reuse. The remainder of the heme portion of the molecule is degraded into bile pigments and excreted by the liver. Red blood cells express numerous cell surface proteins including glycophorin A and band III. With respect to glycophorin A, each RBC has some 500,000 copies of the molecule embedded in its plasma membrane. Thus, Inventor's discovery that red blood cells interact with pGlcNAc fibers via glycophorin A is not only unexpected, but provides a basis for numerous uses based on the potential strength of the interaction due to the number of glycophorin A proteins on a cell surface.

During clot formation red blood cells become entangled in fibrin webs and thus contribute to the formation of clots and hemostasis. Thus, red blood cells complexed with the polymer fibers of the invention can be used to accelerate wound healing and hemostasis.

In preferred embodiments, the red blood cells can be derived from stored blood that has expired for use in transfusion purposes. Most stored red blood cells in stored blood are normally destroyed after about 3 to 5 days at 22° C. Thus, the present compositions and methods, provide a means for further storage and use of red blood cells which would otherwise be destroyed. Other uses for compositions of the invention comprising red blood cells and polymer fibers, include autologous treatments. Application to wounds or coating objects and instruments used internally with the compositions of the invention comprising red blood cells that have interacted with polymer fibers reduces the likelihood of rejection by the immune system of the patient.

5.1.3 Mesenchymal Cells

Mesenchymal cells can also be used and are generally recognized as multipotential cells which are capable of dividing many times to produce progeny cells that can eventually give rise to skeletal tissues, including cartilage, bone, tendon, ligament, marrow stroma and connective tissue.

5.1.3.1 Stem Cells

One of the most important type of progenitor cells vis a vis for therapeutic applications are those derived from the mesenchyme. Mesenchymal progenitors give rise to a very large number of distinct tissues (Caplan, 1991, J. Orth. Res 641-650). Most work to date involves the isolation and culture of cells which can differentiate into chondrocytes and osteoblasts. The systems developed to isolate the relevant progenitor cell populations were worked out first in chick embryos (Caplan, 1970, Exp. Cell. Res. 62:341-355; Caplan, 1981, 39th Annual Symposium of the Society for Developmental Biology, pp. 37-68; Caplan et al., 1980, Dilatation of the Uterine Cervix 79-98; DeLuca et al., 1977, J. Biol. Chem. 252:6600-6608; Osdoby et al., 1979, Dev. Biol. 73:84-102; Syftestad et al., 1985, Dev. Biol. 110:275-283). Conditions were defined under which chick mesenchymal cells differentiated into chondrocytes and bone. Id. With regard to cartilage and bone, the properties of mouse or human mesenchymal limb appear to be quite similar if not identical (Caplan, 1991, J. Orth. Res. 641-650). Mesenchymal cells capable of differentiating into bone and cartilage have also been isolated from marrow (Caplan, 1991, J. Orth. Res. 641-650).

Caplan et al., 1993, and Caplan et al., 1996, U.S. Pat. Nos. 5,226,914 and 5,486,359 respectively, describe exemplary methods for isolating mesenchymal stem cells from bone marrow.

Several bone marrow isolation protocols have been reported and can be used to obtain progenitor cells. Single cell suspensions from rat bone marrow can be prepared according to Goshima et al., 1991, Clin. Orth. and Rel. Res. 262:298-311. Human stem cell cultures from marrow can be prepared as described by Bab et al., 1988, Bone Mineral 4:373-386 as follows: Whole marrow cells are obtained from five patients. The marrow samples are separated from either the iliac crest or femoral midshaft. Marrow samples, 3 ml in volume, are transferred to 6 ml of serum-free Minimal Essential Medium (MEM) containing 50 U/ml penicillin and 0.05 mg/ml streptomycin-sulfate. A suspension of predominantly single cells is prepared as described previously (Bab et al., 1984, Calcif. Tissue Int. 36:77-82; Ashton et al., 1984, Calcif. Tissue Int. 36:83-86) by drawing the preparation into a syringe and expelling it several times sequentially through 19, 21, 23 and 25 gauge needles. The cells are counted using a fixed volume hemocytometer and the concentration adjusted to $1-5 \times 10^8$ total marrow cells per ml suspension. Positive and negative control cell suspensions can be set as described before (Shteyer et al., 1986, Calcif. Tissue Int. 39:49-54), using rabbit whole marrow and spleen cells, respectively.

5.1.3.2 Chondrocytes

Chondrocytes can be obtained from normal mature cartilage tissue. For example, both U.S. Pat. No. 4,846,835 to Grande, issued Jul. 11, 1989, and U.S. Pat. No. 5,041,138 to Vacanti et al., issued Aug. 20, 1991, disclose the obtention of chondrocytes by digesting articular cartilage in a collagenase solution, followed by mitotic expansion of the chondrocytes in an in vitro culture medium prior to implantation.

5.1.4 Connective Tissue

Connective tissue comprises fibroblasts, cartilage, bone, adipose and smooth muscle cells. Fibroblasts are the least differentiated of the connective tissue cells and are dispersed in connective tissues throughout the body. They can be identified by their characteristic secretion of type I and/or type III collagen. Fibroblasts can migrate into tissue wounds and secrete a collagenous matrix that heals and isolates the wounds. Further, they can differentiate into other members of the connective tissue family, depending on their local cues. Fibroblasts can thus be combined with the compositions of the invention either as cells that potentially interact with the polymer and/or in addition to such cells that interact with the polymer. Fibroblasts can be isolated from a variety of different tissues, including but not limited to the bone marrow stroma, according to methods known to those of ordinary skill in the art.

The utility of fibroblasts lies not only in their plasticity, i.e. ability to differentiate into many cell types, but also the ease of growing the cells in culture and their rapid division. Fibroblasts can therefore be grown using basic tissue culture techniques well known to those skilled in the art and described in many readily available publications, e.g. Freshney, 1994, Culture of Animal Cells, third edition, Wiley-Liss Inc. New York.

5.1.5 Endothelium

Endothelial cells can also be used in the compositions and methods of the invention, particularly for therapeutic applications related to cardiovascular tissues. Endothelial cells can be used including endothelial cells which have been modified to resist lysis and activation by complement and evade the host's immune mechanisms for removing foreign cells, when inserted into a non-autologous host such as those described in U.S. Pat. No. 6,100,443, which is incorporated by reference herein.

Endothelial membrane isolation and separation from associated tissue is described by Schnitzer et al. in U.S. Pat. No. 5,610,008. Additionally, endothelial culture techniques have been described in scientific publications (e.g. Haudenschild et al., 1976, Exp. Cell Res. 98:175-183; Folkman and Haudenschild, 1980, Nature 288:551-556). In humans, endothelial cells have been successfully isolated from human umbilical veins (Jaffe et al., 1973) and human adipose (Kern et al., 1983, J. Clin. Invest. 71:1822-1829) and dermal (Davison et al., 1983, In Vitro 19:937-945) capillaries. Generally, they are released from the surrounding tissue by collagenase treatment and grown on a suitable substrate in the presence of growth factors (see Zetter, 1994, in Culture of Animal Cells, third edition, Wiley-Liss Inc., New York, p. 334).

5.1.6 Neuroectodermal Cells

5.1.6.1 Neural Stem Cells

It is generally assumed that neurogenesis in the central nervous system ceases before or soon after birth. In recent years, several studies have presented evidence indicating that at least to some degree new neurons continue to be added to the brain of adult vertebrates (Alvarez-Buylla and Lois, 1995, Stem Cells (Dayt) 13:263-272). The precursors are generally located in the wall of the brain ventricles. It is thought that from these proliferative regions, neuronal precursors migrate towards target positions where the microenvironment induces them to differentiate. Studies have been reported where cells from the sub-ventricular zone can generate neurons both in vivo as well as in vitro, reviewed in Alvarez-Buylla and Lois, 1995, Stem Cells (Dayt) 13:263-272.

The neuronal precursors from the adult brain can be used as a source of cells for neuronal transplantation (Alvarez-Buylla, 1993, Proc. Natl. Acad. Sci. USA 90:2074-2077). Neural crest cells have also been long recognized to be pluripotent neuronal cells which can migrate and differentiate into different cell neuronal cell types according to the instructions they receive from the microenvironment they find themselves in (LeDouarin and Ziller, 1993, Curr. Opin. Cell Biol. 5:1036-1043).

Mature neurons and glia may be isolated by methods known to those skilled in the art.

5.1.6.2 Endocrine Cells

Specialized cells such as pancreatic beta cells which can have a therapeutic effect by increasing insulin supply in the blood can also be used in the present methods and compositions. Pancreatic islets (islets of Langerhans), hepatocytes or other types of glandular cells may also be used.

Endocrine cells of the thyroid, parathyroid and pancreas may be isolated and cultured by the methods described in U.S. Pat. Nos. 5,888,816 and 5,646,035 by Coon et al.

5.1.7 Fetal Cells

The fact that fetal brain tissue has been shown to have clear behavioral effects when transplanted into adult lesioned brains, has focused attention on human fetal tissue as a potential cell source in transplantation protocols designed to improve neurodegenerative disorders (Bjorklund, 1993, Nature 362:414-415; McKay, 1991, Trends Neurosci. 14:338-340). Nevertheless both ethical, as well as practical considerations make fetal tissue a difficult source to deal with. Neuronal stem cells whether fetal or otherwise that are multiplied in vitro cultures provide a source for obtaining the desired quantities of cells for use in the present methods and compositions. Fetal cells can placed into primary culture using, for example, protocols developed by Sabate et al., 1995, Nature Gen. 9:256-260. By way of example but not limitation, the procedure is as follows: Primary cultures of human fetal brain cells can be isolated from human fetuses, obtained from legal abortions after 5 to 12 weeks of gestation. Expulsion can be done by syringe-driven gentle aspiration under echographic control. Fetuses collected in sterile hibernation medium are dissected in a sterile hood under a stereomicroscope. Brains are first removed in toto in hibernation medium containing penicillin G 500 U/ml, streptomycin 100 µg/ml, and fungizon 5 µg/ml. For fetuses of six to eight weeks of age the brain is separated into an anterior (telencephalic vesicles and diencephalon) and a posterior fraction (mesencephalon, pons and cerebellar enlage) and a posterior in toto after careful removal of meninges. For older fetuses, striatal hippocampal, cortical and cerebellar zones expected to contain proliferative cells are visualized under the stereomicroscope and dissected separately. Cells are transferred to either Opti-MEM (Gibco BRL) containing 15% heat-inactivated fetal bovine serum (FBS) (Seromed), or to a defined serum-free medium (DS-FM) with human recombinant bFGF (10 ng/ml, Boehringer), which is a minor modification of the Bottenstein-Sato medium 39 with glucose, 6 g/l, glutamine 2 mM (Gibco BRL), insulin 25 ug/ml (Sigma) transferrin 100 µg/ml (Sigma), sodium selenite 30 nM (Gibco BRL), progesterone 20 nM (Sigma), putrescine 60 nM (Sigma), penicillin G (500 U/ml), streptomycin 100 µg/ml, and fungizon 5 µg/ml. Cells, approximately 40,000 per $cm^2$, are grown at 37° C. in an atmosphere containing 10% $CO_2$ in tissue culture dishes (Falcon or Nunc) coated with gelatin (0.25% wt/vol) followed by Matrigel (Gibco BRL, a basement membrane extract enriched in laminin and containing trace amounts of growth factors diluted one in 20).

5.1.8 Hematopoietic Cells

Cells of the immune system can also be used, including but not limited to lymphocytes, granulocytes, basophils, neutrophils, lymphatic cells, and macrophages. Compositions and methods of the invention comprising such immune cells can have therapeutic use in stimulating or suppressing and immune response or modulating the wound healing process. Mast cells, which can have an effect by increasing histamine supply, can be used with the compositions and methods of the invention to modulate wound healing, inflammation, or allergy related processes. Such cells are obtainable by any method known to those of skill in the art.

In addition to mature hematopoietic cells, hematopoietic stem cells can be used in the present methods and compositions.

Any technique which provides for the isolation, propagation, and maintenance in vitro of hematopoietic stem cells (HSC) can be used in this embodiment of the invention. Techniques by which this can be accomplished include (a) the isolation and establishment of HSC cultures from bone marrow cells isolated from the future host, or a donor, or (b) the use of previously established long-term HSC cultures, which may be allogeneic or xenogeneic. In a particular embodiment of the present invention, human bone marrow cells can be obtained from the posterior iliac crest by needle aspiration (see, e.g., Kodo et al., 1984, J. Clin. Invest. 73:1377-1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608-3612).

Another technique for the isolation of HSC is described by Milner et al., 1994, Blood 83:2057-2062. Bone marrow samples are obtained and are separated by Ficoll-Hypaque density gradient centrifugation, are washed, and stained using two-color indirect immunofluorescent antibody binding and then separated by fluorescence-activated cell sorting (FACS). The cells are labelled simultaneously with IgG antibodies such that $CD34^+$ hematopoietic stem cells, including the immature subset that lacks expression of individual lineage associated antigens, $CD34^+lin^-$, are isolated from the cells collected from marrow.

Where hematopoietic progenitor cells are desired, the presence of hematopoietic progenitor cells and/or their progeny can be detected by commonly known in vitro colony forming assays (e.g., those that detect CFU-GM, BFU-E). As another example, assays for hematopoietic stem cells are also known in the art (e.g., spleen focus forming assays, assays that detect the ability to form progenitors after replating).

5.1.9 Epithelial Cells 5.1.9.1 Stem Cells and Keratinocytes

Epithelial stem cells (ESCs) and keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of precursor cells within the germinal layer, the layer closest to the basal lamina. Precursor cells within the lining of the gut provide for a rapid renewal rate of this tissue. ESCs obtained from the skin or lining of the gut of a patient or donor can be grown in tissue culture (Rheinwald, 1980, Meth. Cell Bio. 21A:229; Pittelkow and Scott, 1986, Mayo Clinic Proc. 61:771).

5.1.9.2 Salivary Epithelial Cells

Culture and growth conditions of non-transformed salivary epithelial cells are described in U.S. Pat. No. 5,462,870 by Chopra.

5.1.9.3 Liver Stem Cells

Liver stem cells can be isolated by methods described in PCT Publication WO 94/08598, dated Apr. 28, 1994.

5.1.9.4 Mature Liver Cells

A collagenase-liver-perfusion method has been described for the isolation of liver cells (hepatocytes) from both rats (Seglen et al., 1976, in Methods in Cell Biology, D. M. Prescott, Ed., Vol. XIII, pp. 29-83, Academic Press, New York) and humans (Butterworth et al., 1989, Cancer Res. 49:1075-84). Suitable culture conditions—including the use of lipid-bound glycosaminoglycan substrates—are taught in U.S. Pat. No. 5,624,839 by Yada et al.

5.1.9.5 Mammary Cells

In one specific embodiment, the epithelial cell population desired for use in the present methods and compositions consists of mammary epithelial cells. These may be isolated according to the method of U.S. Pat. No. 4,423,145.

5.1.9.6 Cervical Cells

Cervical kertinocytes can be grown in culture using a variation of the method used for culturing epidermal keratinocytes (Stanley and Parkinson, 1979, Int. J. Cancer 24:407-414), the method comprising two steps, or primary and secondary culture. The primary culture comprises inoculating the disaggregated epithelium into a tissue culture flask or plate in the presence of serum, growth factors and irradiated or mitomycin C-fed Swiss 3T3 fibroblasts. Secondary cultures are grown on fibroblast support cells.

5.1.9.7 Kidney Stem Cells

Mammalian kidney emerges from the metanephric mesenchyme which induces the uteric bud to undergo a series of morphogenetic movements ultimately forming the mature urinary collecting system (Nigam and Brenner, 1992, Curr. Opin. Nephrol. Huper 1:187-191. The uteric bud, an epithelial outgrowth of the Wolfian duct, contracts and induces condensing adjacent mesenchyme along differentiation pathways of epithelial divergence in early embryonic life. Attempts to study this process in vitro have been reported; metanephros in organ culture can be induced to form tubules using embryonic spinal cord as the inducer. While the specific transducing agents that lead to the induction of metanephric mesenchyme by the uteric bud in vivo or by spinal cord in vitro are not known, cell specific markers show that the differentiation program is induced in progenitor cells (Karp et al., 1994, Dev. Biol. 91:5286-5290).

5.1.9.8 Mature Kidney Cells

The mature kidney consists of a variety of cell types. The isolation or separation of many of these has been described in scientific publications (e.g. Taub et al., 1989, In Vitro Cell Dev. Biol. 25:770-775; Wilson et al., 1985, Am. J. Physiol. 248:F436-F443; Smith and Garcia-Perez et al., 1985., Am. J. Physiol. 248:F1-F7; Pizzonia et al., 1991, In Vitro Cell Dev. Biol. 27A:409-416). Further, methods for culturing primary cultures of mature human kidney have been described (Detrisac et al., 1984, Kidney Int. 25:383-390; States et al., 1984, Biochem. Med. Metab. Biol. 36:151-161; McAteer et al., 1991, J. Tissue Cult. Methods 13:143-148). In one illustrative example, the primary features of culturing adult kidney cells with the characteristics of the proximal renal tubule are the following: progressive enzymatic digestion of an outer cortex tissue fragment; harvesting single cells for culture: growing the cells under high density on a feeder layer of plastic in the presence of serum (Kempson et al., 1989, J. Lab. Clin. Med. 113:285-296).

5.1.9.9 Epithelial Cells of the Lung

Homogeneous lung epithelial cell lines can be isolated and cultured according to the methods of U.S. Pat. No. 5,364,785.

The key to successful culturing of bronchial and tracheal cells is serum-free medium, which prevents terminal differentiation and selects against growth of fibroblasts (LaVeck and Lechner, 1994, in Culture of Animal Cells, third edition, Wiley-Liss Inc. New York, p. 325).

5.1.10 Other Cell Types

There are many other types of cells that can be used in the compositions and methods of the invention. In particular, cells that secrete biologically useful compounds such as compounds useful in wound healing, i.e. thrombin, and cells that will multiply or can be induced to multiply on a polymer fiber matrix such that tissue components or cell layers are produced. Cells that express cell surface proteins GPIb, GPIIb. GPIIIb, (such as, but not limited to those expressed on platelets) P-selectin, glycophorin A, and/or band III (such as, but not limited to, those expressed on red blood cells) can be used in the compositions and methods of the invention. Diseases that involve cells expressing such surface proteins can be treated using the compositions and methods of the invention.

In addition to the types of cells described above, the compositions and methods of the invention can comprise hematopoietic, granulocyte, erythrocyte, eosinophil, epithelial, hepatocyte, osteoprogenitor cells (stem cells that form osteoblasts), osteoblasts and/or myloid cells. The compositions and methods of the invention can also comprise the progenitor cells of all cell types, such as but not limited to, stem cells and fetal cells.

In addition to the methods disclosed or referenced herein, other methods for isolation of cell types form the various tissues and fluids of origin are well known to those of skill in the art.

5.2 Polymers that can be Used in the Compositions and Methods of the Invention The compositions of the invention comprise cells, such as those described in Section 5.1, and polymer fibers. Such polymer fibers can be naturally occurring or synthetic.

Examples of suitable polymers from which fibers can be derived in the practive of the methods and compositions of the invention include cellulose polymers, xanthan, polyaramides, polyamides, polyimides, polyamide/imides, polyamidehydrazides, polyhydrazides, polyimidazoles, polybenzoxazoles, polyester/amide, polyester/imide, polycarbonate/amides, polycarbonate/imides, polysulfone/amides, polysulfone imides, and the like, copolymers and blends thereof. Other suitable classes of polymers from which fibers can be made include polyvinyledene fluorides and polyacrylonitriles. Examples of these polymers include those described in U.S. Pat. Nos. RE 30,351; 4,705,540, 4,717.393; 4,717,394; 4,912,197; 4,838,900; 4,935,490; 4,851,505; 4,880,442; 4,863,496; 4,961,539; and European Patent Application 0 219 878, all of which are incorporated by reference. The polymers can include at least one of either of cellulose polymers, polyamides, polyaramides, polyamide/imides or polyimides. In certain embodiments, the polymers include polyaramides, polyester, urethan and polytetrafluoroethylene. In preferred embodiment of the invention, polymerized N-acetylglucosamine fibers or derivatives thereof are used. In a most preferred embodiment, the polymer fiber is poly-N-acetylglucosamine polymer fiber or a derivative thereof. In certain embodiments, the poly-N-acetylglucosamine polymer fiber has a $\beta$-1→4 configuration. In other embodiments, the poly-N-acetylglucosamine polymer fiber has a $\alpha$-1→4 configuration.

In preferred embodiments, the polymer fibers are composed of proteins. Preferably, such protein fibers are human protein fibers. In specific embodiments of the invention, fibers include, but are not limited to, protein fibers that bind to or interact with a cell surface protein, such as a receptor that interacts with pGlcNAc (e.g. GPIIIa, GPIIb, GPIb as well as Band III, alpha$_{2b}$beta$_3$, and glycophorin A). Methods of identifying fibers that bind to such surface proteins are provided below in Section 5.3. In certain embodiments, the compositions of the invention comprise fibers that are not protein fibers.

Natural polymer fibers can be extracted by means commonly known to one of skill in the art and can be autologous, allogeneic, or xenogeneic to the patient to whom the compositions and methods of the invention are administered.

In a preferred embodiment the polymer fiber is biocompatible and biodegradable. In one embodiment the polymer fiber is biodegradable and degrades within about or within at least 1 day, 2 day, 5 day, 8 day, 12 day, 17 day, 25 day, 30 day, 35 day, 40 day, 45 day, 50 day, 55 day, 60 day, 65 day, 70 day, 75 day, 80 day, 85 day, 90 day, 95 day, or 100 days after administration or implantation into a patient.

In one embodiment, compositions of the invention comprise purified polymer fibers, which may be about or at least 100%, 99.9%, 99.8%, 99.5%, 99%, 98%, 95%, 90%, 80%, 70%, 60%, 50%, 40%, 30%, or 20% pure. In a preferred embodiment, the polymer fibers used in the compositions and methods of the invention are 90-100% purified.

In preferred embodiments, the polymer fibers mixed with cells to form the compositions of the invention are formulated as a slurry. Generally, slurries containing about 0.5-20 mg of fiber per ml of distilled water are used. In preferred embodiments, 10 mg of fiber per ml of distilled water is used. In yet more preferred embodiments, 2-5 mg of fiber per ml of distilled water is used. In specific embodiments, the slurry comprises about 0.5 mg, 1 mg, 2 mg, 3 mg, 4 mg, 5 mg, 6 mg, 7 mg, 8 mg, or 9 mg of fibers per ml of distilled water. In certain aspects of the invention, the fibers may be about 10, 20, 30, 40, 50, 60, 70, 80, 90, 100, 110, 120, or 130 microns in length as determined by electron microscopy. In certain related aspects of the invention, fibers may be about 0.20, 0.25, 0.30, 0.35, 0.40, 0.54, 0.50, 0.55, 0.60, or 0.65 microns in thickness and/or diameter as determined by electron microscopy. In preferred embodiments the fibers are about 0.50 microns in width and range in length from about 20 to 100 microns as determined by electron microscopy, particularly, scanning electron microscopy. In another preferred embodiments the fibers are about 0.50 microns in width and range in length from about 50 to 100 microns as determined by electron microscopy, particularly, scanning electron microscopy. In yet another preferred embodiments the fibers are about 0.50 microns in width and range in length from about 75 to 100 microns as determined by electron microscopy, particularly, scanning electron microscopy.

In certain embodiments, the polymer that interacts with a cell in the composition of the invention is not an ionic synthetic hydrogel such as, but not limited to, crosslinked poly(AAn-acrylic acid) and poly(AAm-dimethylaminoethyl methacrylate). In certain embodiments, the polymer that interacts with a cell in the composition of the invention is not a nonionic synthetic hydrogel, such as, but not limited to, polyacrylamide (PAAm), poly(vinyl alcohol) (PVA), poly (ethylene glycol) (PEG), poly(N-vynl pyrrolidone), poly (methoxy-PEG methacrylate). In certain embodiments, the polymer is not an poly-L-amino acid, such as poly-L-lysine, poly-L-arginine, poly-L-glutamic acid, poly-L-histidine, poly-D-glutamic acid or a mixture thereof. In certain embodiments, the polymer is not an alginate polymer, such as sodium alginate, calcium alginate, strontium alginate, barium alginate, magnesium alginate or any other alginate or a mixture thereof. In certain embodiments, the polymer is not derived from a shell fish, crustaceans, insects, fungi or yeasts. In certain embodiments, the compositions of the invention do not comprise collagen fibers. In certain embodiments, the compositions of the invention do not comprise elastin fibers. In other embodiments these fibers are included in the compositions of the invention.

In one embodiment, the compositions of the invention comprise more than one type of polymer fiber. In such embodiments, the matrix formed by such fibers may have a gradation in concentration of one fiber type over another. In cases where one type of fiber has a different interaction strength with cells, the resulting composition will have a gradation of interaction with the cells. This can result in polymer fiber matrices with greater numbers of cells in certain portions of the matrix, which might have valuable medical uses, particularly in implantation. A gradation of fibers can also be useful if fibers of different charges are used. For instance, in Example 8, deacetylated pGlcNAc bound a greater number of platelets than is acetylated counterpart. Thus, the charge of the fibers can have an effect on the interaction of the cells and fibers.

In embodiments of the invention, the polymer fiber can be any fiber identified by methods described in Section 5.3.

5.2.1 Poly-$\beta$-1→4-N-Acetylglucosamine

Section 2.1 incorporates by reference numerous U.S. Patent documents that describe in detail the structure of poly-$\beta$-1→4-N-acetylglucosamine fibers, any of which can be used in the compositions and methods of the invention.

In preferred embodiments, poly-N-acetylglucosamine polymer fibers are derived from the process of a) culturing a microalgae comprising a cell body and a poly-$\beta$-1→4-N- acetylglucosamine fiber, thereby producing a microalgal cell culture; b) treating the microalgal cell culture of step (a) with a chemical capable of weakening the microalgal cell walls at a concentration that does not disrupt the cell bodies for a sufficient time so that the poly-β-1→4-N-acetylglucosamine fiber is released from the intact cell bodies; and c) segregating the poly-β-1→4-N-acetylglucosamine fibers from the cell bodies, so that the poly-N-acetylglucosamine species is isolated and purified. In related embodiments, the chemical is hydrofluoric acid.

As used herein derivatives of a poly-N-acetylglucosamine polymer include: a semi-crystalline form of a poly-N-acetylglucosamine polymer; a poly-N-acetylglucosamine polymer comprising about 50 to about 150,000 N-acetylglucosamine monosaccharides covalently attached in a β-1→4 conformation, and said polymer has a molecular weight of about 10,000 daltons to about 30 million daltons; a poly-β-1→4-acetylglucosamine polymer comprising about 50 to about 50,000 N-acetylglucosamine monosaccharides covalently attached in a β-1→4 conformation, and said polymer has a molecular weight of about 10,000 daltons to about 10 million daltons; a poly-β-1→4-acetylglucosamine polymer comprises about 50 to about 10,000 N-acetylglucosamine monosaccharides covalently attached in a β-1→4 conformation, and said polymer has a molecular weight of about 10,000 daltons to about 2 million daltons; a poly-β-1→4-acetylglucosamine polymer comprising about 50 to about 4,000 N-acetylglucosamine monosaccharides covalently attached in a β-1→4 conformation, and said polymer has a molecular weight of about 10,000 daltons to about 800,000 daltons; and a semi-crystalline poly-β-1→4 N-acetylglucosamine polymer comprising at least one N-acetylglucosamine monosaccharide that is deacetylated, and wherein at least 40% of said N-acetylglucosamine monosaccharides are acetylated. Derivatives of a poly-β-1→4 N-acetylglucosamine polymer also include compositions that are 100%, 90%, 80%, 70%, 60%, 50%, 40%, 30%, 20%, 10% or less poly-β-1→4 N-acetylglucosamine.

In preferred embodiments, the cell-polymer fibers of the invention comprise poly-N-acetylglucosamine fibers. The poly-N-acetylglucosamine fibers can be produced as about 500 or more acetylglucosamine monosaccharide units in length. The size of the fibers can be reduced by methods such as those described in U.S. patent application Ser. No. 09/781, 182, published as 2002-0019367 on Feb. 14, 2002.

In preferred embodiments, the poly-N-acetylglucosamine polymer fibers mixed with cells to form the compositions of the invention are formulated as a slurry. In certain embodiments, the poly-N-acetylglucosamine slurry comprises about 1 mg, 2 mg, 3 mg, 4 mg, or 5 mg of poly-N-acetylglucosamine fibers per ml of distilled water. In certain aspects of the present invention, the poly-N-acetylglucosamine fibers are about 10, 20, 30, 40, 50, 60, 70, 80, 90, 100, 110, 120, or 130 microns in length. In related aspects, the poly-N-acetylglucosamine fibers are about 0.20, 0.25, 0.30, 0.35, 0.40, 0.54, 0.50, 0.55, 0.60, or 0.65 microns in thickness and/or diameter. In preferred embodiments the fibers are about 0.50 microns in width and range in length from about 20 to 100 microns.

5.3 Identifying Polymers and Cells that can be Used in the Compositions and Methods of the Invention The methods for screening and identifying polymers that can be used in the compositions and methods of the present invention are based on discovery of inventors that cell surface proteins on platelets and red blood cells interact with poly-N-acetylglucosamine polymer fibers. The surface proteins identified by the Inventors form the basis for methods for screening polymer fibers that can be used in the compositions and methods of the invention. In particular, polymer fibers that interact with cell surface proteins such as GPIIIa and GPIb as well as Band III and glycophorin A, and/or polymers that interact with cell surface proteins for those proteins can be used to identify polymers that can be used in the compositions and methods of the invention. Antibodies that are agonists or antagonists of the cell surface proteins such as GPIIIa and GPIb as well as Band III, alpha$_{2b}$beta$_3$, and glycophorin A can be used in to identify polymer fibers that can be used in the compositions and methods of the invention.

In one embodiment of the invention the surface protein or cells that express the surface protein is assayed for its ability to bind the polymer fibers. Binding assays known to those of skill in the art can be used to identify polymer fibers that could potentially be used in the compositions and methods of the invention. Examples of such binding assays are provided in Example Section 10. In other embodiments, competitive binding assays can be utilized to identify polymers that interact with a particular cell surface protein, a cell that expresses the cell surface protein or a general category of cells at least some of which express the cell surface protein. In a specific embodiment, the cells are human cells or chondrocytes. In preferred embodiments, the competitive binding comprises examining the extent of surface protein or cell binding in the presence of pGlcNAc polymer fibers.

The assays of the present invention may be first optimized on a small scale (i.e., in test tubes), and then scaled up for high-throughput assays. The screening assays of the present invention may be carried out on protein, isolated cells and cells in culture. In accordance with the present invention, test polymer fibers which are shown to interact with the surface protein or cells expressing the surface protein in vitro, can further be assayed in vivo, including animal models to determine if the test polymer fibers has the similar effects in vivo and to determine the effects of the test polymer fibers-cell complexes on wound healing and hemostatis.

Binding assays can be used to identify polymer fiber that binds desired surface protein and/or cell types. Binding assays may be performed either as direct binding assays or as competition binding assays. In a direct binding assay, a test polymer fiber is tested for binding to desired surface proteins or cell types. Competition binding assays, on the other hand, assess the ability of a test polymer fiber to compete with known polymer fiber that interacts with cells for binding to the surface protein or cells expressing the surface protein.

In a direct binding assay, the surface protein or cells are contacted with a test polymer fiber under conditions that allow binding of the test polymer fiber. The binding may take place in solution or on a solid surface. Preferably, the test polymer fiber, surface protein or cell is previously labeled for detection. Any detectable compound may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound test polymer fiber, surface protein or cells that have been labeled. Typically, it involves washing with an appropriate buffer. Finally, the presence of a polymer fiber-cell or polymer fiber-surface protein complex is detected.

In a competition binding assay, potential polymer fibers are assayed for their ability to disrupt or enhance the binding of the cells, such as platelets, or cell surface proteins, to a known polymer fiber, such as pGlcNAc, that interacts with said cells or surface protein. Labeled pGlcNAc may be mixed with the surface protein or cells, and placed under conditions in which the interaction between them would normally occur, with and without the addition of the test polymer fiber. The amount of labeled pGlcNAc that binds the surface protein or cells can be compared to the amount bound in the presence or absence of test polymer fiber.

In specific embodiments, natural human fibers, e.g. collagen, elastin, that compete with pGlcNAc for binding to platelets, platelet cell surface proteins, and/or fragments of platelet cell surface proteins know to be involved in the interaction of surface protein or cells and polymer fibers are acceptable for use in the assays of the invention.

In principle, many methods known to those of skill in the art, can be readily adapted in designing the assays of the present invention. Screening methodologies are well known in the art (see e.g., PCT International Publication No. WO 96/34099, published Oct. 31, 1996, which is incorporated by reference herein in its entirety). By these methods, one skilled in the art can identify potential polymer fibers suitable for use in the compositions and methods of the invention.

Once polymer fibers that interact with surface protein or cells that express the surface protein are identified, they can be further tested to determine if gels are formed using different ratios of cells to polymers. The experiments presented in Example Section 6 provide an example of such methods.

Once polymer fibers that bind surface protein or cells that express the surface protein are identified by the methods described herein, the fibers can be further tested to determine if they cause activation of a cell that expresses the surface protein. Assays can be used, such as those described in Example Section 9, employing electron microscopy to visualize morphological changes in the cells. For example, platelets can be used to examine the formation of pseudopodia and their interaction with the identified fiber. Polymer fibers identified by this additional test would be particularly useful in preservative and therapeutic embodiments of the invention.

5.3.1 Screening for Compounds that Competitively Inhibit the Binding of Polymer Fibers to Cell Surface Proteins The present invention encompasses the identification of novel reagents that compete with the binding of polymer fibers, e.g., pGlcNAc fibers, to their binding partners, e.g., cell surface receptors. Such reagents can be utilized in a manner similar to the polymer fibers themselves, for example a reagent that disrupts the interaction between pGlcNAc and platelet cell surface proteins is a candidate therapeutic agent for promoting hemostasis or wound healing. Below are exemplary methods for the identification of such compounds.

The basic principle of the assay systems used to identify cell-polymer fiber inhibitors involves preparing a reaction mixture containing at least the polymer fiber-binding portion of the cell type of interest, e.g. cell surface proteins described in Section 5.1.3, and the polymer fiber under conditions and for a time sufficient to allow the two to interact and bind, thus forming a complex. In order to test a compound for its ability to compete with the fiber for binding to a surface protein or cell that expresses a surface protein, the reaction mixture is prepared in the presence and absence of the test compound. The test compound can be initially included in the reaction mixture, or can be added at a time subsequent to the addition of the cells or cell components that bind the polymer fiber. Control reaction mixtures are incubated without the test compound or with a placebo. The formation of any complexes between the cells or cell components that bind the polymer fiber and the polymer fiber is then detected. In a preferred embodiment, the cell component is a surface protein or fiber-binding portion thereof. The formation of a complex between the cell or cell component and the fiber in the control reaction, but not in the reaction mixture containing the test compound, indicates that the compound interferes with the surface protein- or cell-polymer fiber interaction.

The assay for compounds that competitively inhibit the interaction of cells and polymer fibers can be conducted in a heterogeneous or homogeneous format. Heterogeneous assays involve anchoring either the cell or cell component that binds to the polymer fiber (e.g., the surface protein that interacts with the polymer fiber) or polymer fiber onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the surface protein or cell and polymer fiber, e.g., by competition, can be identified by conducting the reaction in the presence of the test substance; i.e., by adding the test substance to the reaction mixture prior to or simultaneously with the cell or cell component and polymer fiber. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the cell or the cell component (e.g., surface protein), or the polymer fiber, is anchored onto a solid surface, while the non-anchored species is labeled, either directly or indirectly. In practice, microtiter plates are conveniently utilized. The anchored species can be immobilized by non-covalent or covalent attachments. Non-covalent attachment can be accomplished simply by coating the solid surface with the cell, surface protein or a solution of polymer fiber and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the surface protein or cells and polymer fibers is prepared in which either the surface protein or cells that express the surface protein and polymer fibers are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt the surface protein- or cell-polymer fiber interaction can be identified.

In a particular embodiment, a surface protein can be prepared for immobilization using recombinant DNA techniques known to those of skill in the art. For example, the surface protein can be fused to a glutathione-S-transferase (GST) gene using a fusion vector, such as pGEX-5X-1, in such a manner that its binding activity is maintained in the resulting fusion protein. The binding partner (i.e., the polymer fiber) can be purified and used to raise a monoclonal antibody, using methods routinely practiced in the art and described above. This antibody can be labeled with the radioactive isotope $^{125}$I, for example, by methods routinely practiced in the art. In a heterogeneous assay, the GST-surface protein can be anchored to glutathione-agarose beads. The polymer fiber, respectively, can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the surface protein and polymer fiber can be detected by measuring the amount of radioactivity that remains associated with the glutathione-agarose beads. A successful inhibition of the interaction by the test compound will result in a decrease in measured radioactivity.

Alternatively, the GST-surface protein and its binding partner (i.e., the polymer fiber) can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the surface protein-polymer fiber interaction can be detected by adding the labeled antibody and measuring the radioactivity associated with the beads.

5.3.1.1 Cell-Based Assays

Cell populations which endogenously or recombinantly express cell surface proteins that bind polymer fibers can be utilized to identify or validate potential cell-polymer fiber inhibitors.

In order to recombinantly express a cell surface protein that binds polymer fibers, the open reading frame of the gene encoding the surface protein can be ligated to a regulatory sequence which is capable of driving gene expression in the cell type of interest. Such regulatory regions will be well known to those of skill in the art, and can be utilized in the absence of undue experimentation. Transfection of the cell surface protein expression construct can be accomplished by utilizing standard techniques. See, for example, Ausubel, 1989, supra. Transfected cells should be evaluated for the presence of the recombinant target gene sequences, for expression and accumulation of target gene mRNA, and for the presence of recombinant target gene protein production.

5.4 Compositions of the Invention

The compositions of the invention can comprise various ratios of cells to polymer fibers as well as other agents that act as preservatives, or biologically active agents. The ratio desired may vary depending on the formulation and use of the composition. The compositions of the invention can be comprised of about 1%, 2%, 3%, 4%, 5%, 6%, 7%, 8%, 9%, 10%, 15%, 20%, 25%, 30%, 40%, 50%, 60%, 70%, 80%, 90% or more cells. In preferred embodiments, the compositions comprise 40%, 50%, 60%, 70%, 80%, 90% or more cells. In other preferred embodiments, the compositions comprise 20%, 25%, 30%, 40%, 50%, 60% or more cells. In other preferred embodiments, the compositions comprise 1%, 2%, 3%, 4%, 5%, 6%, 7%, 8%, 9%, 10%, 15%, 20%, 25%, 30%, 40%, or more cells. In preferred embodiments, the ratio of quantity of cells to quantity of polymers is 1:1. The quantity of cells is the quantity of isolated cells. For example, with platelets, the quantity of cells can be the standard forms of isolated platelets available, such as the quantity of platelet rich plasma processed from a citrate-phosphate-dextrose solution (CDP) standard poly-vinyl blood storage bag. In other embodiments, the platelets may be further purified to not contain plasma. In other embodiments, the quantity of cells is the maximum quantity of a given cell type that can be contained in a defined volume, such as but not limited to, microliter, milliliter, or liter.

In preferred embodiments, the compositions of the invention comprise calcium. The calcium may be added to the composition in the form of a salt or salt solution. The calcium solution is preferably a solution of 1-30% $CaCl_2$. In specific embodiments, the calcium solution is a solution of 5-25%, 5-20%, 5-15%, 7.5-25%, 7.5-20%, most preferably approximately 7.5-15% $CaCl_2$, and is most preferrably a solution of approximately 10% $CaCl_2$. Other salts of calcium (e.g., $CaSO_4$) can be substituted, as can $NaCl_2$ salt solutions. The calcium is preferably in the form of a 10% $CaCl_2$ solution. In specific embodiments the $CaCl_2$ solution is approximately 1, 2, 3, 4, 5, 6, 7, 8, 9, 10, 12, 14, 16, 18, 20, 22, 24, 26, or 30 percent $CaCl_2$ solution. In other embodiments the composition comprises a calcium salt selected from the group consisting of calcium gluconate, calcium lactate, calcium phosphate, calcium sulfonate, calcium carbonate, and calcium oxalate.

In preferred embodiments, the compositions of the invention comprise magnesium, in addition to or in place of calcium. In preferred embodiments, the composition comprises at least 0.025 M magnesium solution (e.g., $MgCl_2$, $MgSO_4$ solution) per 1 mg of fibers.

In certain embodiments, the number of cells in a composition of the invention is at least 100, 200, 300, 400, 500, 700, 1,000, 5,000, 10,000, 25,000, 50,000, or 100,000 cells. In preferred embodiments, the number of cells is at least 100, 200, 300, 400, 500 cells. In other preferred embodiments, the number of cells is at least 300, 400, 500, 700, 1,000 cells. In yet other preferred embodiments, the number of cells is at least 700, 1,000, 5,000, 10,000 cells. In yet other preferred embodiments, the number of cells is at least 5,000, 10,000, 25,000, 50,000, or 100,000 cells. In yet other preferred embodiments, the number of cells is at least 50,000, or 100,000 cells. In other embodiments, the number of cells is at least $1\times10^6$, $5\times10^6$, $1\times10^7$, $5\times10^7$, $1\times10^8$, $5\times10^8$ or more cells per mg of polymer fiber. In preferred embodiments, the number of cells is at least $1\times10^6$, $5\times10^6$, or $1\times10^7$ or more cells per mg of polymer fiber. In other preferred embodiments, the number of cells is at least $1\times10^7$, $5\times10^7$, $1\times10^8$ or more cells per mg of polymer fiber. In other preferred embodiments, the number of cells is at least $5\times10^7$, $1\times10^8$, $5\times10^8$ or more cells per mg of polymer fiber.

Standard units of blood (450 ml) are typically collected with 63 ml CPD polyvinyl-chloride bags. In certain embodiments, the quantity of platelets used in the compositions of the invention is the amount of cells or platelet rich plasma (PRP) that can be isolated from a CPD. In a preferred embodiment, the composition comprises 0.125 ml of calcium chloride and 5 ml of pGlcNAc slurry (1 mg/ml distilled $H_2O$) to 5 ml of PRP. In a another preferred embodiment, the composition comprises 0.125 ml of calcium chloride and 5 ml of pGlcNAc slurry (1 mg/ml distilled $H_2O$) to a 5 ml aliquot of PRP.

The interaction of the cells and the polymer fibers can be through electric charge interaction, binding (covalent or non-covalent), or adhesive. In preferred embodiments, the interaction is binding of cell surface proteins to components of the polymer fibers. The interaction may also involve chemical signaling. For example, in the case of platelets and pGlcNAc, the platelets extend pseudopodia to contact the pGlcNAc fibers (FIG. 3). Such interactions are likely under the control of detection of chemical signals by the cells and/or electric charge interactions.

In certain embodiments, the composition of the invention is adhesive, in that it will form an association with for example the human skin or the surface of an internal organ. In other embodiments, the composition is not adhesive.

In certain embodiments, the compositions of the invention are frozen (e.g., at about 0° C. to −80° C., more preferably at about −10° C. to −40° C. Such frozen compositions can be stored for later use. In other embodiments, the compositions are stored at about 1-25° C. In specific embodiments, the composition is stored at about 4° C. or 22° C.

In the compositions of the invention, each cell can have one or a few points of contact with the polymer fiber. In certain embodiments, the individual cells are not encapsulated by the polymer fibers. The polymer fibers of the invention form a matrix that allows for absorption of cells and a more open interaction of cells and polymer fibers. This differs distinctly from a cell encapsulated with a polymer fiber for the purpose of delivery of the cell. In such instances the polymer fiber acts as a coating not as an open matrix that allows for interaction of cells with polymer fibers and/or interactions between the cells that are interacting with the fibers, e.g., platelets associated with poly-β-1→4-N-acetylglucosamine polymers, wherein said platelets interact with and aggregate with each other.

Mixtures of cell populations or types, such as, but not limited to, platelets and cells of the immune system can be combined with polymers in producing the compositions of the invention. In such mixtures, only one cell type need be identified as capable of interacting with the polymer. Such mixtures of cell types can be naturally occurring and mixed with proteins and other non-cellular components, as is the case in blood, or the mixtures of cell types can be made by isolating and purifying cell types and then mixing the populations of cells in desired ratios which may or may not occur naturally. Such mixtures may also include naturally occurring or synthetic additives such as those described in Section 5.4.3.

There are many reasons why one would want to control number of cells in a composition of the invention. For example, in certain embodiments, one might combine a certain number of platelets with a pGlcNAc formulation without saturating the pGlcNAc polymer fiber matrix. The resulting composition could be frozen for later use, or used immediately. Additional cells could be added immediately before applying the composition. In other embodiments the composition can be applied so that cells or fluid from the body of the patient interact with the pGlcNAc fibers not already bound by platelets or are absorbed by the polymer fiber matrix.

5.4.1 Formulations of the Compositions of the Invention

The matrix of polymers and associated cells of the compositions of the invention can be three-dimensional and can be in the form of gel, membrane, woven or non-woven tissue or fabric, sponges, guide channels, gauzes, microshperes, granules, or formulated to replicate the density, porousness or shape of a natural portion of a mammal.

The composition can be formulated as a gel, solid, liquid, sponge, foam, spray, emulsion, suspension, solution, string, microbead, microsphere, or microfibril. The pharmaceutical compositions of the invention can include a pharmaceutically acceptable carrier, a neutral liquid, neutral gel or neutral solid. In certain preferred embodiments, the composition is formulated as a barrier, membrane, or film or the composition has been added to a barrier, membrane, or film, such as a backing. A barrier, membrane, or film can be supplied in a variety of standard sizes, which can be further cut and sized to the area being treated. The barrier, membrane, or film can be a conventional bandage or gauze to which the composition of the invention is added or coated on, prior to application to the patient. Alternatively, the composition can be formulated as a barrier, membrane, or film made out of strings, microbeads, microspheres, or microfibrils, or the composition can be formulated as a barrier-forming mat.

In addition, by varying the ratio of the components in said biodegradable matrices, the surgical handling properties of the cell matrix can be adjusted in a range from a dimensionally stable matrix, to a moldable putty-like consistency to a pliable gel or slurry, to a powder or to an injectable fluid.

5.4.1.1 Gels

In preferred embodiments, the composition of the invention is formulated as a gel. The gel can be of varying viscosity. For embodiments where the gel is applied to a bandage to treat a topical wound, a low viscosity is desired. For injectable gels, higher viscosity may be desired if the composition is intended to remain in a location of the body rather than dissipate rapidly. Viscosity is the quantity that describes a fluid's resistance to flow measured in centipoise (cP). While the range of viscosity is a continuum. For example, as a frame of reference, not as a limitation of the meaning of viscosity, the viscosity values of about 1-4 cP generally are typified by fluid compositions. Viscosity values of about 5-14 cP generally are typified by gel-like compositions, while viscosity values of 15-20 cP are relatively hard compositions such as plastics. The viscosity of cell cytoplasm is about 11 cP. Viscosity can be measured with, for example, a Saybolt International B.V. (Vlaardingen, The Netherlands). One skilled in the art can also use other measurement techniques and devices common in the art.

5.4.1.2 Sponges

In other preferred embodiments, the composition of the invention is formulated as a sponge. When the composition is a sponge, a predetermined amount of a cell suspension can be transferred on top of a sponge matrix, and the cell suspension can be absorbed. Therapeutic pGlcNAc-platelet conjugates typically comprise a polymer fiber matrix with cells associated throughout the matrix. This allows for greater cell numbers to interact with fibers and the matrix is able to absorb large numbers of cells.

5.4.1.3 Membranes

In certain embodiments of the invention, the composition of the invention is formulated as a membrane. The membranes may be porous or relatively continuous. In preferred embodiments the membranes are made of woven polymer fibers that have been combined with cells to form the composition of the invention. Such membranes are particularly useful in treatment of wounds on the skin surface or on the surface or on the surface of internal organs or the lining of body cavities.

5.4.1.4 Sutures

In certain embodiments of the invention, sutures formulated from a polymer fiber known to interact with cells can be combined with cells to increase biocompatability of sutures. For example a suture made of pGlcNAc fibers can be contacted to platelets to form a coating of cells. Such sutures would be biodegradable, promote wound healing, enhance biocompatable in comparison to suture alone, and would decrease immune response, particularly if the cells applied were of autologous origin.

5.4.2 Pharmaceutical Compositions

The pharmaceutical compositions of the invention can vary widely depending on the formulation of the composition and the intended use.

In certain embodiments, the composition of the invention is formulated as a sponge or another three dimensional formulation. These embodiments have particular pharmaceutical application in the design of time release therapies for implantation, as cells and agents produced by the cells of the composition must diffuse through the matrix, and the internal portions of the formulation will not biodegrade as rapidly as the outer exposed portions.

The composition may be formulated as a barrier-forming material that forms a barrier to blood. The composition can coat, be added to, or integrated into a barrier-forming material that forms a barrier to blood. In one embodiment, the pharmaceutical composition comprises a patch made of barrier-forming materials. In one embodiment, the pharmaceutical composition comprises a gauze coated with the composition of the invention. In certain embodiments, the pharmaceutical compositions comprise a barrier-forming material coated with the composition of the invention, wherein the barrier-forming material contains an adhesive so that the material can be adhere to a patient's skin surface. Alternatively, the composition can lack barrier-forming materials.

The pharmaceutical compositions of the invention can include a backing. For example, if the composition is formulated as a patch, a backing can be adhered to the patch. The backing can be coated or embedded with any adhesive compound so that areas of the backing that contact the skin will adhere the backing and the attached composition of the invention to the skin surface of the patient. The type of adhesive used can be any type of medically acceptable adhesive. Such backings can be made of natural polymers or synthetic materials. Natural polymers from which the backing can be made include but are not limited to cellulose and xylan. Synthetic materials from which the backing can be made include but are not limited to polyurethane, Teflon, Dacron, stainless steel mesh screen, and a polyester woven fabric. Preferably the backing and adhesive are porous to areas which contact the skin to allow diffusion of oxygen. The backing can also serve as a surface upon which manual compression can be applied.

The pharmaceutical compositions of the invention can also comprise wound-healing and/or pain-reducing agents. Such agents include anti-inflamatory agents, both steroidal and non-steroidal, such as but not limited to agents which inhibit leukocyte migration into the area of the breach or puncture in the blood vessel (i.e., silver sulfadiazinem acetylsalicylic acid, indomethacin, and Nafazatrom), anti-histamines (i.e., pyrilamine, chlorpheniramine, tetraydrozoline, antazoline, cortisone, hydrocortisone, beta-methasone, dexamethasone, fluocortolone, prednisolone, triamcinolone, indomethacin, and sulindac, its salts and its corresponding sulfide); agents which inhibit free radical formation (i.e., superoxide dismutase (SOD), catalase, glutathione peroxidase, b-carotene, ascorbic acid, transferring, ferritin, ceruloplasmin, and desferrioxamine alpha-tocophenol); and bacteriostatic or bacteriocidal agents (i.e., cefoxitin, n-formamidoyl thienamycin, tetra cyclines, chloramphenicol, neomycin, gramicidin, bacitracin, sulfonamides, gentamycin, kanamycin, amikacin, sisomicin, tobramycin, norfloxican, nitrofurazones, and the combination of fluoroalanin/pentizidone).

The pharmaceutical compositions of the invention can also comprise one or more coagulants such as, but not limited to, alpha-2-antiplasmin, alpha-1-antitrypsin, alpha-2-macroglobulin, aminohexanoic acid, aprotinin, a source of Calcium ions, calcium alginate, calcium-sodium alginate, casein kinase II, chitin, chitosan, collagen, cyanoacrylates, epsilon-aminocaproic acid, Factor XIII, fibrin, fibrin glue, fibrinogen, fibronectin, gelatin, living platelets, metha crylates, PAI-1, PAI-2, plasmin activator inhibitor, plasminogen, platelet agonists, protamine sulfate, prothrombin, an RGD peptide, sphingosine, a sphingosine derivative, thrombin, thromboplastin, or tranexamic acid. The compositions can also be combined where desired with other active agents, including radiation or other antiviral or antineoplastic therapy.

The pharmaceutical compositions of the invention can also comprise one or more vasoconstrictors such as, but not limited to, endothelin-1, epinephrine, phenylephrine, serotonin, thromboxane, norepinephrine, prostaglandin, methergine, oxytocin, isopreland U-46619.

The pharmaceutical compositions of the invention can also comprise serotonin, catecholamines, factor V, Von Willebrand factor 8, or thromboxane A2.

The pharmaceutical compositions of the invention can also include a pharmaceutically acceptable carrier such as, but not limited to, conventional excipients, i.e., pharmaceutically acceptable organic or inorganic carrier substances suitable for parenteral, enteral (e.g., oral or inhalation) or topical application which do not deleteriously react with the compositions of the invention. Suitable pharmaceutically acceptable carriers include but are not limited to water, salt, sugar solutions, etc. The pharmaceutical preparations can be sterilized and if desired mixed with auxiliary agents.

5.4.3 Additive Agents that can be Used in the Compositions of the Invention

Numerous agents can be added to the compositions of the invention. Such agents can function as preservatives, antifreeze agents, biologically active agents that exert an effect on other cells, and/or agents that modulate an immune response.

For compositions and methods of the invention comprising red blood cells, additive solutions including but not limited to Adsol™ (AS-1), Nutricel™ (AS-3), Optisol™ (AS-5), and Erythro-Sol™ can be added to extend the storage of compositions of the invention comprising red blood cells. Other additive agents that can be used to extend the storage of compositions of the invention comprising red blood cells include but are not limited to acid-citrate-dextrose (ACD), citrate-phosphate-dextrose solution (CPD), CPD with adenine (CPDA-1), and EAS-61 as described in U.S. Pat. No. 6,150,085. Typically, the additive agents that extend storage of red blood cells are effective at 4° C. or 22° C.

For compositions and methods of the invention comprising platelets, additive solutions can be used, including but not limited to, dimethylsulfoxide (Valeri et al., 1974, Blood. Vol. 43, No. 1), platelet activation inhibitors such as prostoglandin E and theophylline (Vox Sang 1991, 60: 105-112), and L-carnitine, which can also be used for whole blood as described in U.S. Pat. No. 6,482,585.

Growth factors are agents that can be added to the compositions of the invention to induce cells of the composition to produce a desired compound, or multiply and form tissue layers. The growth factors can also be added to the composition to enhance the effect of the composition of surrounding cells and tissues once the composition has been administered. Nerve growth factor (NGF); Platelet-derived growth factor (PDGF); RBPJκ binding domain of Notch (RAM); retinoic acid receptor (RAR); stem cell factor, also known as the c-kit ligand or mast cell growth factor (SCF); transforming growth factor-β(TGF-β) thrombopoietin (Tpo). The growth factors that can be utilized in the compositions and methods of the invention can be obtained commercially, produced by recombinant expression, or chemically synthesized. For example, ATRA, BDNF (human), CNTF (human and rat), EGF (human), FGF-1 (human and bovine), FGF-2 (human and bovine), FGF-7 (human), Flt-3L (human), GDNF (human and rat), HGF (human), IGF-1 (human), IL-6 (human and mouse), IL-11 (human), NGF (murine), PDGF (human AA, AB, and BB isoforms), SCF (human), TGF-β(human), Tpo (human and murine) can be purchased from Sigma (St. Louis, Mo.). EGF (human and murine), FGF-1 (human), FGF-2 (human), GM-CSF (human and murine), IGF-I (human), IL-6 (human and murine), IL-7 (human and murine), NGF (murine), PDGF (human AA, AB, and BB isoforms), SCF (human) and TGF-β (human) can be purchased from Life Technologies, Inc. (Rockville, Md.). Transforming growth factor-beta. ("TGF-beta.") refers to a growing family of related dimeric proteins which regulate the growth and differentiation of many cell types (Barnard et al., 1990, Biochem. Biophys. Acta. 1032:79-87; Massague, 1990, Annu. Rev. Cell. Biol. 6:597-619; Roberts and Sporn, 1990, in: M. B. Sporn and A. B. Roberts (eds.), Peptide Growth Factors and Their Receptors I, Springer-Verlag, Berlin, pp. 419-472).

In some embodiments of the invention, the composition does comprises cytokines. The cytokines can be selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, and TGF-β. In certain embodiments, the compositions of the invention do not comprise one or more cytokines.

5.5 Methods for Production of the Compositions of the Invention

The compositions of the invention are primarily produced by mixing cells and a suspension of polymer fibers and allowing the two components to interact to form a gel. In certain embodiments, calcium is necessary for the gel to form. Preferably about 0.025% calcium is added. In other embodiments magnesium is added to form a gel.

The compositions of the invention formulated as gels can be produced in situ, i.e., mixed in a syringe as they are administered to a patient, produced immediately prior to application and then applied to a patient, or produced prior to application and stored for use at a later time. In embodiments where the compositions of the invention are produced in situ, the components of the composition could be combined in a syringe to form the composition of the invention as they are administered to a patient. For example, a composition made by mixing platelets, pGlcNAc slurry and a calcium chloride solution can be made in a two-compartment syringe as it is administered to a patient. A number of different permutations can be used, such as placing the platelets and pGlcNAc slurry in one compartment of the syringe and the calcium chloride solution in the other, then mixing the contents of the two compartments prior or concurrently with administration. Alternatively, the platelets and calcium chloride solution can be placed in one compartment of the syringe and the pGlcNAc slurry in the other, then the contents of the two compartments mixed prior or concurrently with administration.

If the product is to be stored for long periods of time, i.e. greater than about 1, 2, 3, 4, 5, 6, 7, 8 or 9 hours, the composition of the invention can be frozen and thawed or stored at about 4, 10, 15, 20, or 22° C. for later use. One skilled in the art can use cryopreservation techniques such as those described in U.S. Pat. Nos. 6,519,954 and 6,372,423 for this purpose.

5.6 Methods for Treatment Using the Compositions of the Invention

The present invention provides methods of treatment using a composition of the invention. The compositions of the invention can be used as biocompatible and, optionally, biologically active, barrier materials or implants to supplement damaged or injured tissues. Thus, desired cells can be complexed with a polymer fiber matrix formulated as a sponge or gel, or other formulations, for the purposes of implantation.

For example, insulin producing beta cells can be implanted in a patient using a polymer fiber-cell matrix. The beta cells themselves may or may not interact with the polymer fiber, however, the matrix comprises cells that do. The cells in addition to beta cells can be cells such as platelets or other cells that produce growth factors or hormones that facilitate the establishment of implanted beta cells. Chondrocytes are another example of cells that one skilled in the art might desire to implant in a patient. The compositions of the inventions can include polymer fiber matrixes that include chondrocytes. In embodiments of the invention, the condrocytes interact with the polymer fibers. In such embodiments other cells may also be present in the matirx. In other embodiments, the condrocytes do not interact with the fibers, in such cases other cells that do interact with the polymer fibers are present in the composition. Cells that produce substances, such as growth factors and hormones, that induce chondrocytes to multiply or produce cartilage in the matrix are desirable in such embodiments.

In one embodiment of the invention, a composition of the invention is used to supplement or replace tissues during regeneration and repair processes. In another embodiment, a composition of the invention is used to treat degenerative or traumatic disorders of the sensory epithelium of the inner ear.

In yet another embodiment of the invention, a composition of the invention comprising a cell-fiber polymer matrix is used to supplant or replace tissues compromised by disease, for example liver tissue, lung tissue, pancreatic tissue, skin, cartilage, bone, hematopoietic cells, intestine, heart, kidney, etc. A composition of the invention comprising a liver cell-fiber polymer matrix can be transplanted into patients whose livers have been compromised or destroyed by diseases such as hepatitis, cirrhosis or toxic medications.

Compositions of the invention comprising lung cell-fiber polymer matrices can be used to supplement the lung function of patients whose own lungs are not able to provide sufficient function after the removal of tumors of the lung; similarly, compositions of the invention comprising intestinal cells can be used to replace portions of the intestines removed after cancer surgery. Compositions of the invention comprising cartilage-fiber polymer matrices are suitable for the reparation of ear and nose defects in children. Compositions of the invention comprising dermal cell-fiber polymer matrices can be used for burn patients, e.g., as artificial skin. Implantation of compositions of the invention comprising pancreatic cell-fiber matrices is suitable after pancreas removal (e.g. after cancer surgery) or for treatment of severe diabetes. In the latter situation, compositions comprising pancreatic cells that have been genetically engineered to express insulin are preferably used. Compositions comprising chondrocytes or other bone tissue can be grafted or implanted to replace or supplement missing bone. Bone grafts are often used by the body as scaffolds in the formation of new bone tissue. Compositions of the invention comprising thyroid cell-fiber polymer matrices can be transplanted into a patient in whom the functional cells of the thyroid are destroyed, e.g. by Hashimoto's thyroiditis. Hematopoietic or immune cells-containing matrices of the invention can be administered to patients who are immunocompromised or immunosuppressed or have an immune deficiency, for example as a result of Acquired Immune Deficiency Syndrome or exposure to radiation or chemotherapy regimens for the treatment of cancer, such that the cells in the administered matrices perform a needed immune or hematopoietic function.

Where a composition of the invention comprises cells that are non-autologous to the patient to whom the composition administered to in whom the composition is implanted, the composition is used preferably in conjunction with a method of suppressing rejection. In certain embodiments, the composition comprises cells that produce and excrete compounds needed by the patient.

It will be understood to those skilled in the art that the above embodiments are merely exemplary; the composition of the invention may be applied to any disease that requires cell or tissue supplementation.

In certain embodiments, the polymer fiber-cell matrix compositions of the invention that are implanted comprise cells that produce compounds that are effective in treating infectious disease or cancer. In other embodiments, the cells are engineered to produce such compounds.

5.6.1 Coating Implants

The compositions of the invention comprising cell-fiber polymer matrices can be used to coat synthetic implants or prosthetic devices for the purpose of improving the biocompatibility of the implant or imparting biological activity to the implant. Prosthetic devices are often used in surgical applications, for example in reconstructive or joint replacement surgery. The material of choice for prosthetic implants is metal, usually titanium, although other materials, e.g. ceramics, may be used. Prosthetic devices are often anchored at the site of implantation with synthetic cements. In recent times, implants have been coated with thin, porous materials to allow the surrounding tissue to grow into the porous layers encapsulating the implants. However, it is more desirable to encapsulate such prosthetic implants with cell types found at the site of implantation, which would promote more successful anchoring and integration. Thus, in one aspect of the invention, the compositions of the invention comprising cell-fiber polymer matrices are used to coat prosthetic devices for implantation into humans. The prosthetic devices to be coated by the compositions include but are not limited to joint components (for example for knees, shoulders and hips), heart valve replacements, spinal disc implants, ossicular bone replacements and plates/rods for bone (e.g. femur, tibia) remodeling. In a preferred embodiment, the cell-fiber polymer matrices used to coat the prosthetic implants are autologous to the individual.

5.6.2 Methods of Transplantation

The compositions of the invention comprising cell-fiber polymer matrices can be transplanted into a patient for the treatment of disease or injury or for gene therapy by any method known in the art which is appropriate for the type of cells in the matrix. Matrices comprising hematopoietic cells can be transplanted intravenously, as can liver cells which will locate to the liver. Matrices comprising neural cells can be transplanted directly into the brain at the site of injury or disease. Matrices comprising skin cells can be used for grafts, to treat burns, etc. Matrices comprising mesenchymal cells can be used to coat prosthetic devices prior to implantation (as described supra).

Methods of introduction include but are not limited to intradermal, intramuscular, intraperitoneal, intravenous, subcutaneous, intranasal, and epidural routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic but is preferably local. In addition, it may be desirable to introduce the compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the compositions of the invention locally to the area in need of treatment; this may be achieved by, for example, and not by way of limitation, local infusion during surgery, topical application, e.g., in conjunction with a wound dressing after surgery, by injection, by means of a catheter, as an implant, or by means of an implant, said implant being of a porous, non-porous, or gelatinous material, including membranes, such as sialastic membranes, or fibers.

In a preferred embodiment, the cells in the cell-polymer fiber matrices of the invention autologous. In another embodiment, the cells in the cell-polymer fiber matrices of the invention are non-autologous.

The amount of the cell-polymer fiber matrices of the invention to be implanted which will be effective in the treatment of a particular disorder or condition will depend on the nature of the disorder or condition, and can be determined by standard clinical techniques. The precise amount to be employed in the formulation will also depend on the route of administration, and the seriousness of the disease or disorder (e.g., the extent of tissue injury), and should be decided according to the judgment of the practitioner and each patient's circumstances.

5.6.3 Wound Healing and Hemostasis

The present invention provides methods for treatment of wounds that are skin wounds or wounds to internal organs. Such wounds typically disrupt blood vessels. In an embodiment of the invention, the wound is caused by an object such as a bullet, knife, or surgical instrument. In a preferred embodiment the object that causes the wound is a catheter. In yet another preferred embodiment the wound is the result of a cardiac catheterization procedure. Arteries that have been breached or punctured by a catheter may be treated by the present methods and compositions include, but are not limited to, the femoral, radial, brachial, and axillary arteries. Veins that have been breached or punctured by a catheter that can be treated by the present methods and compositions include, but are not limited to, the femoral, internal jugular, and subclavian veins.

Generally, a catherterization wound is caused by a smaller diameter catheter. Examples of smaller diameter catheters include catheters ranging from 4 F to 6 F in size (F=French Units, where 1 F is equal to 0.33 mm). In another embodiment of the invention, the wound may be caused by a larger-diameter catheter ranging in size from 7 F to 11.5 F (Sanborn et al., 1993, Journal of the American College of Cardiology. 22(5): 1273-1279). Preferably, the artery is larger than a catheter between 6 F and 8 F in size. In such embodiments where a wound is the result of catheterization, the methods and compositions of the invention can be used to treat wounds cause by various types of catheters, including but not limited to a Swan-Ganz catheter, a Sones catheter, and a pigtail catheter (Glade et al., 2002, Emedicine Journal, 3(3):1-13).

In certain embodiments, catheters are inserted perpendicular to the skin surface. In other embodiments, a catheter is inserted at an angle that is 20°-40° to the skin surface.

In certain embodiments, the cell-polymer fiber compositions of the invention may be used in periodontal surgery, maxillofacial surgery, oral surgery or implant surgery, such as, but not limited to, sinus grafting to achieve wound healing or hemostasis. In related embodiments, application of the compositions of the invention in such surgeries enhances maturation of the soft (connective and gingival) tissues. In other related embodiments, application of the compositions of the invention results in enhancement of bone grafts.

In one embodiment of the invention, the cell-polymer fiber compositions of the invention are used to enhance a bone graft. In such embodiments, the compositions of the invention can be applied to the graft site.

In related embodiments, the cell-polymer fiber compositions of the invention comprise platelet rich plasma. In related embodiments, the cell-polymer fiber compositions of the invention comprise one or more growth factors.

The present methods can be used to treat wounds in veins or arteries in any mammal including but not limited to a human, dog, horse, cat, rabbit, rat, mouse, pig, cow, monkey or sheep. Preferably the patient is a human.

5.6.3.1 Compositions and Methods for Topical Treatment of Wounds

In certain embodiments, the cell-polymer fiber compositions of the invention may be used to treat tissue wounds.

According to one aspect of the invention, a method for treating a puncture in a vein or artery resulting from a cardiac catheterization procedure in a patient, comprises a) applying topically to the patient's skin over a catheter exit site an effective amount of the composition of the invention, wherein the catheter exit site is contiguous with the catheter puncture in the vein or artery by 1-10 cm; and concurrently b) applying compression to the punctured vein or artery, wherein a cessation or reduction of blood flow out of the breach or puncture in the vein or artery is achieved in 30%-50% less time than applying compression in conjunction with a topical barrier-forming material without said composition of the invention.

According to another aspect of the invention, a method for treating a puncture in a femoral artery resulting from a cardiac catheterization procedure in a patient comprises a) applying topically to the patient's skin over a catheter exit site an effective amount of the composition of the invention, wherein the catheter exit site is contiguous with the catheter puncture in the femoral artery by 1-10 cm; and concurrently b) applying compression to the punctured vein or artery, wherein a cessation or reduction of blood flow out of the breach or puncture in the femoral artery is achieved in 30%-50% less time than applying compression in conjunction with a topical barrier-forming material without said composition of the invention.

According to yet another aspect of the invention, a method for inhibiting the formation of hematomas resulting from a cardiac catheterization procedure in a patient, comprises a) applying topically to the patient's skin over a catheter exit site contiguous by 1-10 cm with a catheter puncture in a vein or artery an effective amount of the composition of the invention; b) concurrently applying compression to the punctured vein or artery; and c) recording the number of hematomas formed, wherein the formation of hematomas is inhibited in comparison to applying compression in conjunction with a topical barrier-forming material without said composition of the invention.

In certain embodiments, where the cell-polymer fiber compositions of the invention are administered topically to wound sites, the compositions may further comprise one or more vasoconstrictors. For any vasoconstrictor used in the methods of the invention, the therapeutically effective dose can be estimated initially from tissue or tissue culture assays.

One standard tissue assay is conducted using aortic rings excised from rats. The aorta are then rapidly suspended in a warmed Krebs-Henseleit (KH) buffer consisting of (in mmol/l); 118 NaCl, 4.75 KCl, 2.54 $CaCl_2.2H_2O$, 1.19 $KH_2PO_4$, 1.19 $MgSO_4.7H_2O$, 12.5 $NaHCO_3$, and 10.0 glucose. Isolated vessels can be carefully freed of connective tissue and cut into rings 2-3 mm in length. The rings are then mounted on stainless steel hooks, suspended in a 10-ml tissue bath, and connected to FT-03 force displacement transducers (Grass Instrument, Quincy, Mass.) to record changes in force on a Grass model 7 oscillographic recorder. The baths are filled with KH buffer and aerated at 37° C. with 95% $O_2$+5% $CO_2$. A resting force of 0.5 g is applied to the SMA rings, and then the rings are equilibrated for 90 minutes. During this period, the buffer in the tissue bath is replaced every 15-20 minutes, and the resting force of the vascular rings is adjusted until 0.5 g of pre-load is maintained. After 90 to 120 minutes of equilibration, the rings are exposed to 100 nM U-46619 (9,11-dideoxy-9α-11α-methaneepoxy-prostagalandin $F_{2α}$, Biomol Research Laboratories, Plymouth Meeting, Pa.), a thromboxane $A_2$ mimetic, to generate 1.0 g of developed force. Once a stable contraction is obtained, acetylcholine, a typical endothelium-dependent vasodilator, is added to the bath in cumulative concentrations of 0.1, 1, 10, and 100 nM to assess the integrity of endothelium. After the cumulative response is stabilized, the rings are washed and again allowed to equilibrate to baseline.

This procedure can be used with a vasoconstrictor other than U-46619 to determine the effectiveness of a vasoconstrictor at maintaining vasoconstriction. The procedure can be repeated with varying concentration of a vasoconstrictor to determine effective dosage.

In certain embodiments, where the cell-polymer fiber compositions of the invention are administered topically to wound sites, the compositions may further comprise one or more coagulant. The function and effectiveness of a coagulant can be tested by standard assays. In such assays, normal human blood, without anticoagulant, is drawn and placed in several test tubes. The normal blood, without a composition of the invention, is allowed to clot (usually within 10 minutes). Other samples of normal blood are drawn and one milliliter aliquots are placed in test tubes with descending aliquots of a particular coagulant used in the methods, compositions, and kits of the invention for which one desires to test coagulant properties. With such an assay one can readily determine how many tenths of a milliliter of the coagulant are effective at causing clotting at a greater rate or in less time than blood without a coagulant. Variations on this standard assay can be conducted where the patient has had an anticoagulant introduced into the bloodstream prior to withdrawal of blood. The results can be used to identify coagulant for use in the methods, compositions, and kits of the invention.

In certain embodiments of the invention, where the cell-polymer fiber composition comprises an amount of vasoconstrictor and/or coagulant, the amount may be 0.5-fold, 0.75-fold, 1-fold, 2-fold, 3-fold, 4-fold, 5-fold, 10-fold, 12-fold, 15-fold, 20-fold, 50-fold or 100-fold the effective dosage. For example, such compositions can be manufactured for general use for adults, e.g., adults weighing about 50, 60, 70, 80, or 90 kg, and a topical administration area, e.g., of a patch, of about 1-2, 2-4, 4-8, 8-12, 12-15, 15-20, 20-25, or 25-30 $cm^2$, or a topical administration volume, e.g., of a liquid or gel, of about 0.25-0.5, 0.5-1, 1-1.25, 1.25-1.5, 1.5-1.75, 1.75-2, 2-2.5, or 2.5-3 ml. Exemplary concentration calculations are provided, infra.

In embodiments of the invention where the cell-polymer fiber composition of the invention is formulated as, embedded in, or applied to a patch, and the composition further comprises a vasoconstrictor and/or coagulant, 100 mg of the vasoconstrictor and/or coagulant may be present in 1 cm$^2$ of the wound-contacting surface of the patch. In other embodiments, the effective amount of a vasoconstrictor and/or coagulant for use in the methods, compositions, and kits of the invention present in 1 cm$^2$ of a patch can be about 0.05 mg, 0.10 mg, 0.25 mg, 0.50 mg, 0.75 mg, 1 mg, 2 mg, 5 mg, 8 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, or 2000 mg. In a preferred embodiment, the effective amount of a vasoconstrictor and/or coagulant of the invention present in 1 cm$^2$ of a patch is between 0.05 mg and 30 mg of the vasoconstrictor and/or coagulant.

In other embodiments, where the cell-polymer fiber composition comprises a vasoconstrictor and/or coagulant, the composition is formulated as, embedded in, or applied to a patch, 100 μg of the vasoconstrictor and/or coagulant may be present in 1 cm$^2$ of the wound-contacting surface of the patch. In other embodiments, the effective amount of a vasoconstrictor and/or coagulant of the invention present in 1 cm$^2$ of a patch can be about 5 μg, 10 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, or 160 μg between about 1 mM and 70 mM. An example of a coagulant that can be effective in such amounts is thrombin. An example of a vasoconstrictor that can be effective in such amounts is endothelin-1.

In preferred embodiments of the present methods and compositions, the dose of a vasoconstrictor and/or coagulant, e.g., on the surface of a patch, regardless of its molecular weight, is about 1 mM to about 70 mM. In certain exemplary embodiments, the dose is about 1 mM to about 10 mM, about 10 mM to about 30 mM, about 30 mM to about 50 mM, or about 50 mM to about 70 mM.

In yet other embodiments, the effective amount of a vasoconstrictor and/or coagulant of the invention is about 1-1000 IU/cm$^2$ wherein the vasoconstrictor and/or coagulant is formulated as, embedded in, or applied to a patch. In one embodiment, the vasoconstrictor and/or coagulant forms a concentration gradient that decreases from the site of application to the breach or puncture in the vein or artery. For example, in the case of a cardiac catheterization track wound, the vasoconstrictor and/or coagulant can form a concentration gradient through the track wound and promote clot formation throughout the track resulting in an decreased in the time necessary to achieve hemostasis.

In certain embodiments, an effective amount of a vasoconstrictor and/or coagulant used in the cell-polymer fiber compositions of the invention is an amount that activates hemostasis in the presence of a coagulant or an anticoagulant.

In certain embodiments, the effective dose is the dose necessary to initiate clotting with or without compression. In other embodiments, the effective dose is the dose necessary to cause formation of a firm clot that will remain with or without compression. In yet other embodiments, an effective dose can be determined by the strength of the clot, i.e. the time for which the clot holds with or without compression.

Once it has been determined how varying concentrations and amounts of a particular vasoconstrictor and/or coagulant act in vitro, effective vasoconstrictors and/or coagulants can be further tested in animal models for the distance at which they function. An effective amount of a vasoconstrictor and/or coagulant can be determined by measuring the time to form a clot and the strength of a clot sealing a breach or puncture in a vein or artery with thromboelastography. A series of measurements can be taken varying the concentration or amount of the vasoconstrictor and/or coagulant to determine an effective amount. The distance of a breach or puncture in a vein or artery from the skin surface can also be varied to determine the maximum or optimal effective distance. Such series of measurements can be used to predict how a particular vasoconstrictor and/or coagulant will function at a particular distance, and allow for a determination of effective amount for a desired distance. The distance animal veins or arteries are beneath the skin surface can be determined by imaging techniques such as, but not limited to, ultrasound. The distance at which certain concentrations or amounts of vasoconstrictors and/or coagulants are effective in vivo can be used to extrapolate the effective amount for a desired distance needed for a particular patient, or the limit to the distance at which a particular vasoconstrictor and/or coagulant is effective. Such information can be used to more accurately determine useful doses in humans.

Results from animal models can be extrapolated to determine effective doses for human subjects. Comparing varying concentrations of a vasoconstrictor and/or coagulant in one or more animal models allows for the establishment of dose response curves that can be used to estimate effective amounts in a human, given the particular circumstances of each subject, i.e. distance of wound, size of wound, presence of coagulants or anticoagulants in the blood stream.

Human patients can also be used to determine the distance at which a vasoconstrictor and/or coagulant is effective. For example, ultrasound can be used to visualize the distance a breach or puncture in a vein or artery is from the surface of the skin and determine if blood flow from the breach or puncture has decreased or been eliminated. Ultrasound probes can be used to locate the breached or punctured vein or artery or to image a specific area by aligning the probes with a desired vein or artery. Ultrasound imaging of the breach or puncture site can be combined with Doppler flow analysis. Doppler flow analysis allows for the determination of cessation or reduction of blood flow through the artery or vein. If blood flow through the vein or artery is inhibited, it may cause damage. Thus, combining Doppler flow and ultrasound would allow for a determination of the maximum upper limit of an effective amount of a vasoconstrictor and/or coagulant. For example, if the effect of a coagulant extends into the blood vessel and causes clotting of platelet and cessation of blood within the blood vessel, the effect could be damaging. In another embodiment, the maximum upper limit of an effective amount of a vasoconstrictor and/or coagulant can be measured as the amount of the vasoconstrictor and/or coagulant for use in the methods, compositions, and kits of the invention that causes an increase in cardiac output.

In certain embodiments, the cell-polymer fiber compositions of the methods, compositions, and kits of the invention also comprise an effective amount of a vasoconstrictor. The effective amount of the vasoconstrictor used in will vary with the patients age, condition, and sex, as well as the nature and extent of the condition in the subject, all of which can be determined by one of ordinary skill in the art. For example, a patients body weight can be used to determine an effective amount of a vasoconstrictor.

In one embodiment, the composition topically administered to a patient in the methods of the invention comprises an effective amount of the vasoconstrictor Adrenaline™ in a concentration in the range of about 0.000001 mg/kg of patient body weight to about 11 mg/kg of patient body weight. For adults the preferred Adrenaline™ concentration range is about 0.00001 mg/kg to about 0.5 mg/kg. In related embodiments the effective amount of Adrenaline™ is approximately 0.00001 mg/kg, 0.00005 mg/kg, 0.0001 mg/kg, 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, or 11.0 mg/kg of patient body weight. In related embodiments the effective amount of Adrenaline™ is about 0.00001 mg/kg to 0.0001 mg/kg, 0.001 mg/kg to 0.01 mg/kg, 0.1 mg/kg to 1.0 mg/kg, 2.0 mg/kg to 3.0 mg/kg, 4.0 mg/kg to 5.0 mg/kg, 6.0 mg/kg to 7.0 mg/kg, 8.0 mg/kg to 9.0 mg/kg, or 10.0 mg/kg to 11.0 mg/kg of patient body weight. In related embodiments the effective amount of Adrenaline™ is about 0.00005 mg/kg to 0.0005 mg/kg, 0.005 mg/kg to 0.05 mg/kg, 0.5 mg/kg to 1.5 mg/kg, 2.5 mg/kg to 3.5 mg/kg, 4.5 mg/kg to 5.5 mg/kg. 6.5 mg/kg to 7.5 mg/kg, 8.5 mg/kg to 9.5 mg/kg, or 10.5 mg/kg to 11.5 mg/kg of patient body weight In another embodiment, the composition topically administered to a patient in the methods of the invention comprises an effective amount of the vasoconstrictor metaraminol bitartrate in a concentration in the range of about 0.00001 mg/kg of patient body weight to about 1500 mg/kg of patient body weight. For adults the preferred metaraminol bitartrate concentration range is about 0.0005 mg/kg to about 4.5 mg/kg. In related embodiments the effective amount of metaraminol bitartrate is approximately 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 10 mg/kg, 50 mg/kg, 100 mg/kg, 150 mg/kg, 200 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, or 1500 mg/kg of patient body weight. In related embodiments the effective amount of metaraminol bitartrate is about 0.0005 mg/kg to 0.005 mg/kg, 0.05 mg/kg to 0.5 mg/kg, 50 mg/kg to 150 mg/kg, 300 mg/kg to 500 mg/kg, 700 mg/kg to 900 mg/kg, 1100 mg/kg to 1300 mg/kg, or 1300 mg/kg to 1500 mg/kg of patient body weight. In related embodiments the effective amount of metaraminol bitartrate is about 0.001 mg/kg to 0.01 mg/kg, 0.1 mg/kg to 1.0 mg/kg, 10 mg/kg to 100 mg/kg, 200 mg/kg to 400 mg/kg, 600 mg/kg to 800 mg/kg, 1000 mg/kg to 1200 mg/kg, or 1200 mg/kg to 1400 mg/kg of patient body weight.

In one embodiment, the composition topically administered to a patient in the methods of the invention comprises an effective amount of the vasoconstrictor dopamine HCl in a concentration in the range of about 0.00001 mg/kg of patient body weight to about 150 mg/kg of patient body weight. For adults the preferred dopamine HCl concentration range is about 0.0005 mg/kg to about 10 mg/kg. In related embodiments the effective amount of dopamine HCl is approximately 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, or 150 mg/kg of patient body weight. In related embodiments the effective amount of dopamine HCl is about 0.0005 mg/kg to 0.005 mg/kg, 0.05 mg/kg to 0.5 mg/kg, 10 mg/kg to 30 mg/kg, 50 mg/kg to 70 mg/kg, 90 mg/kg to 110 mg/kg, or 130 mg/kg to 150 mg/kg of patient body weight. In related embodiments the effective amount of dopamine HCl is about 0.001 mg/kg to 0.01 mg/kg, 0.1 mg/kg to 1.0 mg/kg, 10 mg/kg to 20 mg/kg, 40 mg/kg to 60 mg/kg, 80 mg/kg to 100 mg/kg, or 120 mg/kg to 140 mg/kg of patient body weight.

In one embodiment, the composition topically administered to a patient in the methods of the invention comprises an effective amount of the vasoconstrictor isoproterenol HCl in a concentration in the range of about 0.00001 mg/kg of patient body weight to about 150 mg/kg of patient body weight. For adults the preferred isoproterenol HCl concentration range is about 0.0005 mg/kg to about 5 mg/kg. In related embodiments the effective amount of isoproterenol HCl is approximately 0.0001 mg/kg, 0.0005 mg/kg, 0.001 mg/kg, 0.005 mg/kg, 0.01 mg/kg, 0.05 mg/kg, 0.1 mg/kg. 0.5 mg/kg, 1.0 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, or 150 mg/kg of patient body weight. In related embodiments the effective amount of isoproterenol HCl is about 0.0001 mg/kg to 0.001 mg/kg, 0.01 mg/kg to 0.1 mg/kg, 1.0 mg/kg to 20 mg/kg, 40 mg/kg to 60 mg/kg, 80 mg/kg to 100 mg/kg, or 120 mg/kg to 140 mg/kg of patient body weight. In related embodiments the effective amount of isoproterenol HCl is about 0.0005 mg/kg to 0.005 mg/kg, 0.05 mg/kg to 0.1 mg/kg, 0.5 mg/kg to 10 mg/kg, 30 mg/kg to 50 mg/kg, 70 mg/kg to 90 mg/kg, 110 mg/kg to 130 mg/kg, or 130 mg/kg to 150 mg/kg of patient body weight.

In one embodiment, the composition topically administered to a patient in the methods of the invention comprises an effective amount of the vasoconstrictor norepinephrine in a concentration in the range of about 0.00001 mg/kg of patient body weight to about 2 mg/kg of patient body weight. For adults the preferred norepinephrine concentration range is about 0.0001 mg/kg to about 0.01 mg/kg. In related embodiments the effective amount of norepinephrine is approximately 0.0001 mg/kg, 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 1.5 mg/kg, or 2 mg/kg of patient body weight. In related embodiments the effective amount of norepinephrine is about 0.0001 mg/kg to 0.001 mg/kg, 0.01 mg/kg to 0.1 mg/kg, or 1.0 mg/kg to 2 mg/kg of patient body weight. In related embodiments the effective amount of norepinephrine is about 0.0005 mg/kg to 0.005 mg/kg, 0.05 mg/kg to 0.5 mg/kg, or 1.5 mg/kg to 2 mg/kg of patient body weight.

In one embodiment, the composition topically administered to a patient in the methods of the invention comprises an effective amount of the vasoconstrictor Serotonin™ in a concentration in the range of about 0.0001 mg/kg of patient body weight to about 750 mg/kg of patient body weight. For adults the preferred Serotonin™ concentration range is about 0.001 mg/kg to about 0.6 mg/kg. In related embodiments the effective amount of Serotonin™ is approximately 0.001 mg/kg, 0.005 mg/kg, 0.01 mg/kg, 0.05 mg/kg, 0.1 mg/kg, 0.5 mg/kg, 1.0 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg. 200 mg/kg, 210 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, or 750 mg/kg of patient body weight. In related embodiments the effective amount of Serotonin™ is about 0.001 mg/kg to 0.01 mg/kg, 0.1 mg/kg to 1.0 mg/kg, 20 mg/kg to 40 mg/kg, 60 mg/kg to 80 mg/kg, 100 mg/kg to 120 mg/kg, 140 mg/kg to 160 mg/kg, 180 mg/kg to 200 mg/kg, 210 mg/kg to 300 mg/kg, 400 mg/kg to 500 mg/kg, or 600 mg/kg to 700 mg/kg of patient body weight. In related embodiments the effective amount of Serotonin™ is about 0.005 mg/kg to 0.05 mg/kg, 0.5 mg/kg to 10 mg/kg, 30 mg/kg to 50 mg/kg, 70 mg/kg to 90 mg/kg, 110 mg/kg to 130 mg/kg, 150 mg/kg to 170 mg/kg, 190 mg/kg to 210 mg/kg, 250 mg/kg to 350 mg/kg, 450 mg/kg to 550 mg/kg, or 650 mg/kg to 750 mg/kg of patient body weight.

In one embodiment, the composition topically administered to a patient in the methods of the invention comprises an effective amount of the vasoconstrictor endothelin in a concentration in the range of about $4.5 \times 10^{-8}$ mg/kg of patient body weight to about $5.0 \times 10^{-6}$ mg/kg of patient body weight. In related embodiments the effective amount of endothelin is approximately $4.5 \times 10^{-8}$ mg/kg, $5.0 \times 10^{-8}$ mg/kg, $5.5 \times 10^{-8}$ mg/kg, $6.0 \times 10^{-8}$ mg/kg, $6.5 \times 10^{-8}$ mg/kg, $7.0 \times 10^{-8}$ mg/kg, $7.5 \times 10^{-8}$ mg/kg, $8.0 \times 10^{-8}$ mg/kg, $8.5 \times 10^{-8}$ mg/kg, $9.0 \times 10^{-8}$ mg/kg, $9.5 \times 10^{-8}$ mg/kg, $1.0 \times 10^{-7}$ mg/kg, $1.5 \times 10^{-7}$ mg/kg, $2.0 \times 10^{-7}$ mg/kg, $2.5 \times 10^{-7}$ mg/kg, $3.0 \times 10^{-7}$ mg/kg, $3.5 \times 10^{-7}$ mg/kg, $4.0 \times 10^{-7}$ mg/kg, $4.5 \times 10^{-7}$ mg/kg, $5.0 \times 10^{-7}$ mg/kg, $5.5 \times 10^{-7}$ mg/kg, $6.0 \times 10^{-7}$ mg/kg, $6.5 \times 10^{-7}$ mg/kg, $7.0 \times 10^{-7}$ mg/kg, $7.5 \times 10^{-7}$ mg/kg, $8.0 \times 10^{-7}$ mg/kg, $8.5 \times 10^{-7}$ mg/kg, $9.0 \times 10^{-7}$ mg/kg, $1.0 \times 10^{-6}$ mg/kg, $1.5 \times 10^{-6}$ mg/kg, $2.0 \times 10^{-6}$ mg/kg, $2.5 \times 10^{-6}$ mg/kg, $3.0 \times 10^{-6}$ mg/kg, $3.5 \times 10^{-6}$ mg/kg, $4.0 \times 10^{-6}$ mg/kg, $4.5 \times 10^{-6}$ mg/kg, or $5.0 \times 10^{-6}$ mg/kg of patient body weight. In related embodiments the effective amount of endothelin is about $5.0 \times 10^{-8}$ mg/kg to $6.0 \times 10^{-8}$ mg/kg, $7.0 \times 10^{-8}$ mg/kg to $8.0 \times 10^{-8}$ mg/kg, $9.0 \times 10^{-8}$ mg/kg to $1.0 \times 10^{-7}$ mg/kg, $2.0 \times 10^{-7}$ mg/kg to $3.0 \times 10^{-7}$ mg/kg, $4.0 \times 10^{-7}$ mg/kg to $5.0 \times 10^{-7}$ mg/kg, $6.0 \times 10^{-7}$ mg/kg to $7.0 \times 10^{-7}$ mg/kg, $8.0 \times 10^{-7}$ mg/kg to $9.0 \times 10^{-7}$ mg/kg, $1.0 \times 10^{-6}$ mg/kg to $2.0 \times 10^{-6}$ mg/kg, $3.0 \times 10^{-6}$ mg/kg to $4.0 \times 10^{-6}$ mg/kg, or $4.0 \times 10^{-6}$ mg/kg to $5.0 \times 10^{-6}$ mg/kg of patient body weight. In related embodiments the effective amount of endothelin is about $4.5 \times 10^{-8}$ mg/kg to $5.5 \times 10^{-8}$ mg/kg, $6.5 \times 10^{-8}$ mg/kg to $7.5 \times 10^{-8}$ mg/kg, $8.5 \times 10^{-8}$ mg/kg to $9.5 \times 10^{-8}$ mg/kg, $1.5 \times 10^{-7}$ mg/kg to $2.5 \times 10^{-7}$ mg/kg, $3.5 \times 10^{-7}$ mg/kg to $4.5 \times 10^{-7}$ mg/kg, $5.5 \times 10^{-7}$ mg/kg to $6.5 \times 10^{-7}$ mg/kg, $7.5 \times 10^{-7}$ mg/kg to $8.5 \times 10^{-7}$ mg/kg, $1.5 \times 10^{-6}$ mg/kg to $2.5 \times 10^{-6}$ mg/kg, or $3.5 \times 10^{-6}$ mg/kg to $4.5 \times 10^{-6}$ mg/kg of patient body weight.

For other vasoconstrictors, including but not limited to, endothelin-1, epinephrine, phenylephrine, thromboxane, prostaglandin, methergine, oxytocin, isopreland U-46619, papaverine, yohimbine, visnadin, khellin, bebellin, and nicotinate derivatives, one skilled in the art would be able to determine appropriate effective doses. In related embodiments the effective amount of a vasoconstrictor is approximately $4.5 \times 10^{-8}$ mg/kg, $5.0 \times 10^{-8}$ mg/kg, $6.0 \times 10^{-8}$ mg/kg, $7.0 \times 10^{-8}$ mg/kg, $8.0 \times 10^{-8}$ mg/kg, $9.0 \times 10^{-8}$ mg/kg, $1.0 \times 10^{-7}$ mg/kg, $2.0 \times 10^{-7}$ mg/kg, $3.0 \times 10^{-7}$ mg/kg, $4.0 \times 10^{-7}$ mg/kg, $5.0 \times 10^{-7}$ mg/kg, $6.0 \times 10^{-7}$ mg/kg, $7.0 \times 10^{-7}$ mg/kg, $8.0 \times 10^{-7}$ mg/kg, $9.0 \times 10^{-7}$ mg/kg, $1.0 \times 10^{-6}$ mg/kg, $2.0 \times 10^{-6}$ mg/kg, $3.0 \times 10^{-6}$ mg/kg, $4.0 \times 10^{-6}$ mg/kg, $5.0 \times 10^{-6}$ mg/kg, $6.0 \times 10^{-6}$ mg/kg, $7.0 \times 10^{-6}$ mg/kg, $8.0 \times 10^{-6}$ mg/kg, $9.0 \times 10^{-6}$ mg/kg, $1.0 \times 10^{-5}$ mg/kg, $2.0 \times 10^{-5}$ mg/kg, $3.0 \times 10^{-5}$ mg/kg, $4.0 \times 10^{-5}$ mg/kg, $5.0 \times 10^{-5}$ mg/kg, $6.0 \times 10^{-5}$ mg/kg, $7.0 \times 10^{-5}$ mg/kg, $8.0 \times 10^{-5}$ mg/kg, $9.0 \times 10^{-5}$ mg/kg, $1.0 \times 10^{-4}$ mg/kg. $2.0 \times 10^{-4}$ mg/kg, $3.0 \times 10^{-4}$ mg/kg, $4.0 \times 10^{-4}$ mg/kg, $5.0 \times 10^{-4}$ mg/kg, $6.0 \times 10^{-4}$ mg/kg, $7.0 \times 10^{-4}$ mg/kg, $8.0 \times 10^{-4}$ mg/kg, $9.0 \times 10^{-4}$ mg/kg, $1.0 \times 10^{-3}$ mg/kg, $2.0 \times 10^{-3}$ mg/kg, $3.0 \times 10^{-3}$ mg/kg, $4.0 \times 10^{-3}$ mg/kg, $5.0 \times 10^{-3}$ mg/kg, $6.0 \times 10^{-3}$ mg/kg, $7.0 \times 10^{-3}$ mg/kg, $8.0 \times 10^{-3}$ mg/kg, $9.0 \times 10^{-3}$ mg/kg, $1.0 \times 10^{-2}$ mg/kg, $2.0 \times 10^{-2}$ mg/kg, $3.0 \times 10^{-2}$ mg/kg, $4.0 \times 10^{-2}$ mg/kg, $5.0 \times 10^{-2}$ mg/kg, $6.0 \times 10^{-2}$ mg/kg, $7.0 \times 10^{-2}$ mg/kg, $8.0 \times 10^{-2}$ mg/kg, $9.0 \times 10^{-2}$ mg/kg, 0.1 mg/kg, 0.5 mg/kg, 1.0 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, or 1500 mg/kg of patient body weight.

In certain embodiments, the effective amount of a vasoconstrictor is in the range of about $6.0 \times 10^{-8}$ mg/kg to $1.0 \times 10^{-7}$ mg/kg, $1.0 \times 10^{-7}$ mg/kg to $4.0 \times 10^{-7}$ mg/kg, $4.0 \times 10^{-7}$ mg/kg to $8.0 \times 10^{-7}$ mg/kg, $8.0 \times 10^{-7}$ mg/kg to $2.0 \times 10^{-6}$ mg/kg, $2.0 \times 10^{-6}$ mg/kg to $6.0 \times 10^{-6}$ mg/kg, $6.0 \times 10^{-6}$ mg/kg to $1.0 \times 10^{-5}$ mg/kg, $1.0 \times 10^{-5}$ mg/kg to $4.0 \times 10^{-5}$ mg/kg, $4.0 \times 10^{-5}$ mg/kg to $8.0 \times 10^{-5}$ mg/kg, $8.0 \times 10^{-5}$ mg/kg to $2.0 \times 10^{-4}$ mg/kg, $2.0 \times 10^{-4}$ mg/kg to $6.0 \times 10^{-4}$ mg/kg, $6.0 \times 10^{-4}$ mg/kg to $1.0 \times 10^{-3}$ mg/kg, $1.0 \times 10^{-3}$ mg/kg to $4.0 \times 10^{-3}$ mg/kg, $4.0 \times 10^{-3}$ mg/kg to $8.0 \times 10^{-3}$ mg/kg, $8.0 \times 10^{-3}$ mg/kg to $2.0 \times 10^{-2}$ mg/kg, $2.0 \times 10^{-2}$ mg/kg to $6.0 \times 10^{-2}$ mg/kg, $6.0 \times 10^{-2}$ mg/kg to 0.1 mg/kg, 0.1 mg/kg to 0.4 mg/kg, 0.4 mg/kg to 0.8 mg/kg, 0.8 mg/kg to 2.0 mg/kg, 2.0 mg/kg to 6.0 mg/kg, 6.0 mg/kg to 10 mg/kg, 10 mg/kg to 40 mg/kg, 40 mg/kg to 80 mg/kg, 80 mg/kg to 120 mg/kg, 120 mg/kg to 160 mg/kg, 160 mg/kg to 200 mg/kg, 200 mg/kg to 240 mg/kg, 280 mg/kg to 320 mg/kg, 320 mg/kg to 360 mg/kg, 360 mg/kg to 400 mg/kg, 400 mg/kg to 440 mg/kg, 440 mg/kg to 480 mg/kg, 480 mg/kg to 520 mg/kg, 520 mg/kg to 560 mg/kg, 560 mg/kg to 600 mg/kg, 600 mg/kg to 640 mg/kg, 640 mg/kg to 680 mg/kg, 680 mg/kg to 720 mg/kg, 720 mg/kg to 760 mg/kg, 760 mg/kg to 800 mg/kg, 800 mg/kg to 840 mg/kg, 840 mg/kg to 880 mg/kg, 880 mg/kg to 920 mg/kg, 920 mg/kg to 960 mg/kg, 960 mg/kg to 1000 mg/kg, 1000 mg/kg to 1040 mg/kg, 1040 mg/kg to 1080 mg/kg, 1080 mg/kg to 1120 mg/kg, 1120 mg/kg to 1160 mg/kg, 1160 mg/kg to 1200 mg/kg, 1200 mg/kg to 1240 mg/kg, 1240 mg/kg to 1280 mg/kg, 1280 mg/kg to 1320 mg/kg, 1320 mg/kg to 1360 mg/kg, 1360 mg/kg to 1400 mg/kg, 1400 mg/kg to 1440 mg/kg, 1440 mg/kg to 1480 mg/kg, or 1480 mg/kg to 1520 mg/kg of patient body weight.

In certain embodiments, the effective amount of a vasoconstrictor is in the range of about $4.5 \times 10^{-8}$ mg/kg to $8.0 \times 10^{-8}$ mg/kg, $8.0 \times 10^{-8}$ mg/kg to $2.0 \times 10^{-7}$ mg/kg, $2.0 \times 10^{-7}$ mg/kg to $6.0 \times 10^{-7}$ mg/kg, $6.0 \times 10^{-7}$ mg/kg to $1.0 \times 10^{-6}$ mg/kg, $1.0 \times 10^{-6}$ mg/kg to $4.0 \times 10^{-6}$ mg/kg, $4.0 \times 10^{-6}$ mg/kg to $8.0 \times 10^{-6}$ mg/kg, $8.0 \times 10^{-6}$ mg/kg to $2.0 \times 10^{-5}$ mg/kg, $2.0 \times 10^{-5}$ mg/kg to $6.0 \times 10^{-5}$ mg/kg, $6.0 \times 10^{-5}$ mg/kg to $1.0 \times 10^{-4}$ mg/kg, $1.0 \times 10^{-4}$ mg/kg to $4.0 \times 10^{-4}$ mg/kg, $4.0 \times 10^{-4}$ mg/kg to $8.0 \times 10^{-4}$ mg/kg, $8.0 \times 10^{-4}$ mg/kg to $2.0 \times 10^{-3}$ mg/kg, $2.0 \times 10^{-3}$ mg/kg to $6.0 \times 10^{-3}$ mg/kg, $6.0 \times 10^{-3}$ mg/kg to $1.0 \times 10^{-2}$ mg/kg, $1.0 \times 10^{-2}$ mg/kg to $4.0 \times 10^{-2}$ mg/kg, $4.0 \times 10^{-2}$ mg/kg to $8.0 \times 10^{-2}$ mg/kg, $8.0 \times 10^{-2}$ mg/kg to 0.2 mg/kg, 0.2 mg/kg to 0.6 mg/kg, 0.6 mg/kg to 1.0 mg/kg, 1.0 mg/kg to 4.0 mg/kg, 4.0 mg/kg to 8.0 mg/kg, 8.0 mg/kg to 12 mg/kg, 12 mg/kg to 16 mg/kg, 16 mg/kg to 20 mg/kg, 20 mg/kg to 60 mg/kg, 60 mg/kg to 100 mg/kg, 100 mg/kg to 140 mg/kg, 140 mg/kg to 180 mg/kg, 180 mg/kg to 220 mg/kg, 220 mg/kg to 260 mg/kg, 260 mg/kg to 300 mg/kg, 300 mg/kg to 340 mg/kg, 340 mg/kg to 380 mg/kg, 380 mg/kg to 420 mg/kg, 420 mg/kg to 460 mg/kg, 460 mg/kg to 500 mg/kg, 500 mg/kg to 540 mg/kg, 540 mg/kg to 580 mg/kg, 580 mg/kg to 620 mg/kg, 620 mg/kg to 660 mg/kg, 660 mg/kg to 700 mg/kg, 700 mg/kg to 740 mg/kg, 740 mg/kg to 780 mg/kg, 780 mg/kg to 820 mg/kg, 820 mg/kg to 860 mg/kg, 860 mg/kg to 900 mg/kg, 900 mg/kg to 940 mg/kg, 940 mg/kg to 980 mg/kg, 980 mg/kg to 1020 mg/kg, 1020 mg/kg to 1060 mg/kg, 1060 mg/kg to 1100 mg/kg, 1100 mg/kg to 1140 mg/kg, 1140 mg/kg to 1180 mg/kg, 1180 mg/kg to 1220 mg/kg, 1220 mg/kg to 1260 mg/kg, 1260 mg/kg to 1300 mg/kg, 1300 mg/kg to 1340 mg/kg, 1340 mg/kg to 1380 mg/kg, 1380 mg/kg to 1420 mg/kg, 1420 mg/kg to 1460 mg/kg, or 1460 mg/kg to 1500 mg/kg of patient body weight.

In general, the effective does of a vasoconstrictor used in certain embodiments of the cell-polymer fiber compositions of the methods, compositions, and kits of the invention is a concentration that is less than an amount that would cause systemic vasoconstriction when administered intravenously.

The effective amount of a vasoconstrictor can also be described in the context of particular formulations of the compositions used in the methods, compositions, and kits of the invention. For example, where the composition is formulated as or applied to a patch for administration following a cardiac catheterization procedure, the cell-polymer fiber composition comprises adrenaline as a vasoconstrictor, and the patient is an adult weighing about 70 kg, then the patch should comprise adrenaline in the concentration range of about 0.00075 mg/kg to about 37.5 mg/kg. Since a patch used in such procedures is typically about 4 cm$^2$ to 25 cm$^2$, depending on the F size of the catheter used, one skilled in the art could readily determine the concentration in units of mg of adrenaline per cm$^2$ of patch, e.g., about 0.00020 mg/cm$^2$ to about 1.5 mg/cm$^2$. Similarly, for example, where the composition is formulated as a gel or liquid, for administration following a cardiac catheterization procedure, adrenaline is the vasoconstrictor used in the composition, and the patient is an adult weighing about 70 kg, then the gel should comprise adrenaline in the concentration range of about 0.00075 mg/kg to about 37.5 mg/kg. Since a gel used in such procedures is typically about 1-2 ml, one skilled in the art could readily determine the concentration in units of mg of adrenaline per ml of gel, e.g., about 0.00075 mg/ml to about 18.75 mg/ml.

The example conversion calculation described above can be performed to allow the extrapolation of suitable concentration ranges for topical application any of the dosage ranges for any of the vasoconstrictors and/or coagulants described herein above or any vasoconstrictors and/or coagulant suitable for use in the methods, compositions, and kits of the invention. In preferred embodiments, where the composition is formulated as a patch, gel, or liquid, such compositions can be manufactured for general use for adults, e.g., adults weighing about 50, 60, 70, 80, or 90 kg, and a topical administration area, e.g., of a patch, of about 1-2, 2-4, 4-8, 8-12, 12-15, 15-20, 20-25, or 25-30 cm$^2$, or a topical administration volume, e.g., of a liquid or gel, of about 0.25-0.5, 0.5-1, 1-1.25, 1.25-1.5, 1.5-1.75, 1.75-2, 2-2.5, or 2.5-3 ml.

5.6.4 Disease

The diseases that can be treated or prevented using the methods and compositions of the present invention include, but are not limited to, infectious disease, autoimmune disease, cancer, and proliferative disorders. In certain embodiments, the patient is implanted with a composition comprising cells that produce agents known to be useful in treating a particular infection or cells that elicit and immune response. Alternatively, the patient is treated topically for skin infections and/or infections on the surface of internal organs that have been exposed as a result of trauma or surgery. In certain embodiments, the patient is topically administered a composition comprising cells that produce agents known to be useful in treating a particular infection or cells that elicit and immune response. In such embodiments the compositions of the invention may be preventative, in that they provide both a barrier to pathogens and can in certain embodiments comprise cells or agents that protect against the establishment of pathogenic agents. In other embodiments, the patient is implanted with or applied onto a composition comprising cells for the purpose of growth of new tissue and/or cells to replace tissue damaged by infectious disease, autoimmune disease, cancer, proliferative disorders, cells and tissues damaged by chemotherapy or other treatments, or trauma.

5.6.4.1 Infectious Disease

The present methods and compositions can be used in the treatment of injuries caused to cells or tissues by an infectious agent. The present methods and compositions can be used to treat tissue injuries caused by, for example, intracellular pathogens such as viruses, bacteria, protozoans, and intracellular parasites.

In certain embodiments, the present methods and compositions can be used in the treatment of injuries caused by viruses such as hepatitis type B virus, parvoviruses, such as adeno-associated virus and cytomegalovirus, papovaviruses such as papilloma virus, polyoma viruses, and SV40, adenoviruses, herpes viruses such as herpes simplex type I (HSV-I), herpes simplex type II (HSV-II), and Epstein-Barr virus, poxviruses, such as variola (smallpox) and vaccinia virus, RNA viruses, including but not limited to human immunodeficiency virus type I (HIV-I), human immunodeficiency virus type II (HIV-II), human T-cell lymphotropic virus type I (HTLV-I), and human T-cell lymphotropic virus type II (HTLV-II); influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

In another embodiment, the present methods and compositions can be used to treat tissue injuries caused by pathogenic bacteria including, but not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (Vibrio) *fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhiimurium, Salmonella typhii, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori.*

In another preferred embodiment, the methods and compositions can be used to treat injuries caused by pathogenic protozoans such as, but not limited to, *Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum,* and *Plasmodium malaria.*

5.6.4.2 Proliferative and Oncogenic Disease

With respect to specific injuries caused by proliferative and oncogenic disease, the methods and compositions of the present invention can be used to treat injuries caused by: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

Diseases and disorders involving a deficiency in cell proliferation and that can be treated or prevented by establishing new cell populations via implantation of polymer fiber-cell compositions, include but are not limited to degenerative disorders, growth deficiencies, hypoproliferative disorders, physical trauma, lesions, and wounds; for example, to promote wound healing, or to promote regeneration in degenerated, lesioned or injured tissues, etc.

5.6.4.3 Autoimmune Disease

The methods and compositions of the present invention can be used to treat such autoimmune diseases by implanting compositions with cells that reduce or eliminate the immune response to the patient's own (self) tissue, or implanting cells to replace a patients own cells affected by the disease. In implanting the compositions of the invention comprising cells can also be used to establish cells that provide localized protection against the patients own immune system thereby locally preventing disease. The present invention further provides methods and compositions for treating tissue injuries caused by autoimmune diseases, generally involving implantation of a fiber-cell matrix of the invention.

Such autoimmune disease include, but are not limited to, insulin dependent diabetes mellitus (i.e., IDDM, or autoimmune diabetes), multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease. The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis.

5.6.4.4 Nervous System Disorders and Injuries

Nervous system disorders or injuries involving cell types that require supplementation or replacement can be treated by the methods of the invention. These include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency. Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

In a specific embodiments, motor neuron disorders that may be treated with the compositions and methods of the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.6.4.5 Cosmetic Applications

Many aspects of cosmetic surgery involve the introduction of foreign objects into the human body. In one non-limiting example, breast enlargement comprises the insertion of sacs containing silicone or saline. These sacs are under the danger of rupturing or leaking, causing deleterious side effects, and also prevent women from nursing their infants. Thus, cells from the plastic surgery patient can be included in the compositions of the invention for implantation into breast tissue and, in one embodiment, the composition implanted in place of saline or silicone sacs. In another embodiment, the breast tissue implants of compositions of the invention comprising cells from plastic surgery are used after a mastectomy.

5.7 Activating and/or Aggregating Platelets Using the Methods of the Invention There are several platelet activity tests that are commonly used to determine the activity of platelets after storage periods. The tests include platelet number determination, hypotonic stress response, collagen-induced aggregation and adenosine diphosphate (ADP)-induced aggregation. Hypotonic stress response is an assay used to determine if platelets have retained metabolic viability. This assay is a photometric measurement of the platelets' ability to overcome the addition of a hypotonic solution. This activity reflects cell function (i.e. a functional membrane water pump) and is indicative of platelet recovery following storage. Hypotonic stress response has been demonstrated to be an important indicator of platelets' ability to survive in once placed in contact with and open wound, or returned to the body through implantation or injection. Consequently, hypotonic stress response represents a crucial parameter for evaluating platelet biochemistry following storage. The test described above can be used on platelets that are complexed to the polymer fibers of the invention.

Potential for aggregation is another feature that demonstrates whether blood platelets have maintained their functional integrity during storage. This potential is measured by using ADP and collagen to induce aggregation. An agonist is an agent that binds to a receptor and initiates a certain response. In an agonist-induced aggregation, the aggregation or clumping is the response. The agonists, ADP and collagen, are used to induce aggregation to determine if platelets have retained their ability to aggregate. In addition, when performing aggregation responses one can detect the presence of spontaneous aggregation, that is the platelets adhering to each other without the addition of an agonist. The occurrence of spontaneous aggregation has been correlated with removal of platelets from the circulation. When such agonists are added to the compositions of the invention the degree of aggregation can be recorded. If this is done repeatedly over time, the effectiveness, in terms of platelet aggregation, of the compositions of the invention can be monitored. Alternatively, such tests can be used to assess stored platelets prior to production of the compositions of the invention.

In addition, the assays for platelet activation described in Example Section 9 can also be utilized in assessing platelet activation through direct observation of cells using microscopy and/or lyophilization techniques.

5.8 Dosage and Administration of the Compositions and Methods of the Invention Generally, a therapeutically effective amount of a composition of the invention, will vary with a patients age, condition, and sex, as well as the nature and extent of the condition in the subject, all of which can be determined by one of ordinary skill in the art. For example, the effective dose (i.e., amount) needed for an infant may differ from an elderly patient. The actual amount and formulation of the biological material or the composition thereof to be administered will depend on various factors such as the severity of the wound, the condition of the patient, the age of the patient and any collateral injuries or medical ailments possessed by the patient.

Toxicity and efficacy of the compositions of the invention can be determined by standard pharmaceutical procedures in cell cultures or experimental animals, e.g., for determining the ED50 (the dose therapeutically effective in 50% of the population). Compositions that exhibit greater therapeutic effect are preferred. In the present instance, compositions that exhibit toxic side effects may be used in carrying out the methods of the invention. The potential damage to unaffected cells is minimized, since the compositions are applied to the site of affected tissue and thereby reduce the risk of side effects. The dosage of such compositions lies preferably within a range of concentrations that include the ED50. The dosage may vary within this range depending upon the formulation of the composition, i.e., gel, foam, patch, etc.

In embodiments of the invention where the composition of the invention is formulated as or applied to a patch, 100 mg of the composition may be present in 1 $cm^2$ of the wound-contacting surface of the patch. In other embodiments, the effective amount of a composition of the invention present in 1 $cm^2$ of a patch can be about 0.05 mg, 0.10 mg, 0.25 mg, 0.50 mg, 0.75 mg, 1 mg, 2 mg, 5 mg. 8 mg, 10 mg. 15 mg, 20 mg, 25 mg, 30 mg. 35 mg, 40 mg, 45 mg, 50 mg, 55 mg, 60 mg, 65 mg, 70 mg. 75 mg, 80 mg, 85 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, or 2000 mg of the composition, wherein the composition has a concentration between about 1 mM and 70 mM. In a preferred embodiment, the effective amount of a composition of the invention present in 1 $cm^2$ of a patch is between 0.05 mg and 30 mg of the composition, wherein the composition has a concentration between about 1 mM and 70 mM.

The compositions of the invention can be administered topically to wound sites on the skin surface or on the surface of exposed organs, or can be implanted, or injected. In certain embodiments, the compositions of the invention are administered into a catheter track. In other embodiments, the compositions of the invention are administered topically to treat a breach or puncture in a blood vessel, wherein the site of topical administration is contiguous with the breach or puncture in the blood vessel. For injection, the compositions of the invention that are designed for injection, e.g. gels or solutions, can be administered by intradermal, subcutaneous or intramuscular injection.

5.9 Kits

A kit is also provided which according to the invention comprises any of the above described embodiments. The kit can include the composition contained within a sealed, water proof, sterile package which facilitates removal of the composition without contamination. Materials from which containers may be made include aluminum foil, plastic, or another conventional material that is easily sterilized. The kit can contain a single composition or multiple compositions, preferably wherein each is provided in a separate, waterproof, sterile package.

A kit of the invention can comprise a cell-polymer fiber of the invention, optionally with a regulatory notice indicating approval for use on humans or animals.

Alternatively, a kit of the invention can comprise one or more components that can be formulated into a composition of the invention. Optionally included in such kits are instructions for making a composition of the invention and/or administering the composition, once made, to a patient. For example, a kit of the invention can comprise, in one or more compartments, a polymer fiber and isolated cells that interact with or bind to the polymer fiber. Optionally, additional components for making a composition of the invention, for example a divalent cation solution or a salt from which a divalent cation solution can be made, can be included. Additionally, other reagents that can be used in making a composition of the invention, for example sterile water or cell culture medium, can be used. A kit can optionally comprise one or more syringes or other containers or tools for mixing the components of a composition of the invention and/or administering the compositions to a patient. In certain embodiments of the invention, particularly those embodiments involving autologous therapy, a kit of the invention does not contain cells but contains other reagents for making a composition of the invention using a patient's cells.

The kit can comprise a composition that can be formulated as a sponge or three dimensional shape designed to mimic a portion of a mammals body designed for implantation. In such kits, the polymer fiber sponge or other structural component of the invention can be packaged in a separate and sterile compartment for delivery, then cells, for examples cells autologous to a patient to whom the sponge is to be administered, can be added in a medical setting.

In addition or in the alternative, the kits of the invention may provide an instructional material which describes performance of one or more methods of the invention, or a notice in the form prescribed by a governmental agency regulating the manufacture, use or sale of pharmaceuticals or biological products, which notice reflects approval by the agency of manufacture, use or sale for human administration. Thus, a kit can comprise a notice regarding FDA approval and/or instructions for use at a distance and/or in combination with compression.

Additionally, a kit designed for emergency or military use can also contain disposable pre-sterilized instruments, such as scissors, scalpel, clamp, tourniquet, elastic or inelastic bandages, or the like. In a preferred embodiment the kit contains gauze.

The invention can be illustrated by the following embodiments enumerated in the numbered paragraphs that follow:

1. A pharmaceutical composition comprising a complex of an isolated population of mammalian cells and substantially purified polymer fibers which interact with the mammalian cells.
2. The pharmaceutical composition of paragraph 1, wherein the fibers interact with the mammalian cells by way of binding to one or more cell surface proteins present on the mammalian cells.
3. The pharmaceutical composition of paragraph 2, wherein the one or more cell surface proteins comprise GPIIIa, GPIb, or $\alpha_{2b}\beta_3$ integrin.
4. The pharmaceutical composition of paragraph 1, wherein the population of mammalian cells is a population of primary mammalian cells.
5. The pharmaceutical composition of paragraph 1, wherein the composition is frozen at or below 0° C.
6. The pharmaceutical composition of paragraph 1, wherein the composition is stored at or below 22° C.
7. The pharmaceutical composition of paragraph 1, wherein the interaction results in activation of the cells.
8. The pharmaceutical composition of paragraph 7, wherein the activation of the cells is exhibited as a morphological change in the cells.
9. The pharmaceutical composition of paragraph 7, wherein the morphological change in the cells comprises extension of podia.
10. The pharmaceutical composition of paragraph 1, wherein the population of cells comprises lymphocytes, granulocytes, basophils, neutrophils, lymphatic cells, macrophages, endothelial cells, fibroblasts, chondrocytes, mesenchymal cells, hematopoietic cells, granulocytes, erythrocytes, eosinophils, epithelials, hepatocytes, myloid cells, stem cells or fetal cells.
11. The pharmaceutical composition of paragraph 1, wherein the population of cells is a substantially purified population.
12. The pharmaceutical composition of paragraph 1, wherein the population of cells comprises cells derived from different tissues or bodily fluids.
13. The pharmaceutical composition of paragraph 1, wherein the population of cells comprises platelets.
14. The pharmaceutical composition of paragraph 13, wherein the platelets are substantially purified.
15. The pharmaceutical composition of paragraph 1, wherein the population of cells comprises red blood cells.
16. The pharmaceutical composition of paragraph 15, wherein the red blood cells are substantially purified.
17. The pharmaceutical composition of paragraph 1, wherein the fibers are approximately 5 µm to 1 cm in length as detected by scanning electron microscopy.
18. The pharmaceutical composition of paragraph 17, wherein the fibers are approximately 50 µm to 750 µm in length as detected by scanning electron microscopy.
19. The pharmaceutical composition of paragraph 17, wherein the fibers are approximately 100 µM to 500 µm in length as detected by scanning electron microscopy.
20. The pharmaceutical composition of any of claims 17-19, wherein the fibers have a width of 10-500 nm as detected by scanning electron microscopy.
21. The pharmaceutical composition of any of claims 17-19, wherein the fibers have a width of 25-250 nm as detected by scanning electron microscopy.
22. The pharmaceutical composition of any of claims 17-19, wherein the fibers have a width of 50-100 nm as detected by scanning electron microscopy.
23. The pharmaceutical composition of paragraph 1, wherein the polymer fiber is poly-β-1→4-N-acetylglucosamine.
24. The pharmaceutical composition of paragraph 23, wherein the poly-β-1→4-N-acetylglucosamine is microalgal poly-β-1→4-N-acetylglucosamine.
25. The pharmaceutical composition of paragraph 24, wherein the microalgal poly-β-1→4-N-acetylglucosamine is from the *Coscinodiscus* genus, the *Cyclotella* genus, or the *Thalassiosira* genus of microalgae.
26. The pharmaceutical composition of paragraph 25, wherein the microalgal poly-β-1→4-N-acetylglucosamine is from the *Thalassiosira* genus of microalgae and wherein the species of *Thalassiosira* is *fluviatilis* or *weissflogii*.
27. The pharmaceutical composition of paragraph 1, wherein the fibers are formulated as a gel, solid, liquid, sponge, foam, spray, emulsion, suspension, or solution, mat, string, gauze, suture, bead, microsphere, or microfibril.
28. The pharmaceutical composition of paragraph 1, wherein the composition comprises poly-β-1→4-N-acetylglucosamine fibers and platelets formulated as a suture.
29. The pharmaceutical composition of paragraph 1, wherein the ratio of the volume of cells isolated to the volume of polymer fiber suspension is 1:1.
30. The pharmaceutical composition of paragraph 1, further comprising a divalent cation.
31. The pharmaceutical composition of paragraph 30, wherein the divalent cation is magnesium.
32. The pharmaceutical composition of paragraph 30, wherein the divalent cation is calcium.
33. The pharmaceutical composition of paragraph 32, wherein the calcium is 10% $CaCl_2$ solution.
34. The pharmaceutical composition of paragraph 1, wherein the population of cells have been isolated mammal for at least 1, 2, 3 or 4 days.

35. The pharmaceutical composition of paragraph 1, further comprising one or more growth factors or cytokines.

36. The pharmaceutical composition of paragraph 35, wherein the growth factor is nerve growth factor, platelet-derived growth factor, RBPJκ binding domain of Notch, retinoic acid, mast cell growth factor, transforming growth factor-β, or thrombopoietin.

37. The pharmaceutical composition of paragraph 35, wherein the growth factor is an interferon or a tumor necrosis factor.

38. The pharmaceutical composition of paragraph 37, wherein the growth factor is an interferon is IFN-α, IFN-γ, IL-2, IL-4, or IL-6.

39. A composition comprising a population of cells isolated from a mammal and poly-β-1→4-N-acetylglucosamine polymer, wherein the isolated cells are stored for at least 5 minutes.

40. The composition of paragraph 39, wherein the poly-β-1→4-N-acetylglucosamine polymer fibers are purified.

41. The composition of paragraph 39, wherein the poly-β-1→4-N-acetylglucosamine polymers are acetylated.

42. The composition of paragraph 39, wherein the poly-β-1→4-N-acetylglucosamine polymers are deacetylated.

43. The composition of paragraph 39, wherein the poly-β-1→4-N-acetylglucosamine polymers are free of protein, substantially free of other organic contaminants, and substantially free of inorganic contaminants.

44. The composition of paragraph 39, wherein the poly-β-1→4-N-acetylglucosamine polymers are semi-crystalline.

45. The composition of paragraph 39, wherein the poly-β-1→4-N-acetylglucosamine polymers are biodegradable and biocompatible.

46. The composition of paragraph 39, wherein the poly-β-1→4-N-acetylglucosamine polymer has a molecular weight of about 800,000 daltons to about 30 million daltons.

47. The composition of paragraph 39, wherein the poly-β-1→4-N-acetylglucosamine comprises semi-crystalline having a molecular weight of about 800,000 daltons to about 30 million daltons.

48. The composition of paragraph 39, wherein the poly-β-1→4-N-acetylglucosamine polymer has a molecular weight of about 10,000 daltons to about 800,000 daltons.

49. The composition of paragraph 39, wherein the poly-β-1→4-N-acetylglucosamine comprises semi-crystalline having a molecular weight of about 10,000 daltons to about 800,000 daltons.

50. A composition made by mixing an isolated population of primary mammalian cells and substantially purified polymer fibers which interact with the mammalian cells under conditions that the cells and the fibers interact.

51. A method for identifying a polymer fiber that forms complexes with cells that express GPIIIa and GPIb surface proteins comprising,
a) contacting cells with labeled GPIIIa and GPIb surface proteins;
b) eluting the proteins from the cells; and
c) and measuring the intensity or presence of the label;
such that fibers that bind the cells are identified.

52. A method for identifying polymers that form complexes with cells comprising,
a) labeling pGlcNAc polymer fiber;
b) mixing the labeled pGlcNAc polymer fiber with a test polymer fiber;
c) adding a population of cells to the mixed fiber sample and to a pure pGlcNAc sample;
d) placing the mixtures under conditions in which the binding between pGlcNAc and cells would normally occur;
e) eluting the mixture to remove unbound cells and fibers; and
f) comparing the amount of labeled pGlcNAc,
such that a polymer fiber that competitively inhibits binding of pGlcNAc to cells is identified.

53. A method for preserving a population of cells isolated from a mammal for later therapeutic use, the method comprising contacting said cells with a polymer fiber, such that a gel is formed, and freezing the gel for later applications.

54. A method of activating a population of cells isolated from a mammal, the method comprising contacting poly-β-1→4-N-acetylglucosamine polymer fibers to the cells, thereby activating the cells.

55. A method for accelerating wound healing a patient in need thereof comprising administering to a wound a composition comprising a population of cells isolated from a mammal and a polymer fiber, wherein the cells are derived from stored cells, and bind the polymer, such that wound healing is accelerated in the patient.

56. A method for reducing hemostasis time in a patient in need thereof comprising administering to a wound a composition comprising a population of cells isolated from a mammal and a polymer fiber that cells interact with, wherein the cells are derived from stored cells, such that hemostasis time is reduced in the patient.

57. The method of paragraph 55 or 56, wherein the cells are derived from the patient.

58. The method of paragraph 56 or 56, wherein the cells and polymer fibers are combined immediately prior to or in conjunction with administering the composition to the patient.

59. A method of identifying a candidate therapeutic agent or cell preservative, comprising:
(a) contacting pGlcNAc with a cell surface protein selected from the group consisting of band III, glycophorin A, GPIb, GPIIb, and alpha$_{2b}$beta$_3$, which cell surface protein is expressed on a cell surface and a test compound, under conditions that, in the absence of the test compound, allow pGlcNAc to bind to the cell surface protein and thereby form a pGlcNAc-cell surface protein complex; and
(b) determining whether pGlcNAc-cell surface protein complex formation is inhibited by the test compound;
wherein inhibition of pGlcNAc-cell surface protein complex formation by the test compound identifies the test compound as a candidate therapeutic agent or cell preservative.

60. The method of paragraph 59, wherein the pGlcNAc is contacted with the cell surface protein prior to contacting the pGlcNAc with the test compound.

61. The method of paragraph 59, wherein the pGlcNAc is contacted with the test compound prior to contacting the pGlcNAc with the cell surface protein.

62. The method of paragraph 59, wherein the cell surface protein is contacted with the test compound prior to contacting the pGlcNAc and the test compound.

63. The method of paragraph 59, wherein the pGlcNAc is a pGlcNAc fiber.

64. The method of paragraph 59, wherein the test compound is a fiber.

65. The method of paragraph 64, wherein the fiber is a polymer fiber.

66. The method of paragraph 64, wherein the fiber is a protein fiber.

67. The method of paragraph 66, wherein the protein is a human protein.

68. The method of paragraph 59, wherein determining whether pGlcNAc-cell surface protein complex formation is inhibited by the test compound comprises measuring the amount of binding between pGlcNAc and cell surface protein.

69. The method of paragraph 59, wherein determining whether pGlcNAc-cell surface protein complex formation is inhibited by the test compound comprises measuring the amount of binding between the test compound and cell surface protein.

70. The method of paragraph 59, wherein the method is performed in vitro.

71. The method of paragraph 59, wherein the method is performed in vivo.

72. The method of paragraph 59, wherein the cell surface is a platelet cell surface.

73. The method of paragraph 59, wherein the cell surface is a red blood cell surface.

74. The method of paragraph 59, further comprising: determining whether the test compound is capable of promoting hemostasis or accelerating the rate of wound healing, such that a test compound that is capable of promoting hemostasis or accelerating the rate of wound healing is a candidate therapeutic agent.

75. The method of paragraph 59, further comprising: determining whether the test compound is capable of forming a gel when mixed with platelets and, optionally, a 10% calcium chloride solution, such that a test compound that is capable of forming a gel is a candidate cell preservative.

76. The method of paragraph 59, further comprising, prior to step (a), identifying a suitable test compound by a method comprising:
(a) contacting pGlcNAc with the cell surface protein and a molecule, under conditions that, in the absence of the molecule, allow the pGlcNAc to bind to the cell surface protein and thereby form an pGlcNAc-cell surface protein complex; and
(b) determining whether pGlcNAc-cell surface protein complex formation is inhibited by the molecule;
wherein inhibition of pGlcNAc-cell surface protein complex formation by the molecule identifies the molecule as a suitable test compound.

77. The method of paragraph 76, wherein the pGlcNAc is contacted with the cell surface protein prior to contacting the pGlcNAc with the molecule.

78. The method of paragraph 76, wherein the pGlcNAc is contacted with the molecule prior to contacting the pGlcNAc with the cell surface protein.

79. The method of paragraph 76, wherein the cell surface protein is contacted with the molecule prior to contacting the pGlcNAc with the cell surface protein and the test compound.

80. The method of paragraph 76, wherein the cell surface protein is immobilized on a solid surface.

81. The method of paragraph 80, wherein the cell surface protein is present in a cell membrane, which cell membrane is immobilized on the solid surface.

82. A method of identifying a candidate therapeutic agent or cell preservative, comprising:
(a) contacting pGlcNAc with a test compound and a cell surface protein selected from the group consisting of band III, glycophorin A, GPIb, GPIIb, and alpha$_{2b}$beta$_3$, under conditions that, in the absence of the test compound, allow the pGlcNAc to bind to the cell surface protein and thereby form an pGlcNAc-cell surface protein complex; and
(b) determining whether pGlcNAc-cell surface protein complex formation is inhibited by the test compound;
wherein inhibition of pGlcNAc-cell surface protein complex formation by the test compound identifies the test compound as a candidate therapeutic agent or cell preservative.

83. The method of paragraph 82, wherein the pGlcNAc is contacted with the cell surface protein prior to contacting the pGlcNAc with the test compound.

84. The method of paragraph 82, wherein the pGlcNAc is contacted with the test compound prior to contacting the pGlcNAc with the cell surface protein.

85. The method of paragraph 82, wherein the cell surface protein is contacted with the test compound prior to contacting the pGlcNAc and the test compound.

86. The method of paragraph 82, wherein the pGlcNAc is a pGlcNAc fiber.

87. The method of paragraph 82, wherein the test compound is a fiber.

88. The method of paragraph 87, wherein the fiber is a polymer fiber.

89. The method of paragraph 87, wherein the fiber is a protein fiber.

90. The method of paragraph 89, wherein the protein is a human protein.

91. The method of paragraph 82, wherein determining whether pGlcNAc-cell surface protein complex formation is inhibited by the test compound comprises measuring the amount of binding between pGlcNAc and cell surface protein.

92. The method of paragraph 82, wherein determining whether pGlcNAc-cell surface protein complex formation is inhibited by the test compound comprises measuring the amount of binding between the test compound and cell surface protein.

93. The method of paragraph 82, further comprising: determining whether the test compound is capable of promoting hemostasis or accelerating the rate of wound healing, such that a test compound that is capable of promoting hemostasis or accelerating the rate of wound healing is a candidate therapeutic agent.

94. The method of paragraph 82, further comprising: determining whether the test compound is capable of forming a gel when mixed with platelets and, optionally, a 10% calcium chloride solution, such that a test compound that is capable of forming a gel is a candidate cell preservative.

6. EXAMPLE

Platelet-pGlcNAc Gels

Platelet-pGlcNAc gels were produced by various combinations of pGlcNAc, platelets and calcium salt solutions. The results presented herein provide support for the compositions of the invention.

Materials and Methods

Two approaches have been utilized to prepare platelets for use in the compositions and methods of the invention. One approach used high yield platelets obtained from the American Red Cross, Northeast. The platelets were obtained by plateletpheresis procedures performed using the Baxter Amicus Instrument and the Cobe Spectra Instrument. The other approach was to isolate platelet-rich plasma from CPD whole blood collected at Oklahoma Blood Institute. Both platelet procedures were leukoreduced. Another approach is to obtain platelet rich plasma from a patient through a platelet separator such as the Medtronic Magellan™ Autologous Platelet Separator. The Magellan separator is an automated system that uses density differences and gentle centrifugal forces to separate platelet-rich plasma containing important growth factors from a blood sample and deposits these components into a separate sterile syringe. The system is unique in that it requires a very small sample of the patient's blood (30-60 cc) and delivers the consistent platelet-rich plasma physicians desire. Surgeons can mix the platelet-rich plasma with an activator, such as pGlcNAc, for a variety of applications and clinical procedures, depending on the patient's needs.

High yield platelets received from the American Red Cross were stored at 22° C. with agitation for 4-10 days. The platelet-rich plasma (PRP) was sampled for measurement of platelet count and then processed in several ways to produce a therapeutic applications. First, no gel was produced, simply platelet rich plasma was produced by ultra-centrifuge. Blood samples were centrifuged at 10 ml aliquot of the PRP at 20,000 rpm for 10 minutes to obtain cell-free plasma. Second, a frozen control was produced by freezing and thawing a 10 ml aliquot of PRP on 10 occasions; the aliquot sample was then centrifuged at 20,000 rpm for 10 minutes to obtain cell-free plasma. Third, a calcium treated composition was produced by adding 0.25 ml of 10% calcium chloride ($CaCl_2$) to a 10 ml aliquot of PRP which was then incubated at room temperature for 30 minutes. After 30 minutes, centrifuge at 20,000 rpm for 10 minutes to obtain cell-free plasma. Fifth, a thrombin composition was produced by adding 5000 units of bovine thrombin to a 10 ml aliquot of PRP and the mixture was then incubated at room temperature for 30 minutes. The samples were centrifuged at 20,000 rpm for 10 minutes to obtain cell-free plasma. Sixth, a CaCl/thrombin treated composition was produced by adding 0.25 ml of calcium chloride and 5000 units of bovine thrombin to a 10 ml aliquot of PRP which was incubated at room temperature for 30 minutes. The mixture was them centrifuged at 20,000 rpm for 10 minutes to obtain cell-free plasma. Seventh, a pGlcNAc slurry treated composition was produced by adding 0.125 ml of calcium chloride and 5 ml of pGlcNAc slurry (1 mg fibers/ml distilled $H_2O$) to 5 ml of PRP. The mixture was then incubated at room temperature for 30 minutes and then centrifuged at 20,000 rpm for 10 minutes to obtain cell-free plasma. Eighth, a pGlcNAc slurry/CaCl treated composition was produced by adding 0.125 ml of calcium chloride and 5 ml of pGlcNAc slurry (1 mg/ml) to a 5 ml aliquot of PRP. The mixture was incubated at room temperature for 30 minutes and centrifuged at 20,000 rpm for 10 minutes to obtain cell-free plasma.

Results $CaCl_2$ was needed to produce a platelet gel when PRP was treated with pGlcNAc. The platelet gel was produced by pGlcNAc and $CaCl_2$ at a rate similar to gel produced by thrombin and $CaCl_2$. In order to examine gel formation, the platelet-rich plasma was then placed on a petri dish and treated with pGlcNAc and $CaCl_2$. The mixture produced a platelet gel within three minutes with manual agitation. The pGlcNAc slurry used in this study was 1 mg/ml of distilled water. Similar results were achieved using 1 mg pGlcNAc per 1.0 ml of 0.9% NaCl and using 2 mg pGlcNAc per 1.0 ml of 0.9% NaCl.

Conclusion

Gels comprising pGlcNAc and platelets can be successfully produced by a variety of methods. Based on the results, the most effective methods include the addition of calcium salt solutions in production of a pGlcNAc-platelet gel. The gels produced as described above can be used in a variety of therapeutic applications, and are particularly advantageous over present applications in that they make use of stored platelets which are currently disposed of after expiration for transfusion purposes.

7. EXAMPLE

Platelets Adhere to pGlcNAc Polymers to Form Polymer-Cell Macroaggregates with Various Platelet/pGlcNAc Ratios The Example presented herein describes the successful identification of an aggregation interaction between platelets and pGlcNAc. The experiments presented herein form the basis for methods of the present invention that relate to production of the compositions of the invention. In particular, the results form the basis of the ratio of platelets to pGlcNAc found in the compositions of the invention having various formulations. The invention also relates to methods for making the compositions of the invention and the efficiency of such methods.

Material and Methods

Both fresh and stored platelets were labeled with the fourophore CMFDA (Fischer et al., 2001, Art. Cell. Blood Subs. 1 mm. Biotech. in press). Fresh platelets and pGlcNAc were mixed in different ratios, including about $2 \times 10^6$ platelets per mg of pGlcNAc and $7 \times 10^7$ platelets per mg of pGlcNAc, wherein, in both instances, the pGlcNAc was deacetylated and formulated as a sponge. Stored platelets and pGlcNAc were also mixed in a ratio of about $5.4 \times 10^8$ platelets per mg of pGlcNAc, wherein the pGlcNAc was fully acetylated slurry. The mixtures were reacted at room temperature in Tyrode's buffer with divalent cations. The resulting platelet-pGlcNAc networks were washed 5× over a 15 min period with Tyrode's buffer to remove unattached platelets, and then platelet contents were estimated by comparing relative flourescent intensities.

Results

The data in FIG. 1 shows that by varying the ratio of platelets to pGlcNAc in interaction reactions, the platelet content of the resulting platelet-pGlcNAc matrix can be proportionally varied over a wide range. Different ratios of fluorescent-labeled platelets and deacetylated pGlcNAc were allowed to react and then non-bound cells were removed by extensively washing with physiological buffer. The number of platelets retained on the polysaccharide was quantified with fluorescence. The highest ratio of platelets to pGlcNAc was $5.4 \times 10^8$ cells/mg pGlcNAc (corresponding to a total intracellular volume of about 5.4 ul/mg pGlcNAc). This value, however, was by no means the limit.

Conclusion

The results indicate that platelet-pGlcNAc networks can be formed with unlimited platelet contents if small amounts of pGlcNAc are incorporated into large platelet-platelet aggregates. The ratio of platelets to pGlcNAc can be controlled by the quantity of platelets added, as well as the formulation of the pGlcNAc and the age of the platelets. The results demonstrate that by providing support for the ratios of platelets to pGlcNAc in the compositions of the invention. Thus, an understanding of the amount of pGlcNAc and platelets that can be mixed together effectively to form a composition was achieved.

8. EXAMPLE

Platelets Adhere More Readily to Deacetylated Than Fully Acetylated pGlcNAc networks and to Sponge as Compared to Membrane Formulations The Example presented herein describes the successful interaction between platelets and various pGlcNAc formulations and variations. The experiments presented herein form the basis for methods of the present invention that relate to production of the compositions of the invention. In particular, the results form the basis for the ratios used in production of compositions of varying formulations.
Materials and Methods Fresh (gel filtered) platelets were incubated with four different pGlcNAc polymer formulations to determine the relative "loading" efficiencies of the matrixes. The four formulations were deacetylated sponge, deacetylated membrane, acetylated sponge, and acetylated membrane. After incubating the fluorescent-labeled platelets in physiological buffer and exhaustively washing off the excess cells, the bound platelets were quantified by measuring relative fluorescence.
Results The fluorescence analysis showed that platelets most readily attach to the cationic, deacetylated polymer. The data shown in FIG. 2A represents a comparison of the number of platelets ($\times 10^7$) per mg of pGlcNAc. Deacetylated and acetylated sponge formulations of pGlcNAc bound greater numbers of platelets than the deacetylated and acetylated membrane formulations. The deacetylated membrane bound more platelets than the acetylated membrane. The deacetylated sponge bound at least two times more platelets than the acetylated sponge. FIG. 2B shows the relative degree of fluorescence observed in the four formulations of pGlcNAc.
Conclusion This result suggests an ionic interaction between the polysaccharide and negatively charged proteins and lipids on the cell surface. The enhanced attachment of platelets to sponge as compared to membrane preparations might be due to physical differences in fiber porosity. The results demonstrate that by providing the number of platelets cells that can effectively be mixed with the four formulations of pGlcNAc analyzed the ratio of cells to pGlcNAc fibers can be controlled.

9. EXAMPLE

Platelets Activate when they Contact pGlcNAc Polymers

The high platelet/pGlcNAc ratios that can be obtain is evidence that contact of the cells with the polymer leads to platelet activation. In the experiment presented herein, scanning and fluorescent microscopy was performed to confirm that the contact of platelets with the polysaccharide leads to cell activation. These experiments for the basis of the methods of the invention and the compositions of the invention. In particular, the experiments form the basis of methods for activating and/or aggregating cells, which can have added benefit in certain therapeutic uses where such activated and/or aggregated cells are needed.
Materials and Methods Platelets were isolated from fresh blood with differential centrifugation and gel filtration as described above in Example 6. The platelets were then mixed with fully acetylated pGlcNAc slurry in Tyrode's buffer with divalent ions. After a five minute incubation at room temperature, Mab anti-p-selectin-PE was added to label the cells for surface exposure of the alpha granule protein p-selectin. Samples were quenched for electron and fluorescene microscopy with ice cold 2% paraformadehyde. Scanning electron microscopy (SEM) was used to examine activation state of the cells. An example of such microscopy is sputter-coating the sample with gold and viewing with a scanning electron microscope such as a Phillips (Eindhoven, The Netherlands) XL30 Field Emission Gun scanning electron microscope at 3 kV, though any technique known to those of skill in the art can be used.

Platelets on lyophilized pGlcNAc-platelet compositions were also examined using SEM.
Results The scanning electron micrograph in FIG. 3 (panel A) clearly shows that platelets bound to pGlcNAc fibers displayed an activated, non-discoidal morphology with extended pseudopodia. Furthermore, incubation of the platelet-pGlcNAc compositions with a PE-conjugated monoclonal antibody to p-selectin revealed (FIG. 3, panel B) that the cells contacting the polymer were activated (at least) to the extent that alpha granule contents, including p-selectin, were surface exposed. Similar results have been obtained with fluorescent antibodies to the activated conformation of $alpha_{2b}beta_3$ (see Example 10 below).

The SEM results for platelets on lyophilized pGlcNAc-platelet compositions is shown in FIG. 5. The lyophilized platelets retained their activated morphology on pGlcNAc.
Conclusion These results indicate that the interaction of pGlcNAc with platelets results in activated cell morphology that appears similar to that observed when platelets interact with other materials, including glass (e.g., Rozenberg and Stormorken, 1967, Scand. J. Clinic. Lab. Invest. 19:82-85; Coller et al., 1983, J. Clin. Invest. 72:325-338), polylysine (e.g., Kinlough-Rathbone et al., 1977, Thromb. Haem. 37:291-308; Ishihara et al., 1994, J. Biomedical Materials Res. 28:1347-1355), plastics (e.g., Goodman et al., 1993, J. Biomedical Materials Res. 27:683-695) and metals (De Scheerde et al., 1998, Seminars in Interventional Cardiology 3:139-144). The results undeniably demonstrate the activation of platelets by pGlcNAc and the aggregation of platelets in upon interaction with pGlcNAc, lending support to methods for achieving such and the compositions based on the fact that the interactions occur when polymer fibers and cells interact.

10. EXAMPLE

Platelets Adhesion to pGlcNAc Polymers in Part Involves $Alpha_{2b}$, $Beta_3$ Glycoprotien IIb-IIIa Complex Three studies were performed to determine if absorbed adhesive proteins and their cell surface proteins might be involved in contact activation of platelets by the polysaccharide. First, the extent to which deacetylated pGlcNAc absorbed plasma proteins was examined. Second, it was examined whether RGD-containing $alpha_{2b}beta_3$ inhibitors echistatin and integrilin inhibited the adhesion of platelets to deacetylated pGlcNAc polymers. Third, deacetylated pGlcNAc was used as an "affinity" matrix to absorb platelet surface proteins that are potentially involved in the interaction of platelets and pGlcNAc.
Materials and Methods For the second study, deacetylated pGlcNAc sponge was incubated with excess human plasma (1.0 ml plasma/10.3 mg deacetylated pGlcNAc sponge) and then exhaustively washed to remove unbound proteins. The matrix was placed in SDS and beta-ME, boiled and electrophoresed.

For the second study, fresh gel filtered platelets (fluorescent-labeled) were treated with echistatin, the stable prostacyclin analogue Iloprost (a powerful activator of the cAMP signal for general platelet inhibition), integrilin, or control buffer. Inhibitors of contact activation factor XIIa (corn trypsin inhibitor) and thrombin (heparin) were included in some samples to probe for specific interaction mechanisms.

The cells were then mixed with deacetylated pGlcNAc sponges in the presence of divalent cations, and then extensively washed to remove unbound platelets. The platelet content of the resulting platelet-pGlcNAc networks were then measured with fluorescence. The effect of pGlcNAc on fibrin-gel formation and clot retraction was also recorded.

For the third study, native and denaturing detergent extractions were performed. To isolate pGlcNAc-associated proteins in a native state, platelet-pGlcNAc networks (the "no inhibitor" buffer control preparation from the second study, described above) were exhaustively washed with ice-cold Tyrode's buffer containing 1% deoxycholate and 1% TX-100. This detergent extraction was designed to solubilized and remove unbound membrane components, while maintaining pGlcNAc-cell surface protein complexes in an approximately native conformation. The extracted platelet-pGlcNAc complexes were subjected to SDS-PAG electrophoresis to resolve pGlcNAc-bound proteins.

Another very stringent denaturing type of extraction was performed to directly identify platelet surface proteins that are within about 20 angstroms of the polysaccharide. After obtaining platelet-pGlcNAc networks, the interaction of pGlcNAc with near-by proteins was covalently fixed by reacting the mixture with the disulfide-reducible cross-linker DTSSB (dithiobis[sulfosuccinimidylpropionate]). The cross-linked platelet-pGlcNAc aggregate was then extracted exhaustively with Tyrode's buffer that contained 4% SDS at 100° C.; these are strong denaturing conditions that should leave only covalent pGlcNAc-platelet protein complexes intact. The SDS extracted samples were then subjected to SDS-PAG electrophoresis under reducing conditions (to release the pGlcNAc-bound proteins) for the identification of proteins.

Results

For the first study, the resulting total protein stain of the bound plasma proteins (Lane 1, FIG. 4B) and the initial plasma sample (Lane 2, FIG. 4B) as determined by SDS-PAG indicated that a wide range of plasma proteins absorbed to the polysaccharide. Based on the density of the total protein stain, about 0.1 mg plasma protein/mg pGlcNAc was bound.

For the second study, the results in FIG. 4A show that inhibition of $alpha_{2b}beta_3$ function with echistatin significantly reduced platelet adhesion to the polysaccharide in comparison to the control buffer (carrier). The $alpha_{2b}beta_3$ antagonists, corn trypsin inhibitor and heparin also partially inhibited the interaction of platelets with pGlcNAc. The pGlcNAc fibers accelerated fibrin polymerization and participated in platelet-driven clot retraction of pGlcNAc-fibrin-platelet macro-aggregates.

For the third study, The principle result of this analysis is that proteins that co-migrated with $alpha_{2b}$, $beta_3$, the fibrinogen chains and actin were absorbed to the pGlcNAc (see lane 3 in FIG. 4 B, confirming pGlcNAc-bound proteins by SDS-PAG).

The results of the more stringent denaturing followed by SDS-PAG electrophoresis are show in lanes 4 and 5, FIG. 4 B. The von Willebrand factor (vWf) GPIb, GPIIb, GP IIIa and the fibrinogen $alpha_{2b}beta_3$ surface proteins bound the pGlcNAc. As was the case with the native state affinity absorption, proteins that co-migrated with $alpha_{2b}beta_3$, the fibrinogen chains and actin were cross-linked to the polymer. Higher resolution 2D IEF-SDS-PAG electrophoresis and Western analysis would definitively confirm the identify of the absorbed proteins.

Conclusion

These results provide preliminary evidence that the interaction of pGlcNAc with platelets is in part mediated by specific interactions with fibrinogen-$alpha_{2b}beta_3$ complexes and perhaps other cell surface proteins. These findings form the basis for the more complete elucidation of the platelet-pGlcNAc interaction mechanisms described herein. Such interactions support the methods of the invention of identifying fibers that interact with human cells, as well as cells types that interact with pGlcNAc. The results related to fibrin and clot retraction support the effectiveness of methods of the invention for healing wounds and promoting hemostasis.

11. EXAMPLE

Proteins on the Platelet Surface that Mediate the Interaction of Platelets Cells with pGlcNAc Platelet cell surface proteins were examined for to determine if such proteins could form complexes with pGlcNAc.

Materials and Methods

In order to directly identify platelet surface proteins that are within about 20 angstroms of the polysaccharide. After obtaining platelet-pGlcNAc networks, the interaction of pGlcNAc with near-by proteins was covalently fixed by reacting the mixture with the disulfide-reducible cross-linker DTSSB (dithiobis[sulfosuccinimidylpropionate]). The cross-linked platelet-pGlcNAc aggregate was then extracted exhaustively with Tyrode's buffer that contained 4% SDS at 100° C.; these are strong denaturing conditions that should leave only covalent pGlcNAc-platelet protein complexes intact. The SDS extracted samples were then subjected to SDS-PAG electrophoresis under educing conditions (to release the pGlcNAc-bound proteins) for the identification of proteins.

Western blots were then performed with anti-GPIIIa and anti-GPI antibodies to confirm the presence of cell surface proteins.

Results

Conclusion

Platelet surface proteins interact with pGlcNAc fibers through GPIIb/IIb and GPIb/V/IX, providing support for the methods and compositions of the invention, wherein the composition comprises platelets complexed to, and interacting with, polymer fibers.

12. EXAMPLE

Proteins on the Red Blood Cell Surface that Mediate the Interaction of Red Blood Cells with pGlcNAc Red blood cell surface proteins were examined for to determine if such proteins could form complexes with pGlcNAc.

Materials and Methods

In order to directly identify red blood cell surface proteins that are within about 20 angstroms of the polysaccharide. After obtaining red blood cell-pGlcNAc networks, the interaction of pGlcNAc with near-by proteins was covalently fixed by reacting the mixture with the disulfide-reducible cross-linker DTSSB (dithiobis[sulfosuccinimidylpropionate]). The cross-linked red blood cell-pGlcNAc aggregate was then extracted exhaustively with Tyrode's buffer that contained 4% SDS at 100° C.; these are strong denaturing conditions that should leave only covalent pGlcNAc-red blood cell protein complexes intact. The SDS extracted samples were then subjected to SDS-PAG electrophoresis under reducing conditions (to release the pGlcNAc-bound proteins) for the identification of proteins.

Western blots were then performed with anti-Band II and anti-glycophorin A antibodies to confirm the presence of cell surface proteins.

Results

Figure 8:
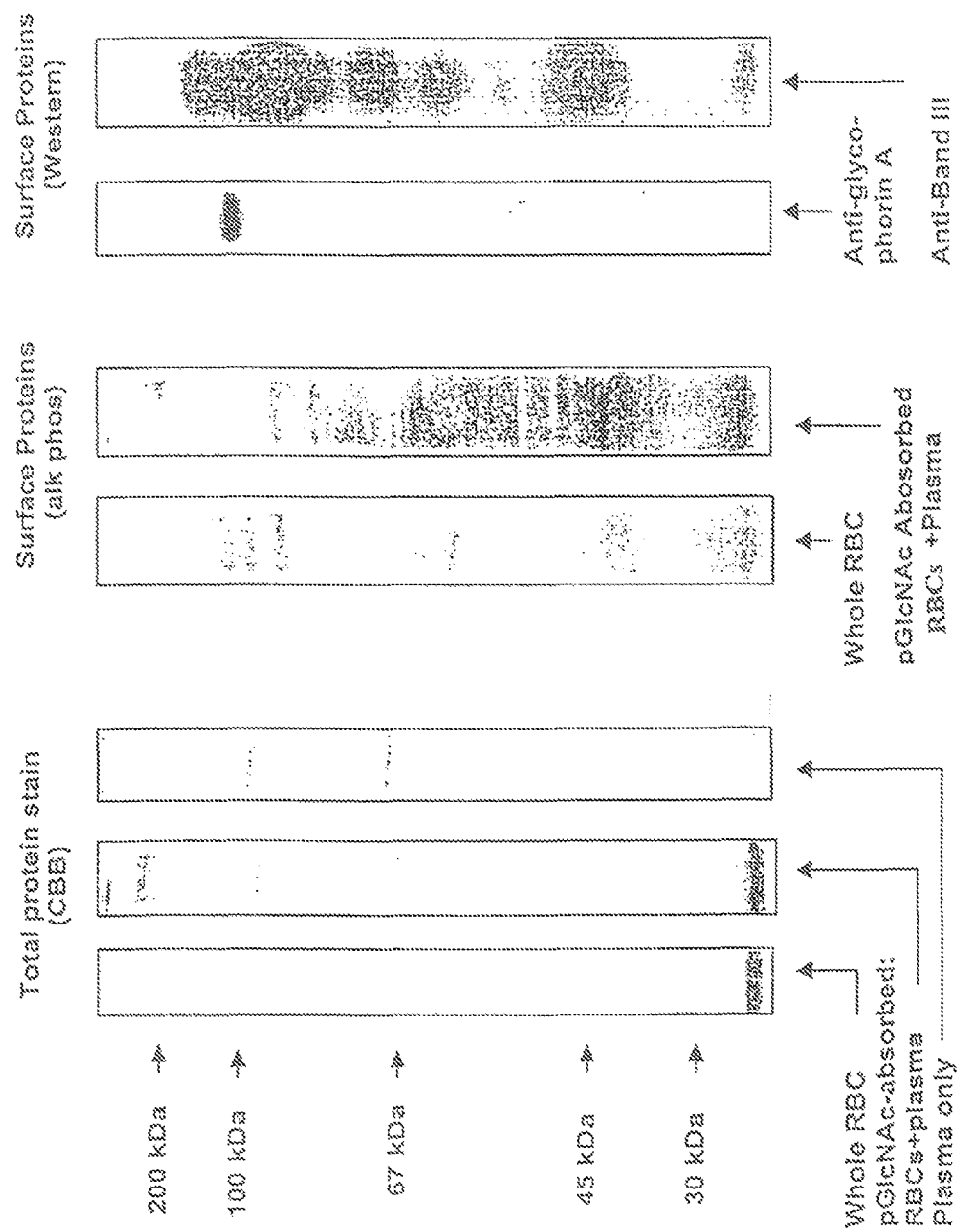

FIG. 8, lanes 1-3, show total protein derived from red blood cells stained with colloidal Coomassie stain (CCB). Lane 1 shows protein from whole red blood cells, lane 2 shows red blood cells and plasma derived from samples absorbed by pGlcNAc, and lane 3 shows plasma alone derived from a sample absorbed by pGlcNAc polymer fibers. Lanes 4 and 5 show red blood cell surface proteins stained with streptaviden-alkaline phosphatase (alk phos). Lane 4 shows surface proteins from whole red blood cells, and lane 5 shows surface proteins derived from a sample absorbed by pGlcNAc polymer fibers. Lanes 6 and 7 show Western blots using anti-glycophorin A (lane 6) and anti-band III antibodies (lane 7) to confirm the presence of red blood cell surface proteins associated with pGlcNAc.

Figure 9:
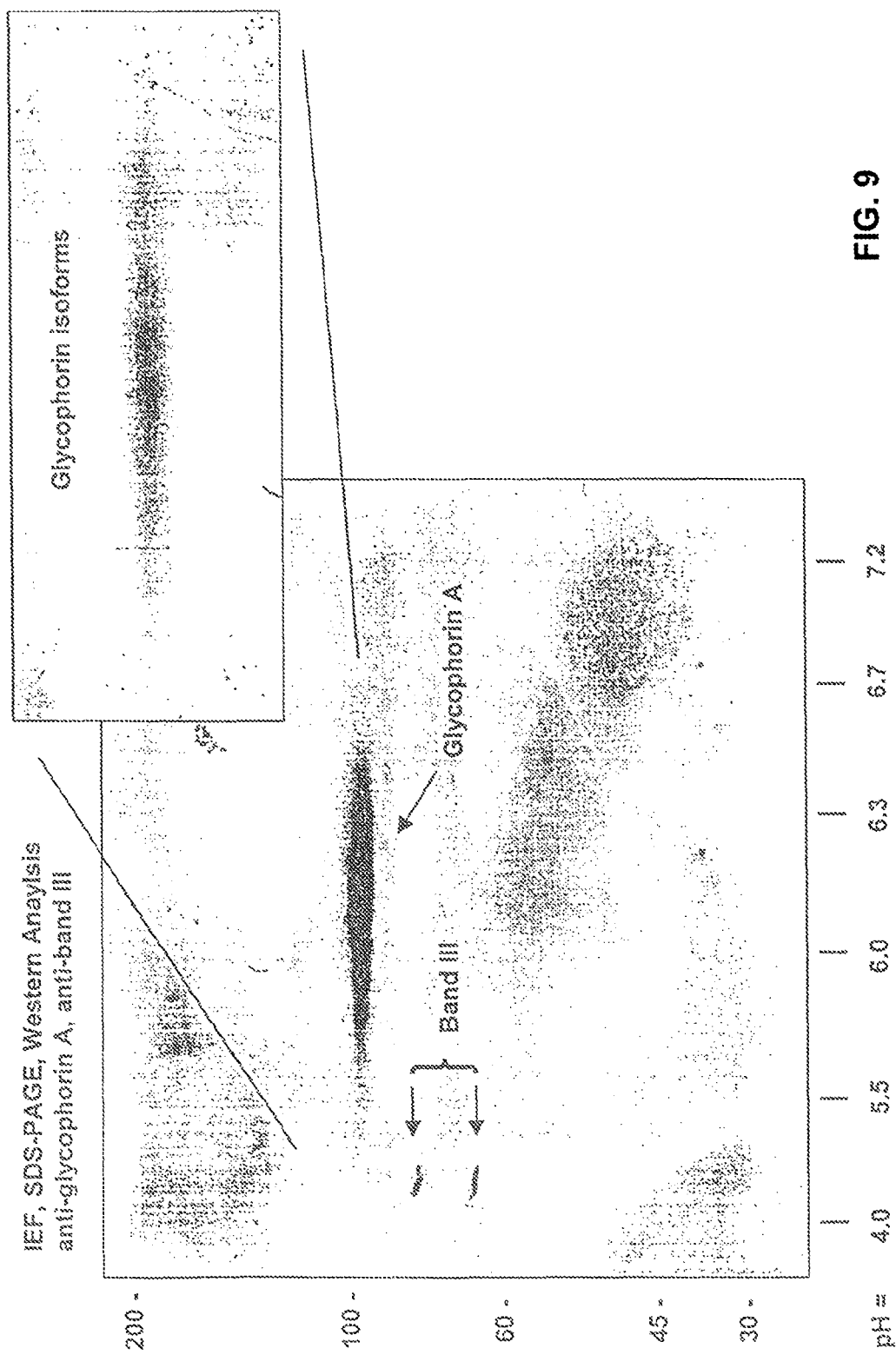

FIG. 9 shows Western blot analysis using anti-glycophorin A and anti-band III antibodies conriming red blood cell surface proteins were absorbed by pGlcNAc polymer fiber.

Conclusion

Red blood cell surface proteins interact with pGlcNAc fibers through glycophorin A anti-band III, providing support for the methods and compositions of the invention, wherein the composition comprises red blood cells complexed to, and interacting with, polymer fibers.

13. EXAMPLE

Examination of Interaction pGlcNAc and Platelets

Additional studies are performed to examine the potential importance of the plasma protein absorption/cell surface protein activation process in platelet activation by pGlcNAc. Fresh platelets are subjected to size-exclusion chromatography to free the cells form unbound plasma proteins. This allows one to probe for direct platelet-pGlcNAc interactions that do not involve absorption of "sticky" plasma proteins to the polymer. However, the surface of resting platelets binds considerable quantities of fibrinogen, vWF and other adhesive proteins. The preliminary data suggests that these bound adhesive proteins in part mediate an interaction with pGlcNAc fibers. While the following experiments are designed to specifically analyze the platelet-pGlcNAc interactions (and not the binding of bulk plasma proteins to the marine polymer), additional studies can be formulated for examining the platelet-pGlcNAc interaction in whole blood.

The goal of these studies is to identify the proteins on the platelet surface that mediate the interaction of platelets with the glucosamine polymer. Confocal microscopy with fluorescent antibody probes to specific platelet membrane complexes as well as biochemical affinity absorption methods are used. These studies are performed in the presence and absence of specific inhibitors of the $alpha_{2b}beta_3$-fibrinogen interaction, the GPIb/IX-vWF interaction and the p-selectin-p-selectin glycoprotein ligand interaction.

First Study
Materials and Methods

Fresh gel filtered platelets is incubated with pGlcNAc (deacetylated and fully acetylated) fibers for 15 min, and then fluorescent probes (listed below) for platelet molecules are added. After an additional 15 min incubation period, samples are quenched for confocal microscopy. The confocal analysis emphasizes imaging of focal planes in which the polysaccharides contact the cells. Probes that are used to identify the various surface proteins are presented in Table 1.

TABLE 1

| Surface protein/lipid | Probe |
| --- | --- |
| $alpha_{2b}beta_3$ (activated) | Mab PAC-1-FITC (Becton-Dickonson) |
| $alpha_{2b}beta_3$ (activated) | Mab PAC-1-FITC (Becton-Dickonson) |
| $beta_3$ (activation independent) | Mab VI-PL2-perPC (Becton-Dickonson) |
| GPIb | Mab AN51-PE (Dako) |
| p-selectin | Mab AK-3-PE (Becton-Dickonson) |
| fibrinogen | polyclonal ab-FITC F0111 (DAKO) |
| fibronectin | polyclonal ab-FITC A0245 (DAKO) |
| vWF | polyclonal ab-FITC A0082 (DAKO) |
| thrombomodulin | Mab 617-FITC (DAKO) |
| phosphatidyl serine | Annexin V-FITC (Sigma) |

Conclusion

Such experiments are used to confirm the preliminary results presented herein and determine definitively that $alpha_{2b}beta_3$, GP1b, p-selectin and/or phosphatidyl serine localize to points of contact between pGlcNAc and platelets.

Second Study

Figure 1:
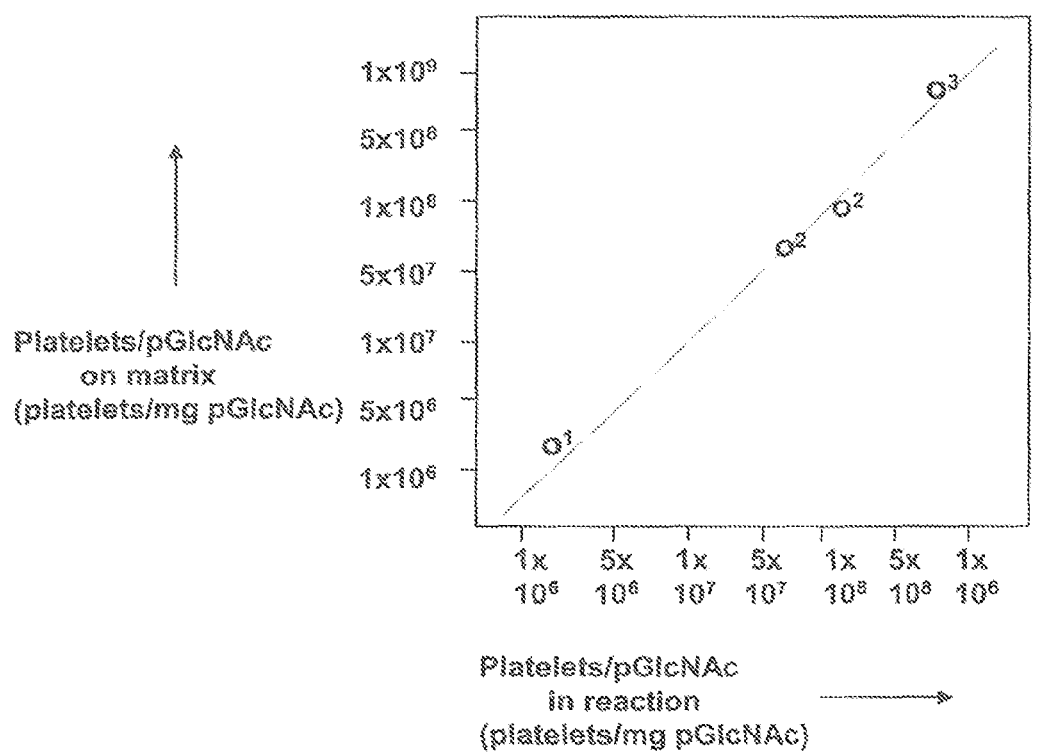
Figure 2A:
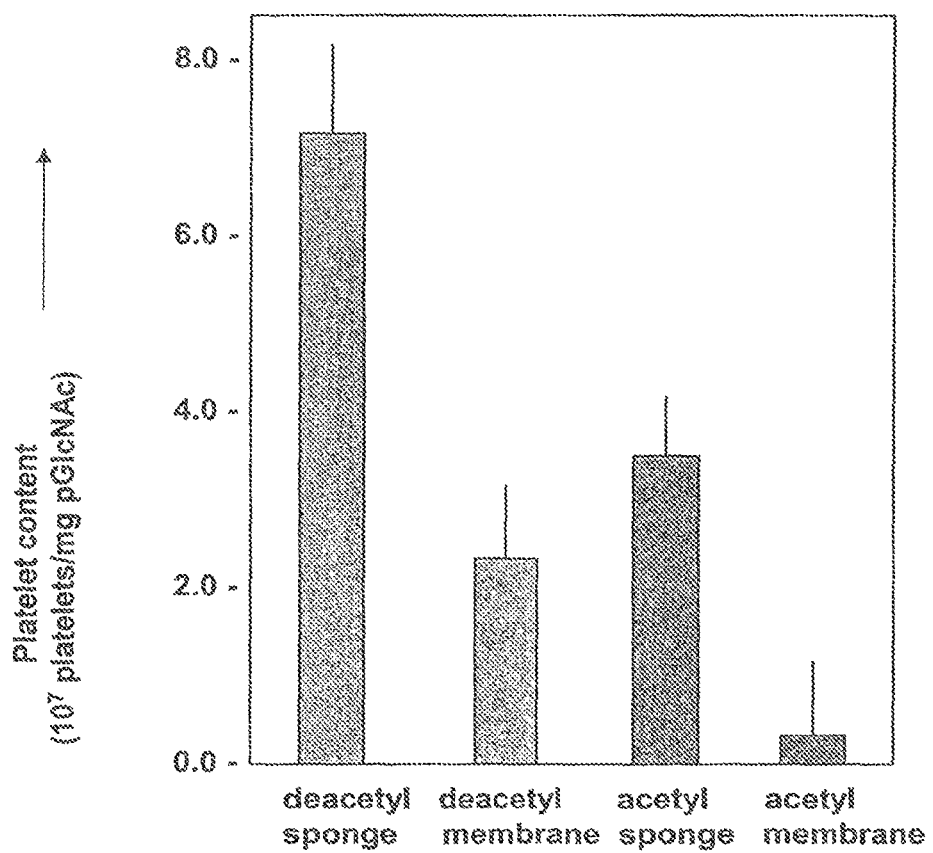
Figure 2B:
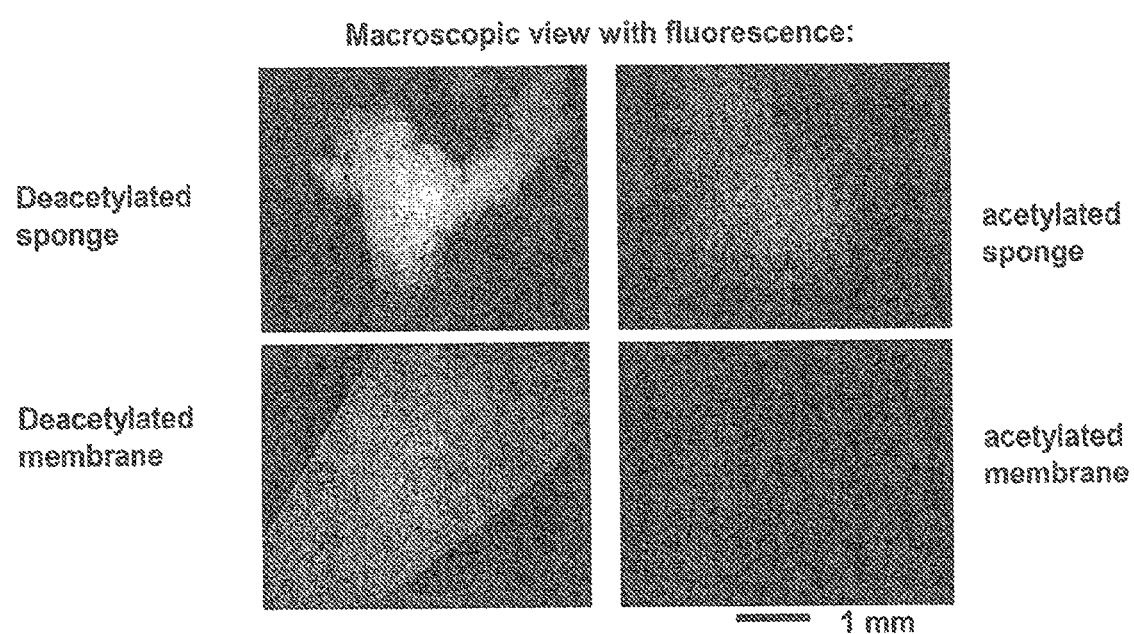
Figure 3A:
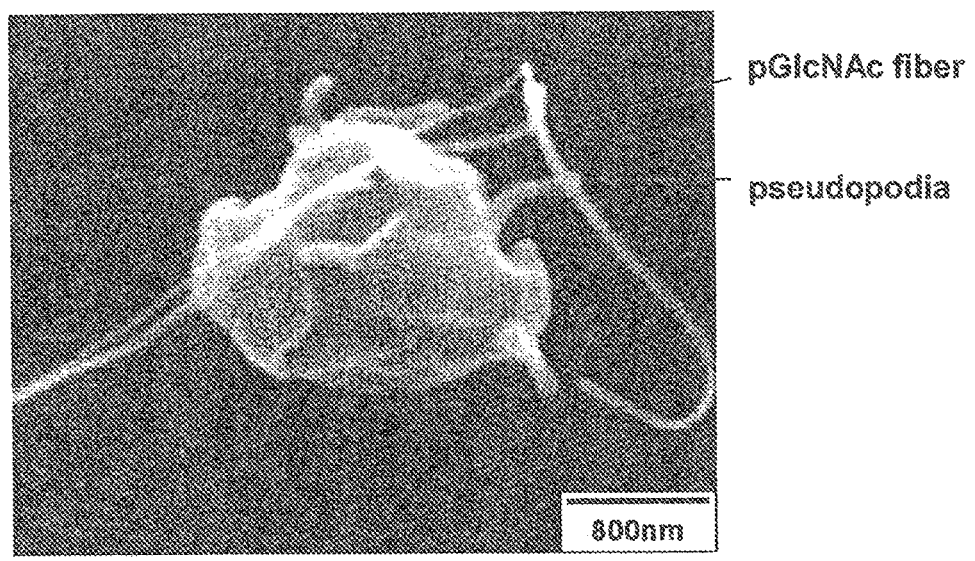
Figure 3B:
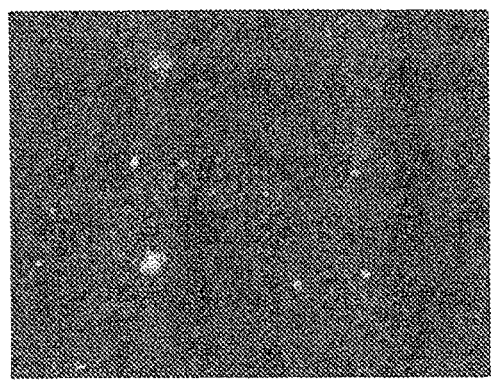
Figure 3B:
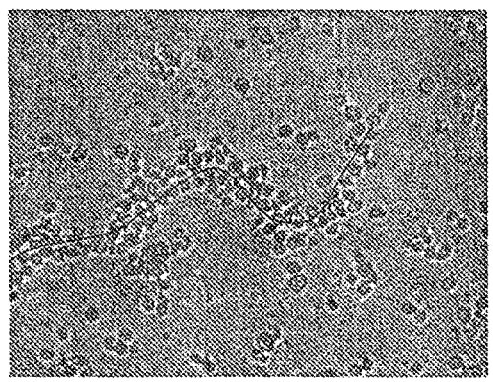
Figure 4A:
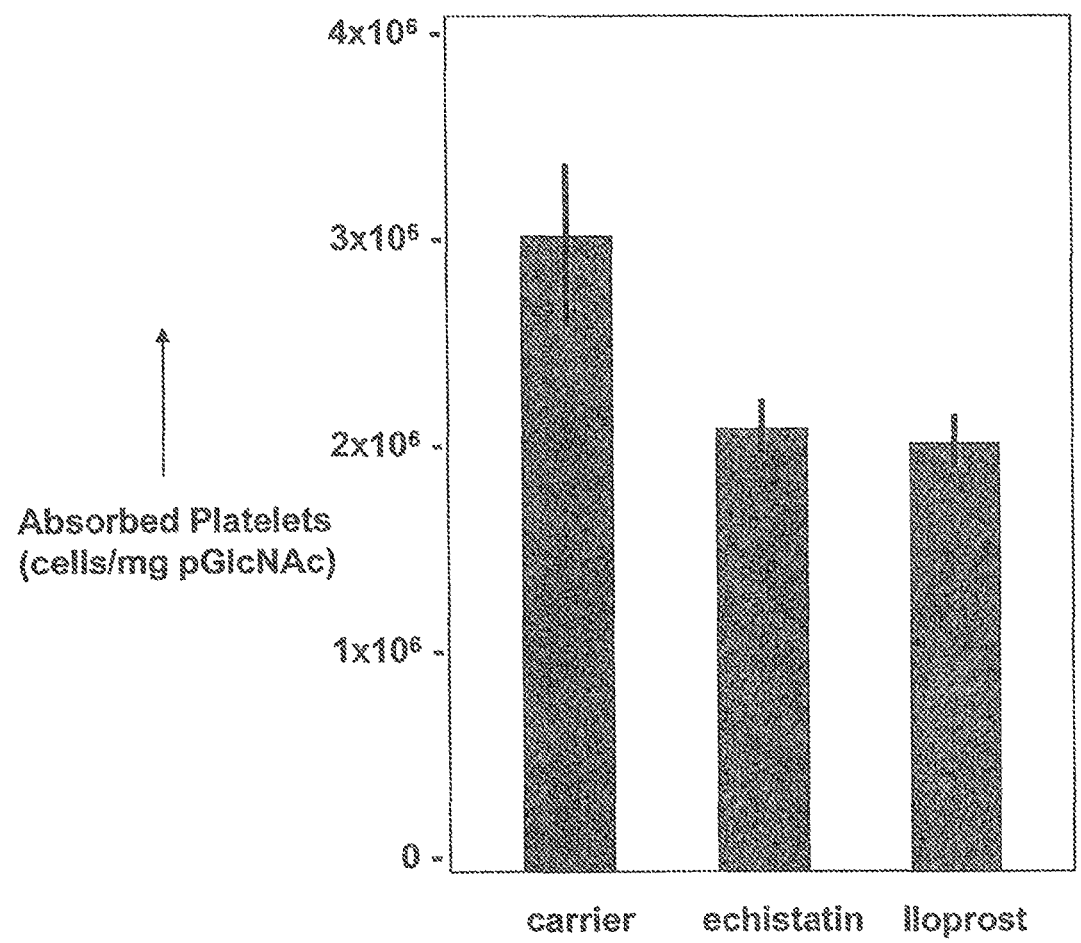
Figure 4B:
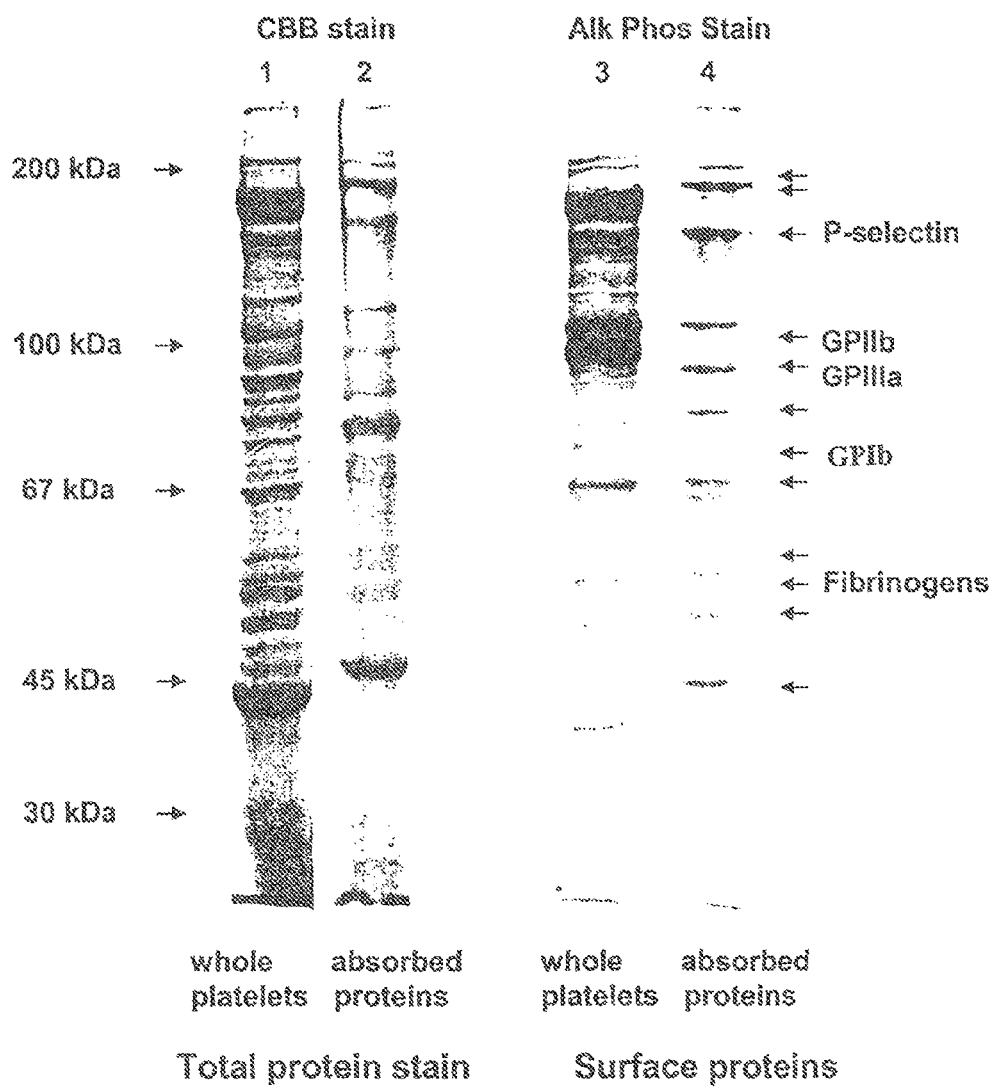
Figure 5:
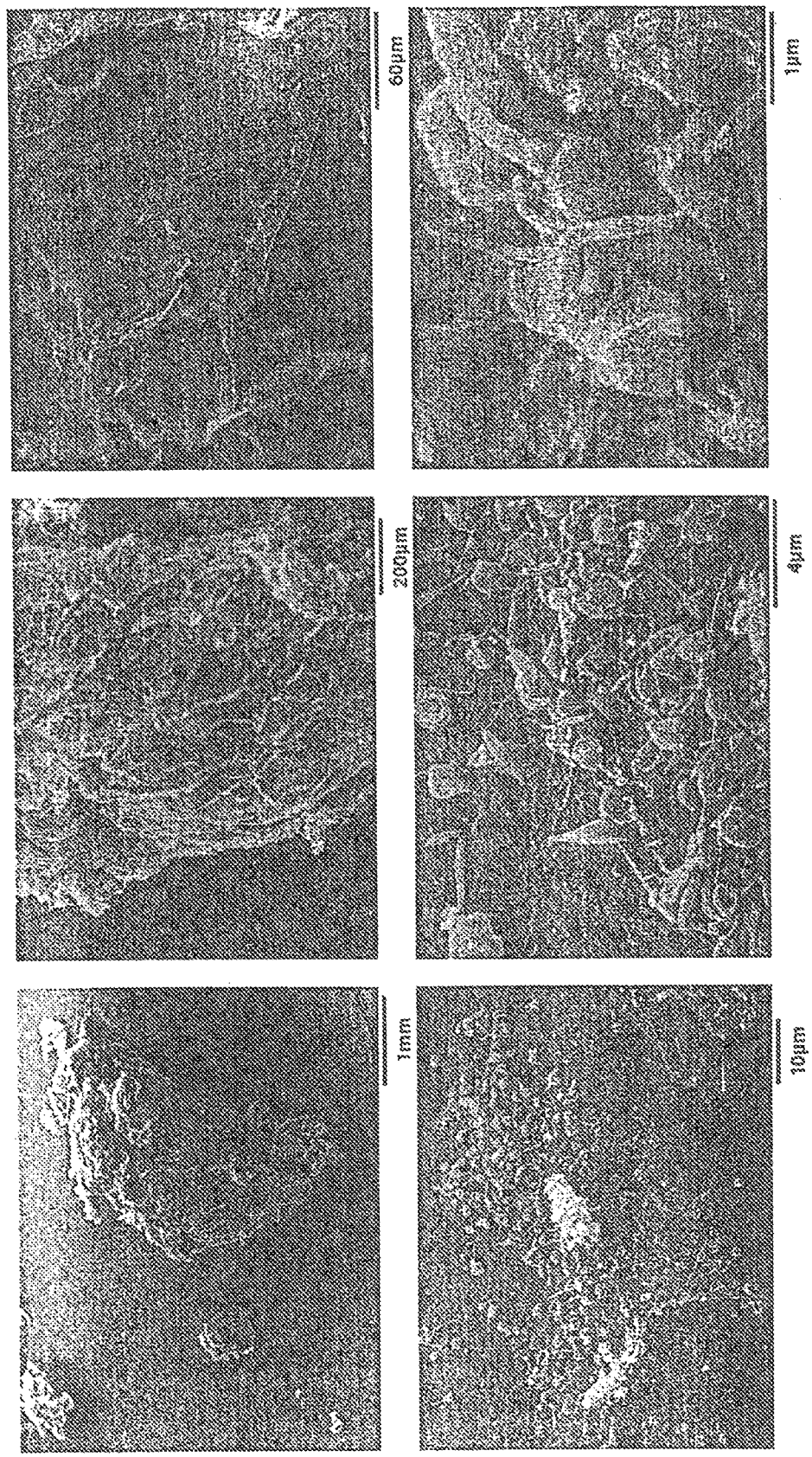
Figure 6:
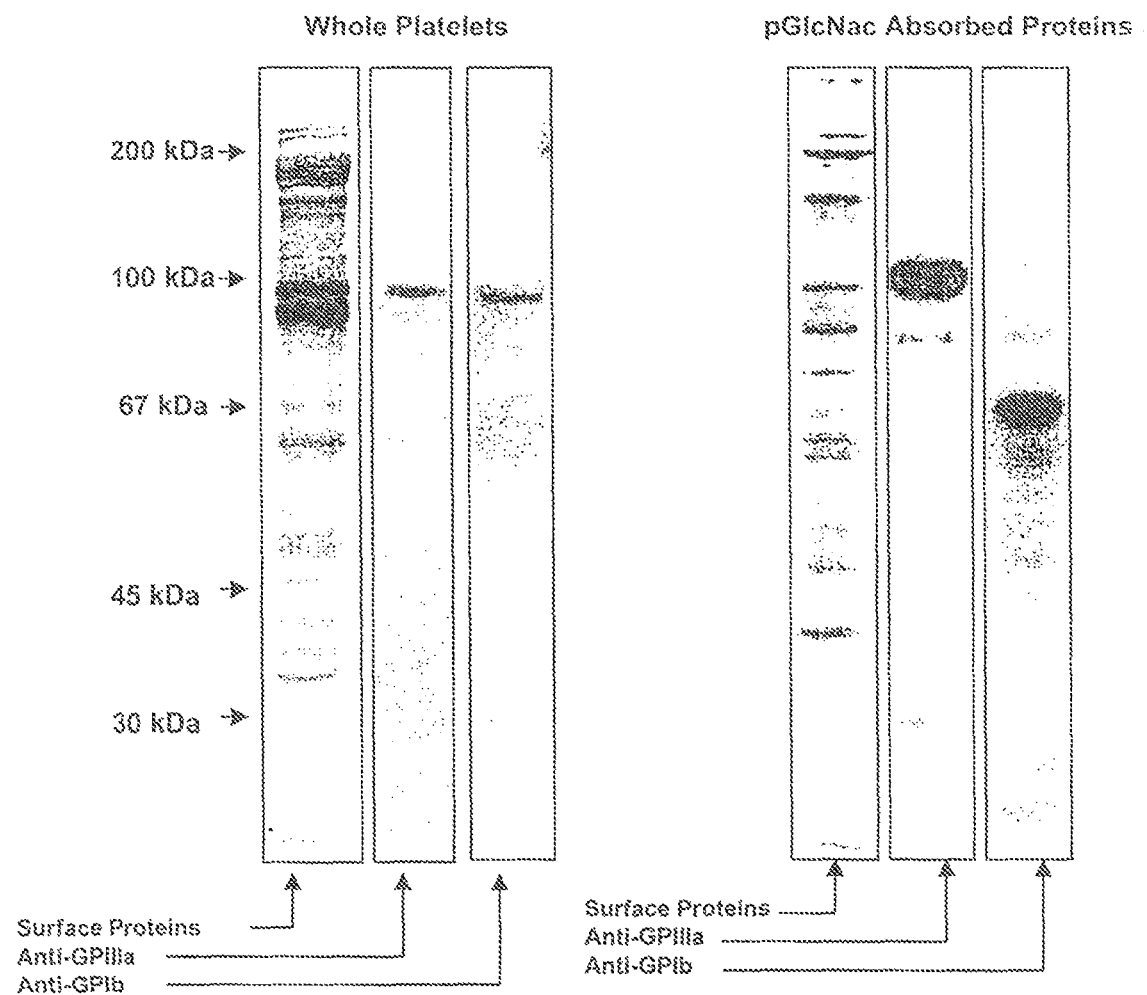
FIG. 6 shows show SDS-PAG electrophoresis of Glycoprotein IIb, IIa and Ib/V/IX complexes derived from whole platelets (lanes 1-3). Lanes 4-6 show SDS-PAG electrophoresis of Glycoprotein IIb, IIa and Ib/V/IX complexes derived from pGlcNAc absorbed proteins.
Figure 7:
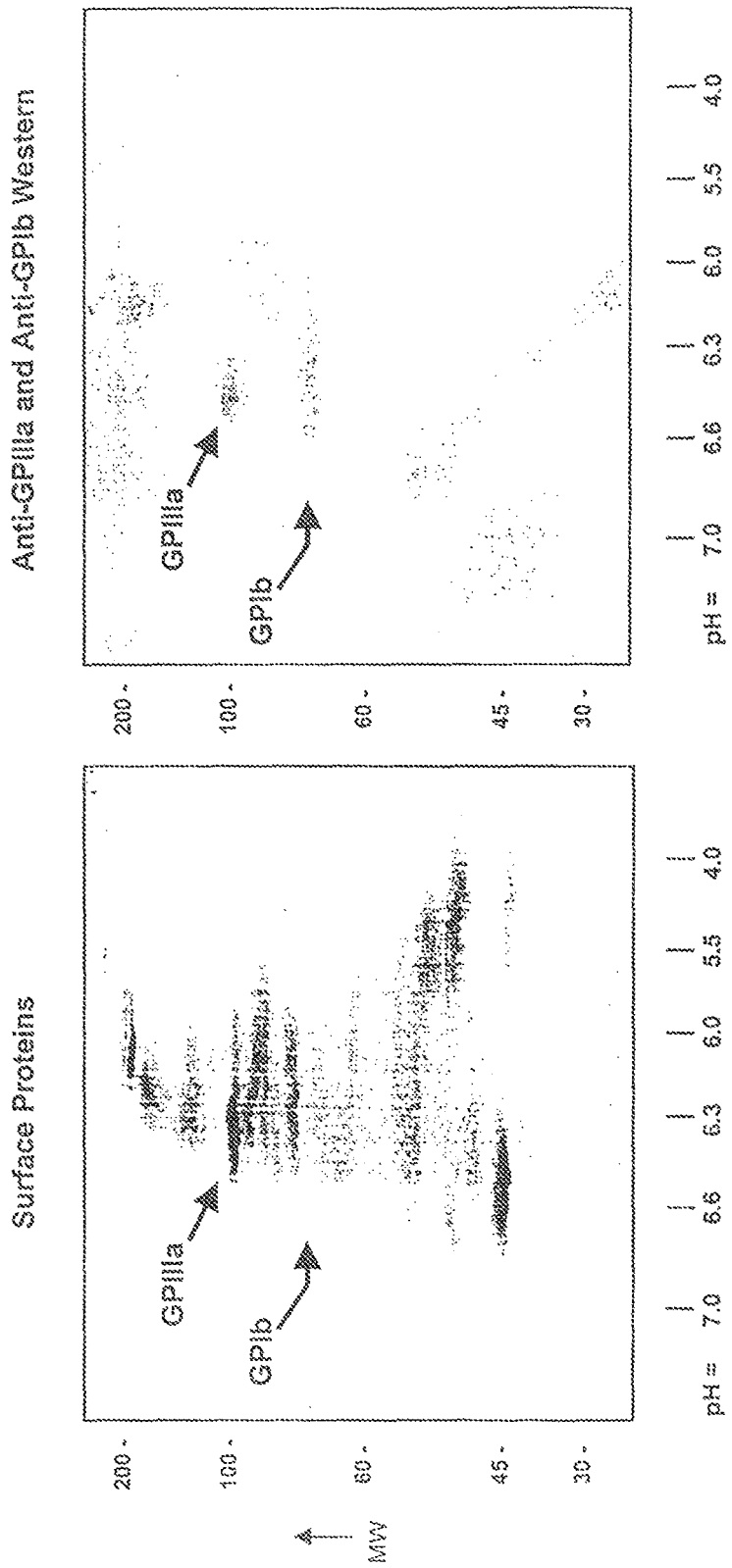
FIG. 7 shows the results of Western blot analysis using anti-GPIIb/IIb and anti-GPIb/V/IX antibodies to confirm the presence of platelet GPIIb/IIb and GPIb/V/IX complexes absorbed by a pGlcNAc polymer fiber matrix.

To determine which proteins are affinity absorbed by pGlcNAc polymers the native state detergent extraction procedure detailed in the "Background and Preliminary Data section" in support of the experiments shown in FIG. 4B can be utilized.

Materials and Methods

Platelet-pGlcNAc networks are formed with both deacetylated and fully acetylated pGlcNAc, and then bound proteins are obtained by extracting the aggregates with deoxycholate and TX-100 at 0° C. The bound protein mixtures is then subjected to 2D IEG. SDS-PAG electrophoresis and Western analysis to identify individual proteins with methods described above.

Conclusion

Of particular interest in this analysis is identifying phosphoproteins and cytoskeletal components that co-absorb with $alpha_{2b}beta_3$-fibrinogen complexes. The study lends further support to the methods of the invention for identifying fibers that interact with platelets.

Third Study
Materials and Methods

To determine which proteins directly contact the pGlcNAc polymers, heterobifunctional cross-linkers are utilized to probe for proteins that are within approximately 20 angstroms of the polysaccharides. The heterobifunctional cross-linker SAND (sulfosuccinimidyl 2-[m-azido-p-nitrobenzamido-125I(iodo)]-1,3'-dithiopropionate) is utilized for these studies. This compound is reducible (so that cross-linked protein-pGlcNAc complexes can be separated for electrophoresis) and transfers the 125I aromatic moiety to proteins when photo-activated. SAND is attached to deacetylated pGlcNAc (with [SAND]<< deacetylated functions) through the succinimidyl moiety. The platelet networks are formed with SAND-pGlcNAc, and then the networks are exposed to long wavelength UV radiation to transfer the radio-iodinated aromatic moiety to platelet proteins that contact the cross-linker before the photo-activated state decays. Samples are extracted with 4% SDS solution at 100° C. to remove proteins that are not cross-linked to the polymer, and then 2D SDS-PAG electrophoresis and autoradiography are performed to identify platelet proteins that came into contact with 125I moiety.

Fourth Study

The relative contribution of alpha$_{2b}$beta$_3$, GPIb-IX, p-selectin and contact (aprotinin-sensitive) protease activation mediated adhesion mechanisms to the platelet-pGlcNAc interaction is examined using the above described experiments.

Materials and Methods

The studies are performed with the following inhibitors listed in Table 2.

TABLE 2

| Target | Inhibitor |
|---|---|
| alpha$_{2b}$beta$_3$ | H12 peptide |
| | ReoPro (Mab 7E; Centocor) |
| GPIb-IX | Mab AP-1 |
| | Mab PP4-3B |
| p-selectin | recombinant p-selectin glycoprotein ligand-1 (Genetics Institute/Wyth) |
| FXII-like contact activation | aprotinin |
| | corn trypsin inhibitor |
| Phos. Ser. | annexin V |

Conclusion

The study provides support for mechanisms by which the compositions and methods of the invention work.

14. EXAMPLE

Examination of the pGlcNAc-Platelet Activation Process

The previous experiments have clearly shown that platelets activate as a result of interaction with pGlcNAc. Inventors also found that calcium is necessary to form pGlcNAc-platelet gels. In order to define the nature of the platelet activation response that is initiated when the cells contact the pGlcNAc polymer several experiments can be performed. In addition to providing insight into the basic nature of the platelet response to foreign materials, the experiments provide additional support for compositions of platelets in pGlcNAc networks, that can be used for hemostasis and promotion of wound healing. Four central aspects of the platelet activation response that occur in the temporal order are examined: membrane potential discharge, intracellular calcium signal generation, protein kinase signal activation and finally secretion of granule contents.

15. EXAMPLE

Examination of the pGlcNAc-Platelet Activation Process

Materials and Methods

High yield platelets were obtained from the American Red Cross, Northeast and stored at 22° C. with agitation for 4 to 10 days prior to study. Platelet-rich plasma was isolated from CPD whole blood collected at Oklahoma Blood Institute and shipped and shorted at 22° C. for 48 hours prior to testing. Platelet poor plasma (PPP), platelet rich plasma (PRP), and PRP plus red blood cells with hematocrit values of 20 V %, 35 V % and 45 V % with and without an equal volume of pGlcNAc (1 mg/ml 0, 9% NaCl) were prepared. A thromboelastrogram was performed with 0.2 M CaCl$_2$ was measured together with thromboxane B2, fragment 1.2, D-dimer, and fibrinogen. Platelet p-selectin, GFIb, factor X, platelet annexin V binding and platelet microparticles together with red blood cell annexin V binding were measured.

Results

In the thromboelastogram, pGlcNAc reduced the R time in PPP, PRP and PRP supplemented with RBC. pGlcNAc increased annexin V and factor X binding to platelets, increased platelet microparticles, and increased RBC annoxin V binding. pGlcNAc alone, RBC alone and pGlcNAc and RBC in combination increased thromboxane A2 production by platelet rich plasma in the presence and absence of calcium.

16. SPECIFIC EMBODIMENTS, CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed:

1. A method for activating platelets isolated from a mammal for later therapeutic use, the method comprising contacting ex vivo (i) platelets that have expired for transfusion purposes, (ii) poly-β-1→4-N-acetylglucosamine fibers, wherein the poly-β-1→4-N-acetylglucosamine fibers are about 10 to 500 nm in width and about 50 to 750 microns in length as detected by scanning electron microscopy, and (iii) a calcium salt or a calcium salt solution, such that a gel is formed.

2. The method of claim 1, wherein the platelets have been stored for 5 to 15 days.

3. The method of claim 1, wherein the platelets have been stored for 6 to 15 days.

4. A method for accelerating wound healing and/or reducing hemostasis in a patient in need thereof comprising administering to a wound in said patient platelets activated using the method of claim 3.

5. The method of claim 4, wherein the platelets had been derived from the patient.

6. The method of claim 1, wherein the gel comprises at least $1 \times 10^6$ of the platelets bound per mg of the poly-β-1→4-N-acetylglucosamine fibers.

7. The method of claim 1, wherein the platelets activated using the method of claim 12 are activated as determined by a hypotonic stress response assay, a collagen-induced aggregation test, an adenosine diphosphate-induced aggregation test, morphological observation, detection of surface exposure of alpha granule contents, or detection of the conformation of alpha$_{2b}$ beta$_3$ integrin.

8. The method of claim 1, wherein the poly-β-1→4-N-acetylglucosamine fibers are formulated as a slurry.

9. The method of claim 8, wherein the slurry comprises 1 mg or 2 mg of fiber per 1 ml of 0.9% NaCl solution.

10. The method of claim 8, wherein the slurry comprises 0.5-20 mg of fiber per 1 ml of distilled water.

11. The method of claim 8, wherein the slurry comprises 1 mg of fiber per 5 ml of distilled water.

12. The method of claim 1, further comprising contacting ex vivo at least 0.025 M magnesium salt solution per 1 mg of the poly-β-1→4-N-acetylglucosamine fibers.

13. The method of claim 1, wherein the platelets are in the form of platelet rich plasma.

14. The method of claim 1, wherein the poly-β-1→4-N-acetylglucosamine fibers are formulated as a slurry, wherein the platelets are in the form of platelet rich plasma, and wherein the platelet rich plasma and the slurry are mixed in a volume ratio of 50:50.

15. The method of claim 1, wherein the calcium salt is CaCl$_2$.

16. The method of claim 1, further comprising freezing the gel at about 0° C. to -80° C. for later therapeutic use.

17. The method of claim 1, further comprising storing the gel at about 1° C. to 25° C.

18. The method of claim 1, wherein at least 40% of N-acetylglucosamine monosaccharides of the poly-β-1→4-N-acetylglucosamine are acetylated.

19. The method of claim 1, wherein at least 70% of N-acetylglucosamine monosaccharides of the poly-β-1→4-N-acetylglucosamine are acetylated.

20. The method of claim 1, wherein the poly-β-1→4-N-acetylglucosamine is fully acetylated.

21. The method of claim 1, wherein the poly-β-1→4-N-acetylglucosamine is free of protein, and substantially free of organic and inorganic contaminants.

22. The method of claim 1, wherein poly-β-1→4-N-acetylglucosamine is derived from microalgae.

23. The method of claim 1, wherein, prior to the contacting, the platelets have been isolated from blood.

24. The method of claim 1, wherein the gel comprises at least $5 \times 10^7$ of the platelets bound per mg of the poly-β-1→4-N-acetylglucosamine fibers.

25. The method of claim 1, wherein the gel comprises at least $5 \times 10^8$ of the platelets bound per mg of the poly-β-1→4-N-acetylglucosamine fibers.

26. The method of claim 1, wherein the poly-β-1→4-N-acetylglucosamine fibers are about 25 to 250 nm in width as detected by scanning electron microscopy.

27. A method for accelerating wound healing and/or reducing hemostasis in a patient in need thereof comprising administering to a wound in said patient platelets activated using the method of claim 1.

28. The method of claim 27, wherein the platelets had been derived from the patient.

29. A method for activating platelets isolated from a mammal for later therapeutic use, the method comprising contacting ex vivo (i) platelets, and (ii) poly-β-1→4-N-acetylglucosamine fibers, wherein the poly-β-1→4-N-acetylglucosamine fibers are about 10 to 500 nm in width and about 50 to 750 microns in length as detected by scanning electron microscopy, such that a platelet-poly-β-1→4-N-acetylglucosamine composition comprises at least $1 \times 10^6$ of the platelets bound per mg of the poly-β-1→4-N-acetylglucosamine fibers is formed.

30. The method of claim 29, wherein the platelets have been stored for 5 to 15 days.

31. The method of claim 29, wherein the platelets have been stored for 6 to 15 days.

32. The method of claim 29, wherein the platelets have expired for transfusion purposes.

33. The method of claim 29, further comprising contacting ex vivo (i) and (ii) of claim 29 with (iii) a calcium salt or a calcium salt solution, such that a gel is formed.

34. The method of claim 33, wherein the calcium salt is CaCl$_2$.

35. The method of claim 29, wherein the platelet-poly-β-1→4-N-acetylglucosamine composition comprises at least $5 \times 10^7$ of the platelets bound per mg of the poly-β-1→4-N-acetylglucosamine fibers.

36. The method of claim 29, wherein the platelet-poly-β-1→4-N-acetylglucosamine composition comprises at least $5 \times 10^8$ of the platelets bound per mg of the poly-μ-1→4-N-acetylglucosamine fibers.

37. The method of claim 29, wherein the platelets activated using the method of claim 24 are activated as determined by a hypotonic stress response assay, a collagen-induced aggregation test, an adenosine diphosphate-induced aggregation test, morphological observation, detection of surface exposure of alpha granule contents, or detection of the conformation of alpha$_{2b}$ beta$_3$ integrin.

38. The method of claim 29, wherein the platelets are in the form of platelet rich plasma.

39. The method of claim 29, wherein at least 40% of N-acetylglucosamine monosaccharides of the poly-β-1→4-N-acetylglucosamine are acetylated.

40. The method of claim 29, wherein the poly-β-1→4-N-acetylglucosamine is fully acetylated.

41. The method of claim 29, wherein the poly-β-1→4-N-acetylglucosamine is derived from microalgae.

42. The method of claim 29, wherein the poly-β-1→4-N-acetylglucosamine fibers are about 25 to 250 nm in width as detected by scanning electron microscopy.

43. A method for accelerating wound healing and/or reducing hemostasis in a patient in need thereof comprising administering to a wound in said patient platelets activated using the method of claim 29.

44. The method of claim 43, wherein the platelets had been derived from the patient.

* * * * *